US007687266B2

(12) United States Patent
Chambers et al.

(10) Patent No.: US 7,687,266 B2
(45) Date of Patent: Mar. 30, 2010

(54) PLURIPOTENCY DETERMINING FACTORS AND USES THEREOF

(75) Inventors: Ian Chambers, Edinburgh (GB); Austin Gerard Smith, Edinburgh (GB)

(73) Assignee: University of Edinburgh, Edinburgh (GB)

( * ) Notice: Subject to any disclaimer, the term of this patent is extended or adjusted under 35 U.S.C. 154(b) by 469 days.

(21) Appl. No.: 10/502,972

(22) PCT Filed: Jan. 30, 2003

(86) PCT No.: PCT/GB03/00366

§ 371 (c)(1), (2), (4) Date: Apr. 21, 2005

(87) PCT Pub. No.: WO03/064463

PCT Pub. Date: Aug. 7, 2003

(65) Prior Publication Data

US 2005/0255573 A1   Nov. 17, 2005

(30) Foreign Application Priority Data

Jan. 30, 2002   (GB)   ................................ 0202149.1

(51) Int. Cl.
*C12N 15/09*   (2006.01)
*C12N 5/06*   (2006.01)
*C12N 5/08*   (2006.01)

(52) U.S. Cl. .................. 435/455; 435/354; 435/366

(58) Field of Classification Search ................ 435/354, 435/366, 183
See application file for complete search history.

(56) References Cited

U.S. PATENT DOCUMENTS

2005/0196754 A1*   9/2005   Drmanac et al. ............... 435/6

FOREIGN PATENT DOCUMENTS

| WO | WO 96/22693 A1 | 8/1996 |
| WO | WO 97/30151 A1 | 8/1997 |
| WO | WO 01/66697 A2 | 9/2001 |

OTHER PUBLICATIONS

Hansis et al Molecular Human Reproduction, 6(11), 999-1004, 2000.*
Romano, Drug News Perspect, 2003, 1645: 267.*
Gorba et al Pharmacol Res, 2003, 47(4): 269-278.*
Buehr et al, Philos Trans R Soc Lond B Biol Sci. 2003; 358(1436): 1397-402.*
Chambers et al., Cell, 2003, 113(5), 643-655.*
Mitsui et al Cell, 2003, 113, 631-642.*
Skolnick et al Trends in Biotech, 2000,18, 34-39.*
Ngo et al., 1994, The protein Folding Problem and Tertiary Structure Prediction, pp. 491-495.*
Constantinescu et al J Cell Mol Med. 2003; 7(2):103-12.*
Davis, New Biologist, 1990, 2(5), 410-419.*
Reik et al Science, 2001, 293: 1089-1093.*
Rideout III et al Science, 2001, 293: 1093-1098.*
Andrews et al Biochem Soc Trans. 2005; 33(Pt 6):1526-30.*
Koestenbauer et al Am J Reprod lmmunol. 2006; 55(3):169-80.*
Sato et al.Nat. Med., 2004, 10:55-63.*
Humphrey et al. (2004) Stem Cells 22: 522-530.*
Daheron et al., 2004, Stem Cells 22,770-778.*
Maiorella et al Bio/technology, 1993, 11(3), p. 387-392.*
Tachikawa et al PNAS, 2004, 101(42), 15225-15230.*
D'Ippolito et al and J Cell Sci. 2004; 117(Pt 14): 2971-81.*
Ginis et al Dev. Biol., 2004, (269), 360-380.*
Pera et al Journal of Cell Science, 2000, 113, 5-10.*
Hochedlinger et al Cell, 2005, 121: 465-477.*
Ezeh et al Cancer, 2005, 104, 2255-2265.*
Herszfeld et al Nature Biotechnology, 2006, 24 (3), 351-357.*
Unverified English Translation of WO 02/097090 A1 (Document AL1).
Database EMBL Online, Database accession No. AK022643, Isogai, T. and Otsuki, T., "*Homo sapiens* cDNA FLJ12581 fis, clone NT2RM4001140, weakly similar to Homeobox Protein MSH-D," (Sep. 29, 2000).
International Search Report for International Patent Application PCT/GB03/00366, issued Sep. 24, 2003.
Amit, M., et al., "Clonally Derived Human Embryonic Stem Cell Lines Maintain Pluripotency and Proliferative Potential for Prolonged Periods of Culture," *Dev. Biol. 227*:271-278, Academic Press (2000).
Baron, U. and Bujard, H., "Tet Repressor-Based System for Regulated Gene Expression in Eukaryotic Cells: Principles and Advances," *Meth. Enzymol. 327*:401-421, Academic Press (2000).
Berger, C.N. and Sturm, K.S., "Self Renewal of Embryonic Stem Cells in the Absence of Feeder Cells and Exogenous Leukaemia Inhibitory Factor," *Growth Factors 14*:145-159, Overseas Publishers Association (1997).
Gassmann, M., et al., "Maintenance of an extrachromosomal plasmid vector in mouse embryonic stem cells," *Proc. Natl. Acad. Sci. USA 92*:1292-1296, The National Academy of Science (1995).
Håkelien, A.-M., et al., "Reprogramming fibroblasts to express T-cell functions using cell extracts," *Nature Biotechnol. 20*:460-466, Nature Publishing Group (May 2002).
Isalan, M. and Choo, Y., "Rapid, High-Throughput Engineering of Sequence-Specific Zinc Finger DNA-Binding Proteins," *Meth. Enzymol. 340*:593-609, Academic Press (2001).

(Continued)

*Primary Examiner*—Deborah Crouch
*Assistant Examiner*—Anoop Singh
(74) *Attorney, Agent, or Firm*—Sterne, Kessler, Goldstein & Fox P.L.L.C.

(57) ABSTRACT

Pluripotency determining factors are described which act intracellularly and maintain a pluripotent cell in a pluripotent state in the absence of gp130 activation, which maintain or confer pluripotency of a human stem cell, which maintain or confer pluripotency of a mouse ES cell, and which maintain or confer pluripotency of a stem cell from a non-permissive strain of mice. The factors and vectors encoding or activating the factors are used to maintain and derive pluripotent cells, especially of higher mammals, including humans.

11 Claims, 32 Drawing Sheets

OTHER PUBLICATIONS

Li, M., et al., "Essential function of LIF receptor in motor neurons," *Nature 378*:724-727, Nature Publishing Group (1995).

NCBI Entrez, GenBank Report, Accession No. AK010332, Carninci, P., et al., Entry Date 2001, Last Updated Sep. 2005.

Picard, D., "Posttranslational Regulation of Proteins by Fusions to Steroid-Binding Domains," *Meth. Enzymol. 327*:385-401, Academic Press (2000).

Rathjen, P.D., et al., "Developmentally programmed induction of differentiation inhibiting activity and the control of stem cell populations," *Genes Dev. 4*:2308-2318, Cold Spring Harbor Laboratory Press (1990).

Schwarze, S.R., et al., "Protein transduction: unrestricted delivery into all cells?," *Trends Cell Biol. 10*:290-295, Elsevier Science Ltd. (2000).

Xu, C.., et al., "Feeder-free growth of undifferentiated human embryonic stem cells," *Nature Biotechnol. 19*:971-974, Nature Publishing Group (2001).

Yamanaka, S. and Mitsui, K., "Animal Molecular Technology," Research and Education Center for Genetic Information, 2 pages, accessed online at http://gtcw3.aist-nara.ac.jp/yamanaka/yamanaka.html, last modified Mar. 2005.

Yoshida, K., et al., "Maintenance of the pluripotential phenotype of embryonic stem cells through direct activation of gp130 signalling pathways," *Mech. Dev. 45*:163-171, Elsevier Science Ireland Ltd. (1994).

Unverified English Translation of WO 02/097090 A1 (Document AL1), 2002.

* cited by examiner

Episomal ES cell vector

Integration and subsequent removal of a loxP flanked PDF transgene

FIG. 3B

```
Mm Pdf   MSVGLPGPHSLPSSEEASNGNASSMPAVFHP-ENYSCLQ  39
Hs PDF   MSVDPACPQSLP-CFEASDCKESSPMPVICGPEENYPSLQ  39

Mm Pdf   GSATEMLCTEAASPRPSSEDLPLQGSPDSSTSPKQKLSSP  79
Hs PDF   MSSAEMPHTETVSPLPSSMDLLIQDSPDSSTSPKGKQPTS  79

Mm Pdf   EADKGPEEEENKVLARKQKMRTVFSQAQLCALKDRFQKQK  119
Hs PDF   -AEKSVAKKEDKVPVKKQKTRTVFSTQLCVLNDRFQRQK  118

Mm Pdf   YLSLQQMQELSSILNLSYKQVKTWFQNQRMKCKRWQKNQW  159
Hs PDF   YLSLQQMQELSNILNLSYKQVKTWFQNQRMKSKRWQKNNW  158

Mm Pdf   LKTSNGLIQKGSAPVEYPSIHCSYPQGYLVNASGSLSMWG  199
Hs PDF   PKNSNGVTQKASAP-TYPSLYSSYHQGCLVNPTGNLPMWS  197

Mm Pdf   SQTWTNPTWSSQTWTNPTWNNQTWTNPTWSSQAWTAQSWN  239
Hs PDF   NQTWNNSTWS-----NQTQNIQSWSNHSWNTQTWCTQSWN  232

Mm Pdf   GQPWNAAPLHNFGEDFLQPYVQLQQNFSASDLEVNLEAT- 278
Hs PDF   NQAWN-SPFYNCGEESLQSCMQFQPNSPASDLEAALEAAG  271

Mm Pdf   ------RESHAHFSTPQALELFLNYSVTP-PGEI       305
Hs PDF   EGLNVIQQTTRYFSTPQTMDLFLNYSMNMQPEDV       305
```

FIG. 3C

```
                     *
Pdf cDNA    ggggctggtgtgagatggctcagtgtggacaagagagcacccgactgctcttccgaagtcaggagctcaaa 1178
            |||||||||  ||||||||||||  |||||||||||| ||||||||||||||||| ||||||||||||||
B2 repeat   ggggctggagagatggctcagcggtt-aagagcact-gactgctcttccgaaggtcctgagttcaat 152

*                            *  **  *
Pdf cDNA    tcccagcaaccacacggcgggctcacaaccatacgcaacagatctgacgcccctctctggagtgtc 1112
            ||| ||||||||| |||| ||||||||||| || || ||||||| |||||| || ||||| ||||
B2 repeat   tcccgcaaccacatggtgggctcacaaccatccgtaatgagatctggtgccctcttctggagtgtc 218

*           *          *   * *          *
Pdf cDNA    cgaagacagccacagtgtactcacacataatgaacaaataaa---tctttaaaaaaatatgaaaa 1050
            ||||||||| |||||||||||  |||||| |||| |||||||   |||||||||  ||| ||||
B2 repeat   tgaggacagtgtacagtgtacttacatataataataaaaatctttaaaaaaaaatctttaaaaaaaaaaaa 284
```

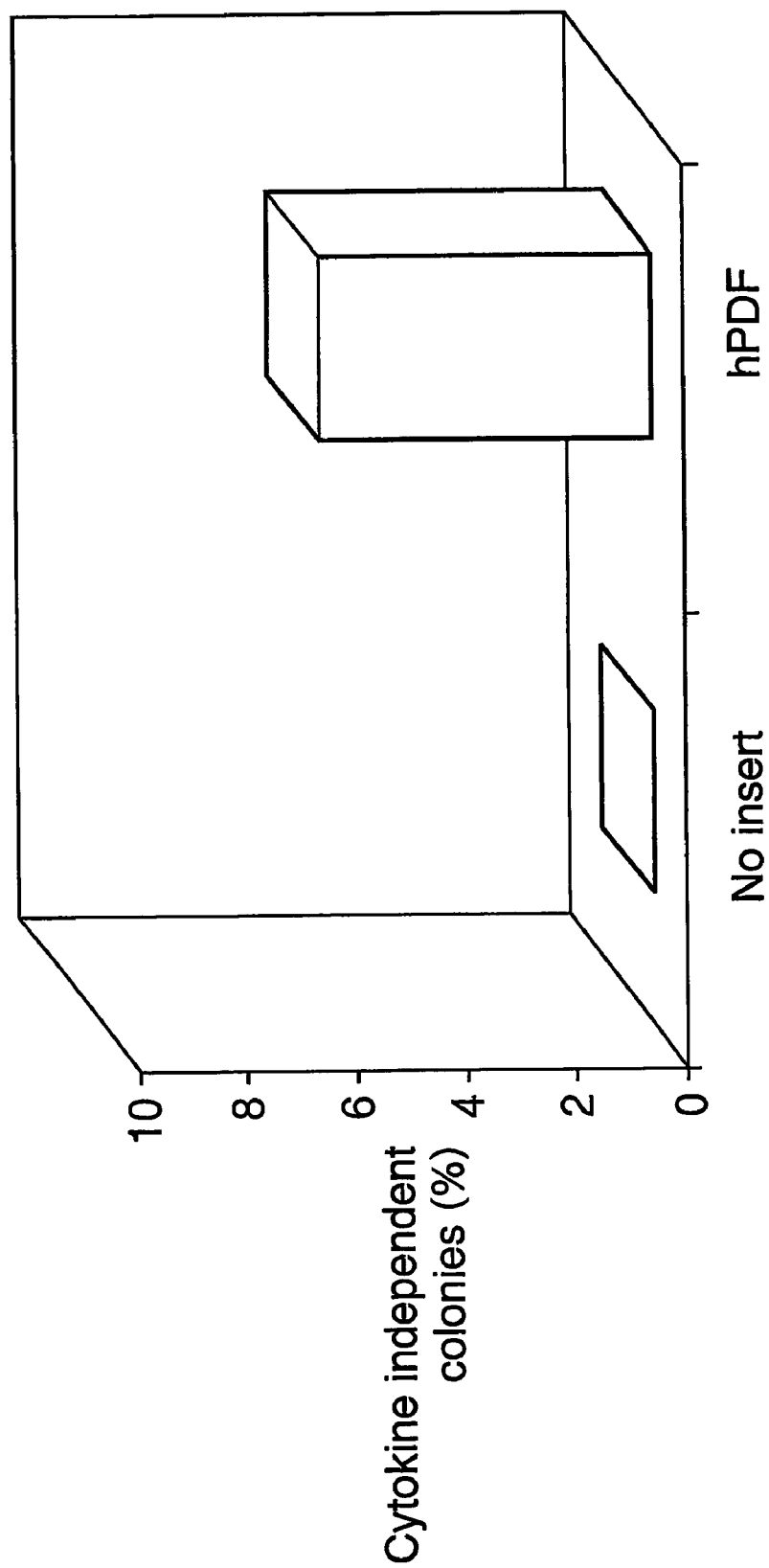

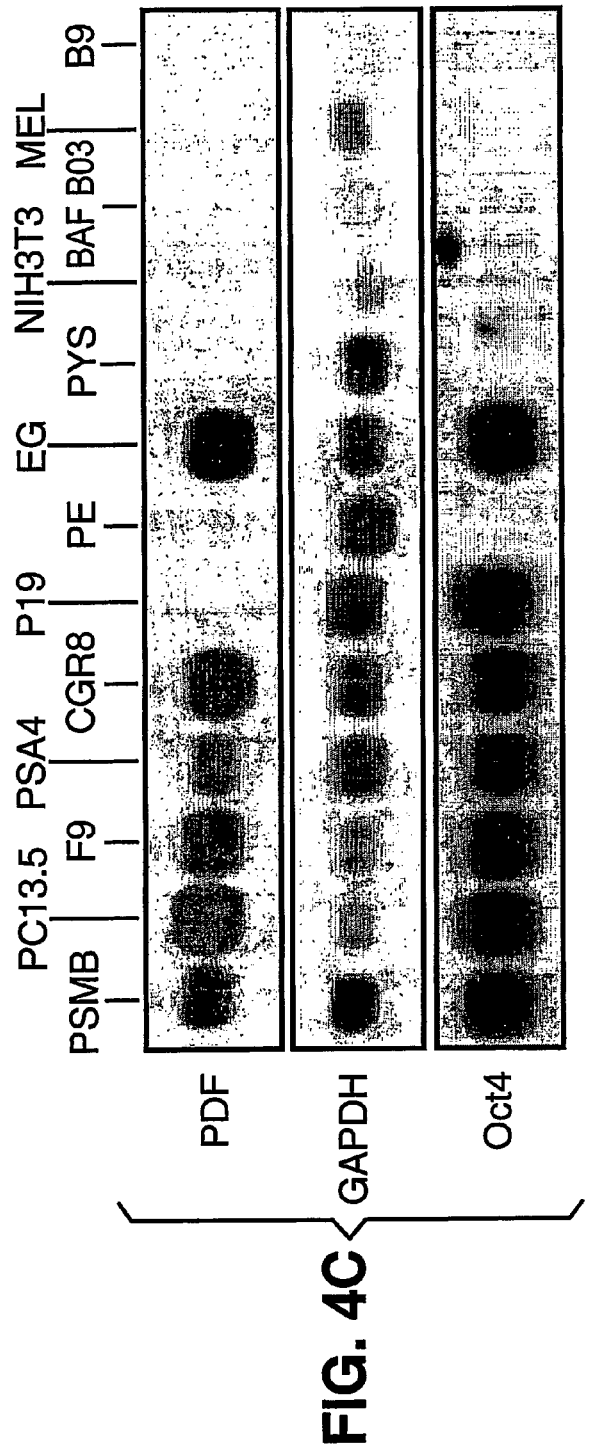
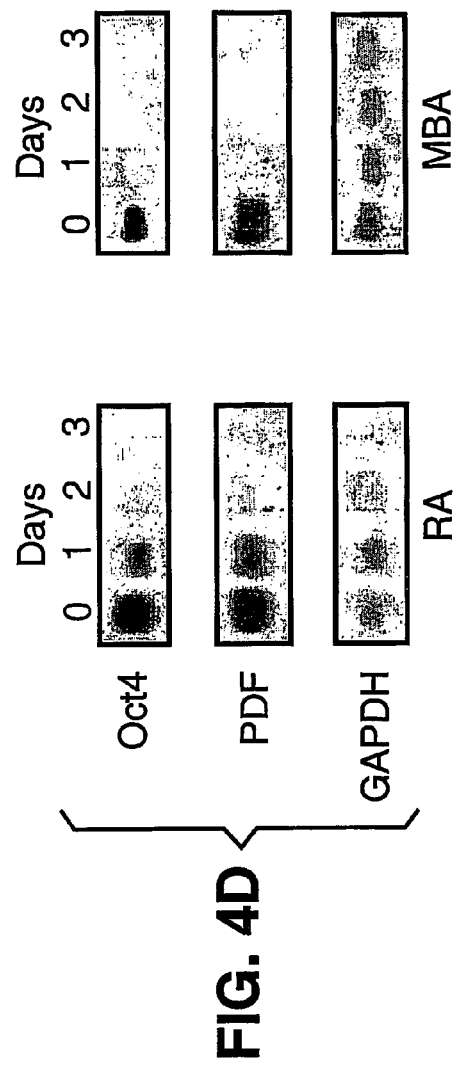
FIG. 4C
FIG. 4D

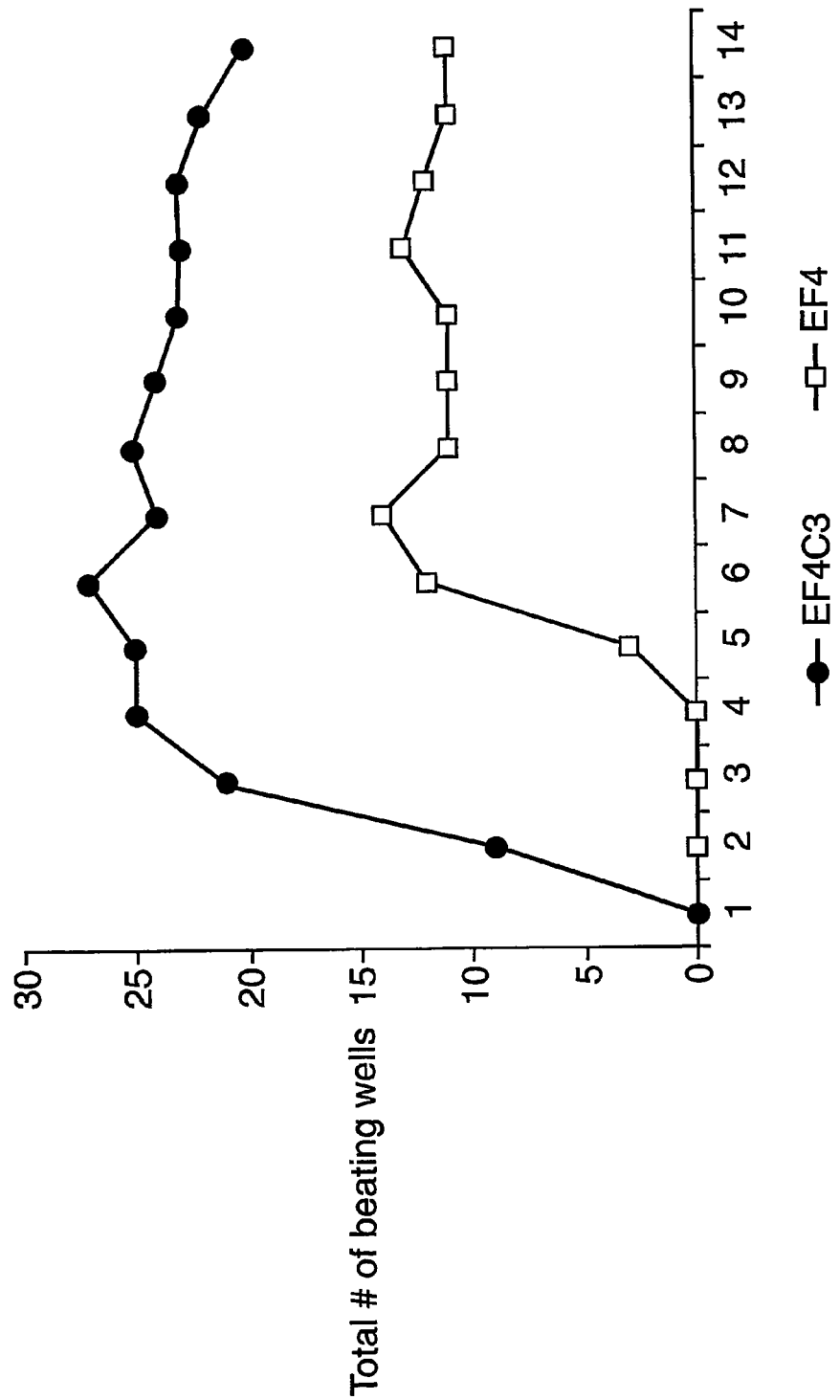

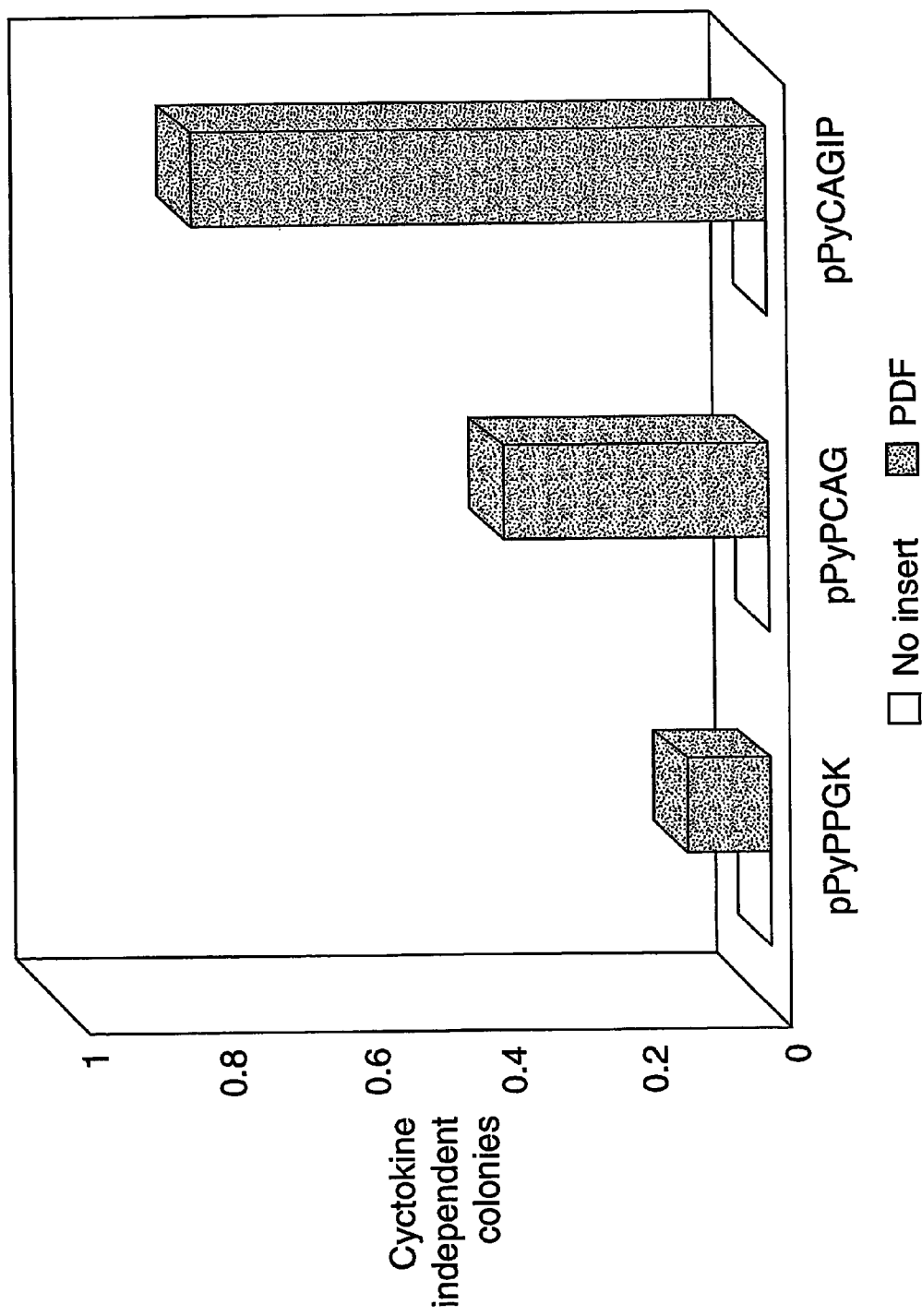

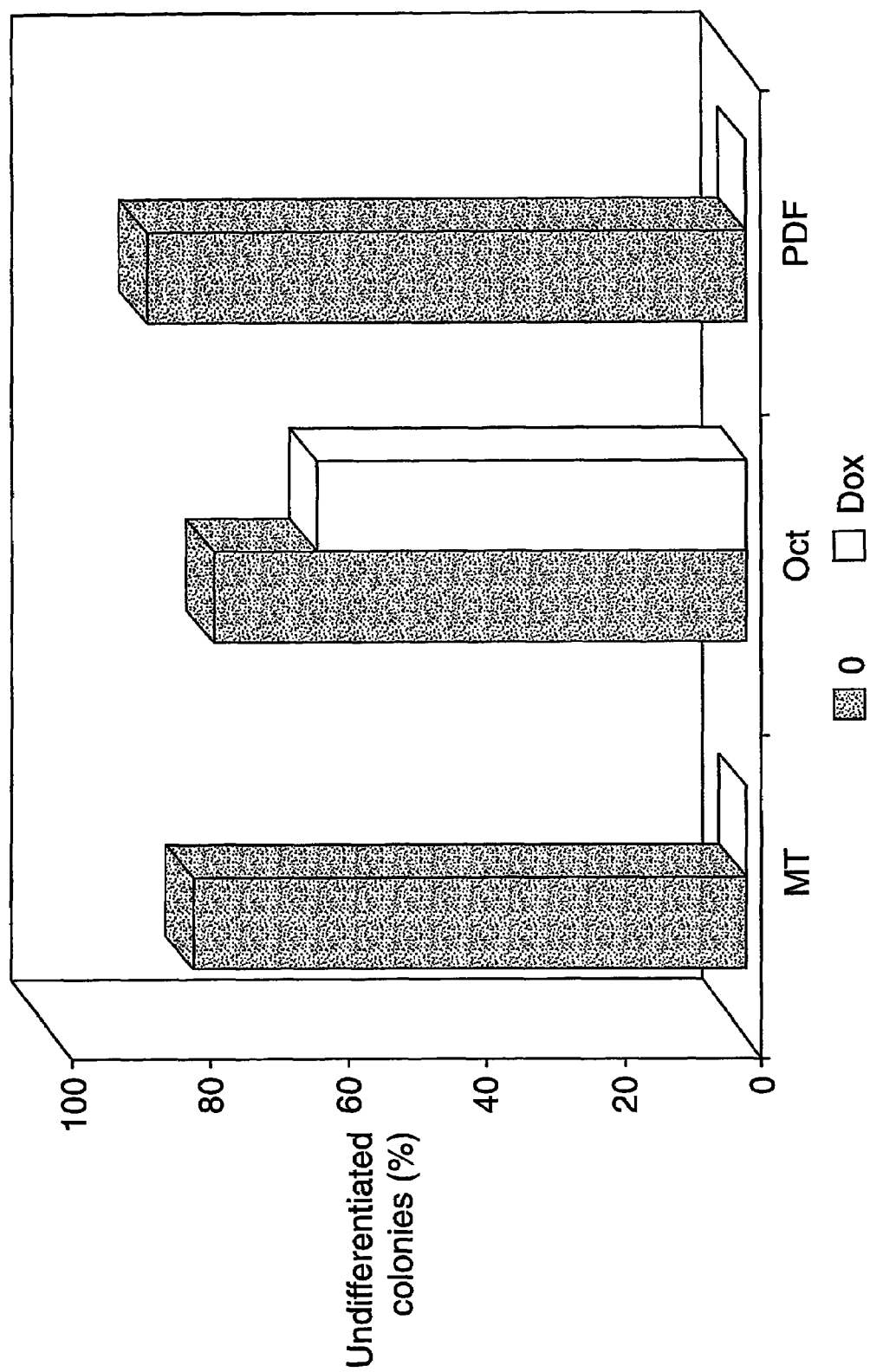

FIG. 14a
+CM
FIG. 14b
-CM
hPDF D7
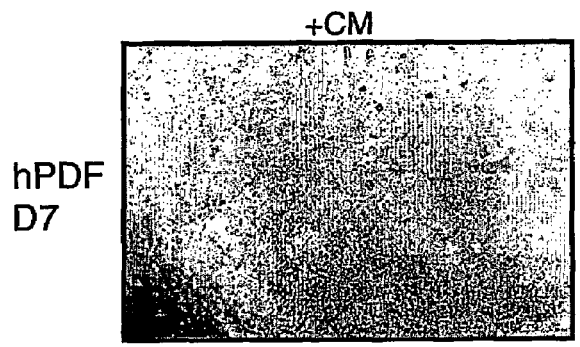
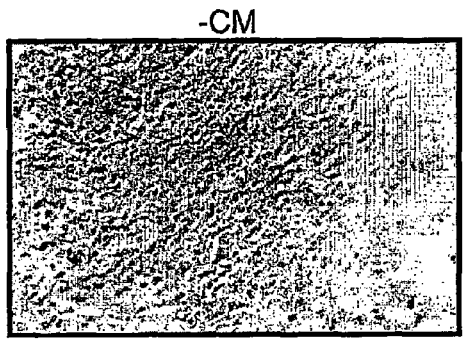
FIG. 14c
FIG. 14d
hPDF E7
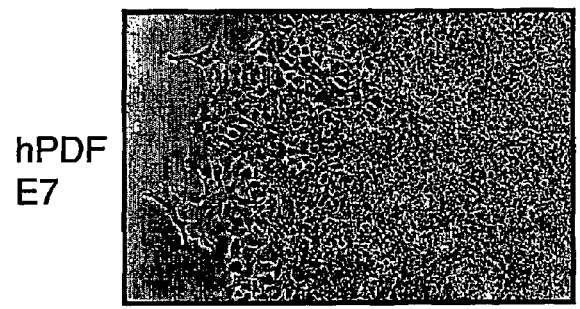
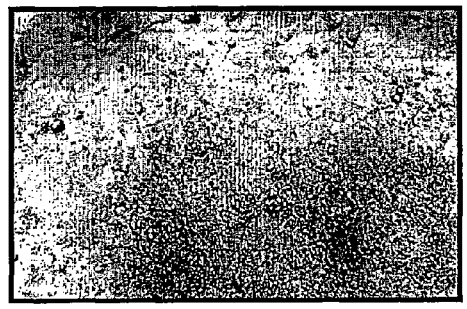
FIG. 14e
FIG. 14f
GFP C15
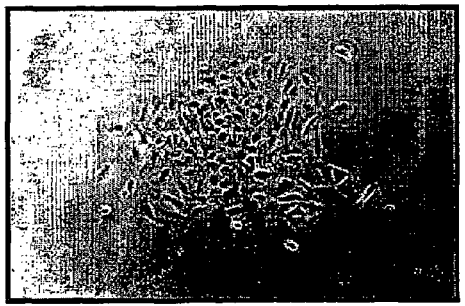
FIG. 14g
FIG. 14h
27X-1
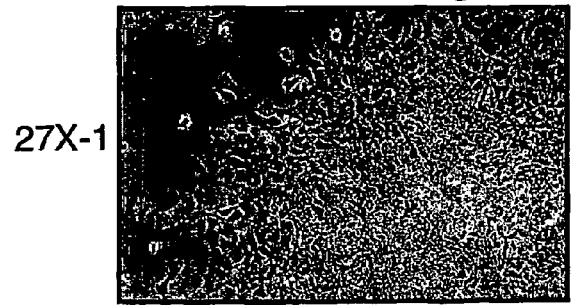
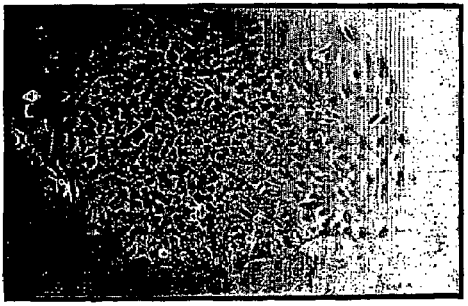

FIG. 15a +CM FIG. 15b
hPDF D7 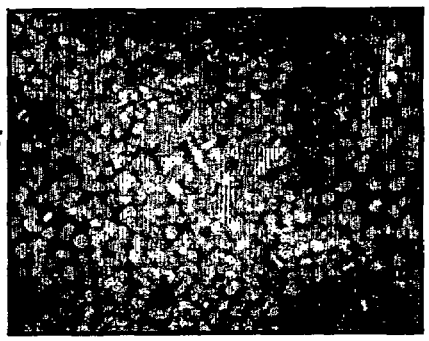 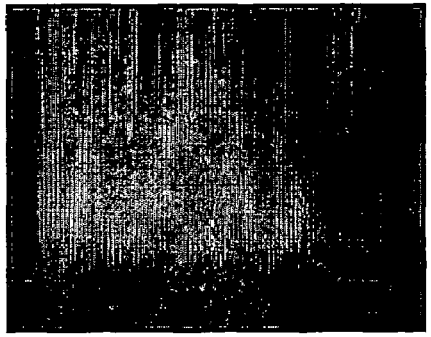
FIG. 15c FIG. 15d
hPDF E7 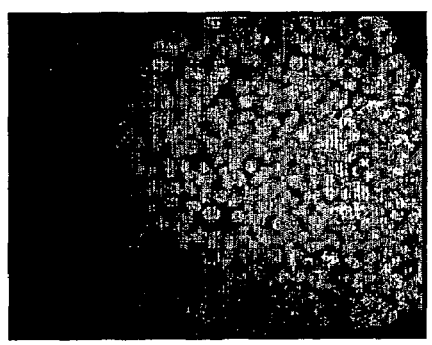 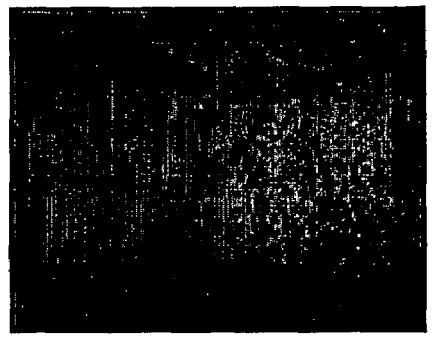
FIG. 15e FIG. 15f
GFP C15 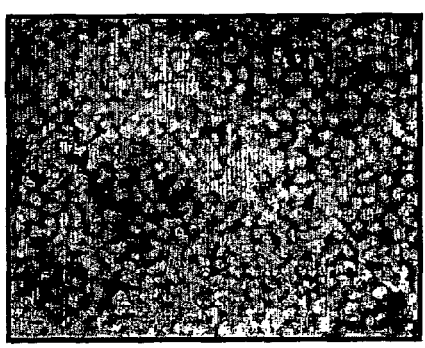 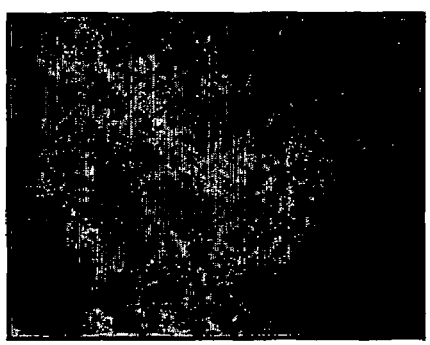
FIG. 15g FIG. 15h
27X-1 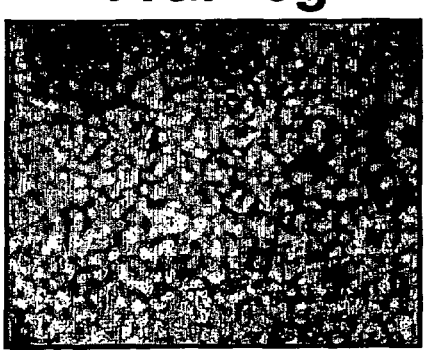 

FIG. 15i   -CM   FIG. 15j
hPDF D7
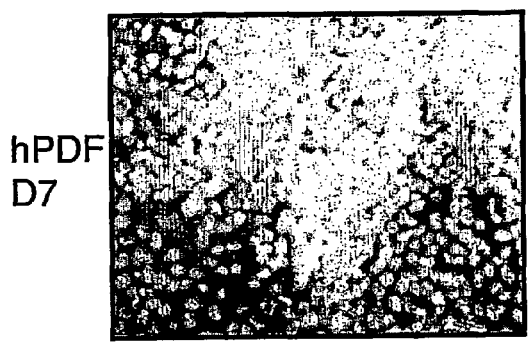 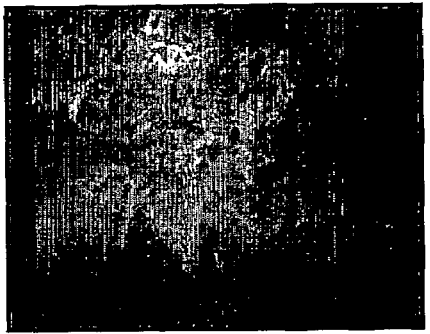
FIG. 15k   FIG. 15l
hPDF E7
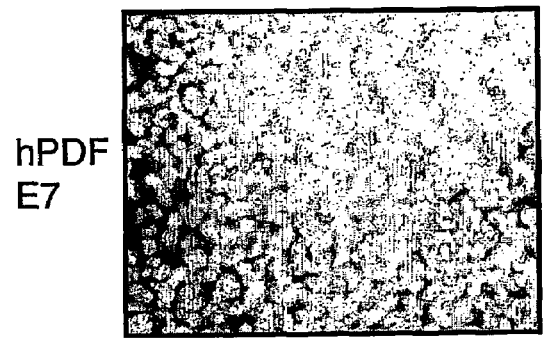 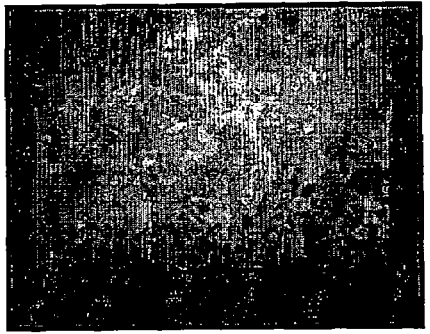
FIG. 15m   FIG. 15n
GFP C15
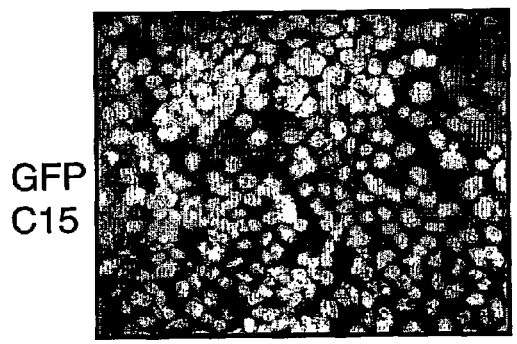 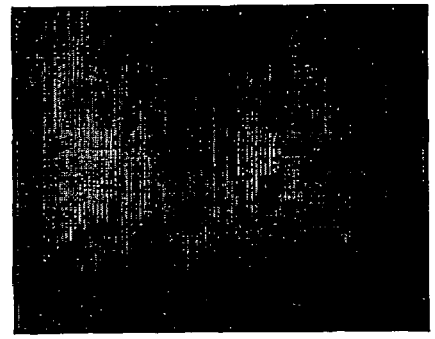
FIG. 15o   FIG. 15p
27X-1
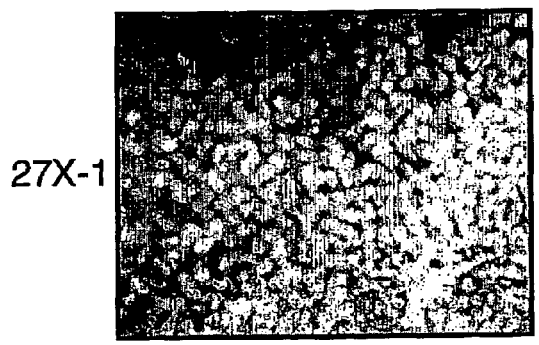 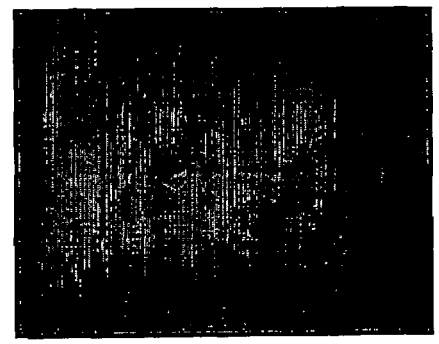

SEQUENCE LISTING

<160> NUMBER OF SEQ ID NOS: 25

<210> SEQ ID NO 1
<211> LENGTH: 2185
<212> TYPE: DNA
<213> ORGANISM: Mus musculus

<400> SEQUENCE: 1

```
gagataggct gatttggttg gtgtcttgct ctttctgtgg gaaggctgcg gctcacttcc      60
ttctgacttc ttgataattt tgcattagac atttaactct tctttctatg atctttcctt     120
ctagacactg agttttttgg ttgttgccta aaaccttttc agaaatccct tccctcgcca     180
tcacactgac atgagtgtgg gtcttcctgg tccccacagt ttgcctagtt ctgaggaagc     240
atcgaattct gggaacgcct catcaatgcc tgcagttttt catcccgaga actattcttg     300
cttacaaggg tctgctactg agatgctctg cacagaggct gcctctcctc gcccttcctc     360
tgaagacctg cctcttcaag gcagccctga ttcttctacc agtcccaaac aaaagctctc     420
aagtcctgag gctgacaagg gccctgagga ggaggagaac aaggtccttg ccaggaagca     480
gaagatgcgg actgtgttct ctcaggccca gctgtgtgca ctcaaggaca ggtttcagaa     540
```

```
gcagaagtac ctcagcctcc agcagatgca agaactctcc tccattctga acctgagcta    600
taagcaggtt aagacctggt ttcaaaacca aaggatgaag tgcaagcggt ggcagaaaaa    660
ccagtggttg aagactagca atggtctgat tcagaagggc tcagcaccag tggagtatcc    720
cagcatccat tgcagctatc cccagggcta tctggtgaac gcatctggaa gcctttccat    780
gtggggcagc cagacttgga ccaacccaac ttggagcagc cagacctgga ccaacccaac    840
ttggaacaac cagacctgga ccaacccaac ttggagcagc caggcctgga ccgctcagtc    900
ctggaacggc cagccttgga atgctgctcc gctccataac ttcggggagg actttctgca    960
gccttacgta cagttgcagc aaaacttctc tgccagtgat ttggaggtga atttggaagc   1020
cactagggaa agccatgcgc attttagcac cccacaagcc ttggaattat tcctgaacta   1080
ctctgtgact ccaccaggtg aaatatgaga cttacgcaac atctgggctt aaagtcaggg   1140
caaagccagg ttcctttctt tttccaaata ttttcatatt tttttaaag atttatttat   1200 tcattatatg taagtaccct gtagctgtct tcatacactc caaaaaggg cgtcagatct   1260 tgttacgtat ggttgtgagc caccatgtgg ttgctgggat ttgaactcct gaccttcgga   1320
agagcagtcg ggtgctctta ccactgagc catctcacca gcccctggtt tattttttta   1380
attattattt gcttttttgtt tatcgagaca gggtttctct gcatagctct aattgtcttt   1440
gaactagctc tgcagaccag cctggccttg aactcagaga tctgcccact tatctttgcc   1500
tcctgaatgc tgggaccaaa ggtggcatac caccacacct ggcatatata ttgtttattt   1560
ctatttctat ttttattggt gccagagcaa acctaggact tagaacatgc tgggcaccaa   1620
ctcaacttct gagctctatt tacaacttgg tgtgttagtg tatttgtctt agttctgaat   1680
ttgtcctttt tttagtgtta actctaggct ttggagacag tgaggtgcat atactctctc   1740
cttcccaaga ataagtgctt gaacaccctt acccacgccc acccacccat gctagtcttt   1800
tttcttagaa gcgtgggtct tggtatacac tgtgtcattt tgaggggtga ggtttaaaag   1860
tatatacaaa gtataacgat atggtggcta ctctcgagga tgagacagaa ggaccaggag   1920
tttgagggta gctcagatat gcaataagtt caaggccaac ctgtactatg tttaaatagt   1980
aagacagcat ctcgataaaa taataaaact aaagtctcaa caaaataaaa gctttcacct   2040
attaaggtgc ttgcttgtcc ttggagtccc caagagtaa ctgctatgtt aatatctgta    2100
gaaagatgtt tatatttgac tgtaccatga tgaaccgatg ccagctggac tagtttaaac   2160
aaaataaaac actaattta cctttt                                          2185
```

<210> SEQ ID NO 2
<211> LENGTH: 305
<212> TYPE: PRT
<213> ORGANISM: Mus musculus

<400> SEQUENCE: 2

```
Met Ser Val Gly Leu Pro Gly Pro His Ser Leu Pro Ser Ser Glu Glu
1               5                   10                  15

Ala Ser Asn Ser Gly Asn Ala Ser Ser Met Pro Ala Val Phe His Pro
            20                  25                  30

Glu Asn Tyr Ser Cys Leu Gln Gly Ser Ala Thr Glu Met Leu Cys Thr
        35                  40                  45

Glu Ala Ala Ser Pro Ala Pro Ser Ser Glu Asp Leu Pro Leu Gln Gly
    50                  55                  60

Ser Pro Asp Ser Ser Thr Ser Pro Lys Gln Lys Leu Ser Ser Pro Glu
65                  70                  75                  80
```

```
Ala Asp Lys Gly Pro Glu Glu Glu Asn Lys Val Leu Ala Arg Lys
            85                  90                  95
Gln Lys Met Arg Thr Val Phe Ser Gln Ala Gln Leu Cys Ala Leu Lys
        100                 105                 110
Asp Arg Phe Gln Lys Gln Leu Tyr Leu Ser Leu Gln Gln Met Gln Gln
            115                 120                 125
Leu Ser Ser Ile Leu Asn Leu Ser Tyr Lys Val Lys Thr Trp Phe
        130                 135                 140
Gln Asn Gln Arg Met Lys Cys Lys Arg Tyr Gln Leu Asn Gln Trp Leu
145                 150                 155                 160
Lys Thr Ser Asn Gly Leu Ile Gln Lys Gly Ser Ala Pro Val Glu Tyr
                165                 170                 175
Pro Ser Ile His Cys Ser Tyr Pro Gln Gly Tyr Leu Val Asn Ala Ser
            180                 185                 190
Gly Ser Leu Ser Met Trp Gly Ser Gln Thr Trp Thr Asn Pro Thr Trp
        195                 200                 205
Ser Ser Gln Thr Trp Thr Asn Pro Thr Trp Asn Asn Gln Thr Trp Thr
210                 215                 220
Asn Pro Thr Trp Ser Ser Gly Ala Trp Thr Ala Gln Ser Trp Asn Gly
225                 230                 235                 240
Gly Pro Trp Asn Ala Ala Pro Leu His Asn Phe Gly Glu Asp Phe Leu
                245                 250                 255
Gln Pro Tyr Val Gln Leu Gln Gln Asn Phe Ser Ala Ser Asp Leu Glu
            260                 265                 270
Val Asn Leu Glu Ala Thr Arg Glu Ser His Ala His Phe Ser Thr Pro
        275                 280                 285
Gln Ala Leu Glu Leu Phe Leu Asn Tyr Ser Val Thr Pro Pro Gly Glu
        290                 295                 300
Ile
305

<210> SEQ ID NO 3
<211> LENGTH: 2114
<212> TYPE: DNA
<213> ORGANISM: Homo sapiens

<400> SEQUENCE: 3
attataaatc tagagactcc aggattttaa cgttctgctg gactgagctg gttgcctcat      60
gttattatgc aggcaactca ctttatccca atttcttgat acttttcctt ctggaggtcc     120
tatttctcta acatcttcca gaaaagtctt aaagctgcct taaccttttt tccagtccac     180
ctcttaaatt ttttcctcct cttcctctat actaacatga gtgtggatcc agcttgtccc     240
caaagcttgc cttgctttga agcatccgac tgtaaagaat cttcacctat gctgtgatt      300 tgtgggcctg aagaaaacta ccatccttgc aaatgtcttc tgctgagat gcctcacacg      360 gagactgtct ctcctcttcc ctcctccatg gatctgctta ttcaggacag ccctgattct     420
tccaccagtc ccaaaggcaa caacccact tctgcagaga atagtgtcgc aaaaaaggaa      480
gacaaggtcc cagtcaagaa acagaagacc agaactgtgt tctcttccac ccagctgtgt     540
gtactcaatg atagatttca gagacagaaa tacctcagcc tccagcagat gcaagaactc     600
tccaacatcc tgaacctcag ctacaaacag gtgaagacct ggttccagaa ccagagaatg     660
aaatctaaga ggtggcagaa aaacaactgg ccgaagaata gcaatggtgt gacgcagaag     720
gcctcagcac ctacctaccc cagcctctac tcttcctacc accagggatg cctggtgaac     780
```

```
ccgactggga accttccaat gtggagcaac cagacctgga caattcaac  ctggagcaac    840 cagacccaga acatccagtc ctggagcaac cactcctgga cactcagac  ctggtgcacc    900 caatcctgga caatcaggc  ctggaacagt cccttctata actgtggaga ggaatctctg    960
cagtcctgca tgcagttcca gccaaattct cctgccagtg acttggaggc tgctttggaa   1020
gctgctgggg aaggccttaa tgtaatacag cagaccacta ggtattttag tactccacaa   1080
accatggatt tattcctaaa ctactccatg aacatgcaac tgaagacgt  gtgaagatga   1140 gtgaaactga tattactcaa tttcagtctg gacactggct gaatccttcc tctcccctcc   1200
tcccatccct cataggattt tcttgtttg  gaaaccacgt gttctggttt ccatgatgcc   1260
tatccagtca atctcatgga gggtggagta tggttggagc taatcagcg  aggtttcttt   1320 ttttttttt  cctattggat cttcctggag aaaatacttt ttttttttt  tttgagacgg   1380 agtcttgctc tgtcgcccag gctggagtgc agtggcgcgg tcttggctca ctgcaagctc   1440
cgcctcccgg gttcacgcca ttctcctgcc tcagcctccc gagcagctgg gactacaggc   1500
gcccgccacc tcgcccggct aatattttgt attttagta  gagacagggt ttcactgtgt   1560
tagccaggat ggtctcgatc tcctgacctt gtgatccgcc cgcctcggcc tcctaacag   1620 ctgggattac aggcgtgagc caccgcgccc tgcctagaaa agacatttta ataaccttgg   1680
ctgctaagga caacattgat agaagccgtc tctggctata gataagtaga tctaatacta   1740
gtttggatat ctttagggtt tagaatctaa cctcaagaat aagaaataca agtacgaatt   1800
ggtgatgaag atgtattcgt attgtttggg attgggaggc tttgcttatt ttttaaaac    1860 tattgaggta aagggttaag ctgtaacata cttaattgat ttcttaccgt ttttggctct   1920
gttttgctat atcccctaat ttgttggttg tgctaatctt tgtagaaaga ggtcttgtat   1980
ttgctgcatc gtaatgacat gagtactact ttagttggtt taagttcaaa tgaatgaaac   2040
aaatattttt cctttagttg atttaccct  gatttcaccg agtgtttcga tgagtaaata   2100
tacagcttaa acat                                                     2114
```

<210> SEQ ID NO 4
<211> LENGTH: 305
<212> TYPE: PRT
<213> ORGANISM: Homo sapiens

<400> SEQUENCE: 4

```
Met Ser Val Asp Pro Ala Cys Pro Gln Ser Leu Pro Cys Phe Glu Ala
1               5                   10                  15

Ser Asp Cys Lys Glu Ser Ser Pro Met Pro Val Ile Cys Gly Pro Glu
            20                  25                  30

Glu Asn Tyr Pro Ser Leu Gln Met Ser Ser Ala Glu Met Pro His Thr
        35                  40                  45

Glu Thr Val Ser Pro Leu Pro Ser Ser Met Asp Leu Leu Ile Gln Asp
    50                  55                  60

Ser Pro Asp Ser Ser Thr Ser Pro Lys Gly Lys Gln Pro Thr Ser Ala
65                  70                  75                  80

Glu Asn Ser Val Ala Lys Lys Glu Asp Lys Val Pro Val Lys Lys Gln
                85                  90                  95

Lys Thr Arg Thr Val Phe Ser Ser Thr Gln Leu Cys Val Leu Asn Asp
            100                 105                 110

Arg Phe Gln Arg Gln Lys Tyr Leu Ser Leu Gln Gln Met Gln Glu Leu
        115                 120                 125
```

```
Ser Asn Ile Leu Asn Leu Ser Tyr Lys Gln Val Lys Thr Trp Phe Gln
        130                 135                 140

Asn Gln Arg Met Lys Ser Lys Arg Trp Gln Lys Asn Asn Trp Pro Lys
145                 150                 155                 160

Asn Ser Asn Gly Val Thr Gln Lys Ala Ser Ala Pro Thr Tyr Pro Ser
                165                 170                 175

Leu Tyr Ser Ser Tyr His Gln Gly Cys Leu Val Asn Pro Thr Gly Asn
            180                 185                 190

Leu Pro Met Trp Ser Asn Gln Thr Trp Asn Asn Ser Thr Trp Ser Asn
        195                 200                 205

Gln Thr Gln Asn Ile Gln Ser Trp Ser Asn His Ser Trp Asn Thr Gln
    210                 215                 220

Thr Trp Cys Thr Gln Ser Trp Asn Asn Gln Ala Trp Asn Ser Pro Phe
225                 230                 235                 240

Tyr Asn Cys Gly Glu Glu Ser Leu Gln Ser Cys Met Gln Phe Gln Pro
                245                 250                 255

Asn Ser Pro Ala Ser Asp Leu Glu Ala Ala Leu Glu Ala Ala Gly Glu
            260                 265                 270

Gly Leu Asn Val Ile Gln Gln Thr Thr Arg Tyr Phe Ser Thr Pro Gln
        275                 280                 285

Thr Met Asp Leu Phe Leu Asn Tyr Ser Met Asn Met Gln Pro Glu Asp
    290                 295                 300

Val
305

<210> SEQ ID NO 5
<211> LENGTH: 720
<212> TYPE: DNA
<213> ORGANISM: Rattus norvegicus

<400> SEQUENCE: 5
atgagcgtgg atctttctgg tccccacagt ctgcctagtt gtgaggaagc atcgaactct      60
ggggattcct cgccgatgcc tgccgttcat cttcctgagg aaaattattc ttgcttacaa     120
gtgtctgcta ctgagatgct ctgcacagag actgcctctc ctccgccttc ctctggggac     180
ctacctcttc aagatagccc tgattcttct agcaatccca agctaaagct gtctggtccc     240
gaggctgacg agggccctga agaaaagaa gagaacaagg tcctcaccaa gaagcagaag      300
atgcggactg tgttctctca ggcccagttg tgtgcactca aggataggtt tcagaggcaa     360
aggtacctca gcctccagca gatgcaagat ctctctacca ttctgaacct gagctataag     420
caggtgaaga cctggttcca aaaccaaaga atgaagtgca agaggtggca gaaaaaccaa     480
tggttgaaga ctagcaacgg cctgactcag gcctggaaca gccagacttg gaacgctgct     540
ccgctccata acttcgggga ggactccctg cagccttatg tgccgttgca gcaaaacttc     600
tccgccagtg atttggaggc gaatttggaa gccactaggg aaagccaggc gcattttagt     660
accccgcaag ccttggaatt gttcctgaac tactccgtga attctccagg cgaaatatga     720

<210> SEQ ID NO 6
<211> LENGTH: 239
<212> TYPE: PRT
<213> ORGANISM: Rattus norvegicus

<400> SEQUENCE: 6

Met Ser Val Asp Leu Ser Gly Pro His Ser Leu Pro Ser Cys Glu Glu
1               5                   10                  15
```

```
Ala Ser Asn Ser Gly Asp Ser Ser Pro Met Pro Ala Val His Leu Asp
            20                  25                  30

Glu Glu Asn Tyr Ser Cys Leu Gln Val Ser Ala Thr Glu Met Leu Cys
                35                  40                  45

Thr Glu Thr Ala Ser Pro Pro Ser Ser Gly Asp Leu Pro Leu Gln
 50                  55                  60

Asp Ser Pro Asp Ser Ser Asn Pro Lys Leu Lys Leu Ser Gly Pro
 65                  70                  75                  80

Glu Ala Asp Glu Gly Pro Glu Lys Lys Glu Asn Lys Val Leu Thr
                 85                  90                  95

Lys Lys Gln Lys Met Arg Thr Val Phe Ser Gln Ala Gln Leu Cys Ala
            100                 105                 110

Leu Lys Asp Arg Phe Gln Arg Gln Arg Tyr Leu Ser Leu Gln Gln Met
            115                 120                 125

Gln Asp Leu Ser Thr Ile Leu Asn Leu Ser Tyr Lys Gln Val Lys Thr
130                 135                 140

Trp Phe Gln Asn Gln Arg Met Lys Cys Lys Arg Trp Gln Lys Asn Gln
145                 150                 155                 160

Trp Leu Lys Thr Ser Asn Gly Leu Thr Gln Ala Trp Asn Ser Gln Thr
                165                 170                 175

Trp Asn Ala Ala Pro Leu His Asn Phe Gly Glu Asp Ser Leu Gln Pro
            180                 185                 190

Tyr Val Pro Leu Gln Gln Asn Phe Ser Ala Ser Asp Leu Glu Ala Asn
            195                 200                 205

Leu Glu Ala Thr Arg Glu Ser Gln Ala His Phe Ser Thr Pro Gln Ala
    210                 215                 220

Leu Glu Leu Phe Leu Asn Tyr Ser Val Asn Ser Pro Gly Glu Ile
225                 230                 235

<210> SEQ ID NO 7
<211> LENGTH: 3108
<212> TYPE: DNA
<213> ORGANISM: Macaca fascicularis

<400> SEQUENCE: 7
cttgggtttg ccacagtctc ttcacttacc tccttgttcc gtttatctcc ttcaccagca      60
gcacatctcc atgaatgctg ccagggtcat ctttatgccc tattttatca tgactattaa     120
ctctgactaa tatttcttta agttggttg tagatgttta ctacaaatat ttctctgtga      180
cattaacaga tgtggtaagg tcgttgtcga cattgtattc ccagtaattt aggatttttt     240
tctatctctg ataatgaaga ataatgata gagtaggtaa attccaacat taacaacaac      300
aagaaaataa tgaactagat tttgatatac taacacagaa tgttcttcca gctatattgt     360
taagccaaca agtatacat aacgtacaag tatatgaatg taaatgcact aaaagaaaat      420
atttgaaagt gtatacacca ataaacaga ctttacctct cggaagaaaa tagtgtggta      480
ggcgaaagca taagaggga actttagttt ttactttcca tagtttagta ttatttactt     540
tttaaaaaaa ccacaggcac gtatttgtat tttattcttt aatttaagaa acctaaaggg     600
tttccttggc gaagaatgtg aaacacacac acacacacac acaagatggg cacggagtag     660
tcttgaaaga catgacaata tcaccagacc tgaagaaag ctaaagagcc agagggaaaa      720
agtcagaagt cgactacctg ggaggaggga tagacaagag accaaactaa ggaaactaa      780 gtgtggatcc agcttgtccc caaagcttgc cttgcttcaa agcatcagat ggtaaagaat      840
cttcacctgt gcctgtgatt tgtgggcctg aagaaaacta tccatccttg caaatgtctt      900
```

```
ctactgagat gcctcacacg gagactgtct ctcctcttcc ttcctccatg gatctgctta      960
ttcaggacag ccccgattct tccaccagtc ccaaaggcag acaacctact gctgcagaga     1020
atagtgccac aaaaaaggaa gacaaggtcc cggtcaagaa acagaaggcc agaactgtgt     1080
tctcttccgc ccagctgtgt gtactcaatg atagatttca gagacagaga tacctcagcc     1140
tccagcagat gcaagaactt tccaacatcc tgaacctccg ctacaaacag gtgaagacct     1200
ggttccagaa ccagagaatg aaatccaaga ggtggctgaa aaacaactgg ccaaagaata     1260
ccaatggtgt gactcagaag gcttcagcgc ctacctaccc cagccactac tcttcctact     1320
accagggatg cctggtgaac ccgactggga atcttccgat gtggaggaac cagacctgga     1380
acaattcatc ctggagcaac cagagccaga acgtcccacc ctggagcagc cactcctgga     1440
acgctcagac ctggtgcacc cagttctgga acaatcaggc ctggaacagt cccttctatg     1500
actatgaagg ggaatctcta cagtcctgct tgcagttcca gccaaattct cctgccagtg     1560
acttggaggc tgccttggaa gctgctgggg aaggccttaa tgtaatacag cagacgacta     1620
ggtattttag tactccacaa accatggatt tattcctaaa ctactccacg aacgtgcaac     1680
ctgaagatat gtaaagatga gtaaaattga tattactcaa tttcagtctg ggcactggct     1740
gaaccttcct ctcccctcct cccctcccta taggattttt cttgtttgga aaccacgtgt     1800
tctggtttcc attatgtcta tccagtcaat ttgatggagg gtggagtatg gttggagcct     1860
aatcagagag gtttcttttt ttcctattgg atcttcctgg agaaaagaca ttttaataac     1920
tttggctgct aaggacaaca tgataaaagc tgtctctggc tatagataag tagatctaat     1980
actagtttgg atatctttag tgtttagaat ctaacctcaa gaataagaaa tacaagtaca     2040
aattggtgtt atgaagatac tcctattgtt tgggattttg aggctttgct tatttttaa      2100 aaactattga ggtaaacggt taattgattt cctcacccct tttggctcag ttttactata     2160 tccccctaatt tgttggttat gctaatcttt gtagaaagag gtcttatatt tgctgcatca     2220
taatgatgtt agtactactt tagtcaattt aagtacaaat gaatcaaaca actattttc      2280 ctttagttga ttttaccctt attttaccta gtgtttcaaa tatacagctt aaacattaaa     2340
aaaaaaaaaa aaaaaagaa agaaagaaag aaacctaaag gaagtttgct tttttgagat      2400
taaaatgtat ttaggcatgt aggttttgc agaatagcaa gtcaccaacc aagggccctt      2460
tatttccaca tagaaaggta agaacatcaa gctatgtgaa gagtgaacaa tatcaatcat     2520
tgcaacttct aatattaagg gtagatttgc atgtaaattt ggttacttct aatgatatag     2580
gttgtcaaac acttaataaa aatgaactat tttgttaatg gcataaattc cctcatcgtt     2640
ggatataagc tttatcttaa atattatgta gaaacttaca aatgctagtc agtttcttag     2700
cctttttttg aaaaaaattt aaagtggttt agtaaatggt aaatgcaggt tggcattaat     2760
gatgtaataa ttcttaaagt gactgtctta aaaaatgtaa aagtagaccg ggcatggtgg     2820
ctcatgtctg taatcccagc agtttgggag gctgaggtgg gcacgtcacc tgaggtcagg     2880
agtttgagac cagcctggcc aacatggtga accccatct ctacaaaaat acaaaaatta      2940
gccaggcatg atggcaggtg cctgtaatcc cagctactcg ggaggttgag gcaggagaat     3000
tgcttgaatc caggaggcag aggttgcagt gagccgagat tgcaccattg cactccagcc     3060
tgggtgacag agcgagactc cagcttaaaa aaaaaaaaa aaaaaaa                    3108

<210> SEQ ID NO 8
<211> LENGTH: 266
<212> TYPE: PRT
```

<213> ORGANISM: Macaca fascicularis

<400> SEQUENCE: 8

Met Ser Ser Thr Glu Met Pro His Thr Glu Thr Val Ser Pro Leu Pro
1               5                   10                  15

Ser Ser Met Asp Leu Leu Ile Gln Asp Ser Pro Asp Ser Ser Thr Ser
            20                  25                  30

Pro Lys Gly Arg Gln Pro Thr Ala Ala Glu Asn Ser Ala Thr Lys Lys
        35                  40                  45

Glu Asp Lys Val Pro Val Lys Lys Gln Lys Ala Arg Thr Val Phe Ser
50                  55                  60

Ser Ala Gln Leu Cys Val Leu Asn Asp Arg Phe Gln Arg Gln Arg Thr
65                  70                  75                  80

Leu Ser Leu Gln Gln Met Gln Glu Leu Ser Asn Ile Leu Asn Leu Arg
                85                  90                  95

Tyr Lys Gln Val Lys Thr Trp Phe Gln Asn Gln Arg Met Lys Ser Lys
            100                 105                 110

Arg Trp Leu Lys Asn Asn Trp Pro Lys Asn Thr Asn Gly Val Thr Gln
        115                 120                 125

Lys Ala Ser Ala Pro Thr Trp Pro Ser His Tyr Ser Ser Tyr Tyr Gln
130                 135                 140

Gly Cys Leu Val Asn Pro Thr Gly Asn Leu Pro Met Trp Arg Asn Gln
145                 150                 155                 160

Thr Trp Asn Asn Ser Ser Trp Ser Asn Gln Ser Gln Asn Val Pro Pro
                165                 170                 175

Trp Ser Ser His Ser Trp Asn Ala Gln Thr Trp Cys Thr Gln Phe Trp
            180                 185                 190

Asn Asn Gln Ala Trp Asn Ser Pro Phe Tyr Asp Thr Glu Gly Glu Ser
        195                 200                 205

Leu Gln Ser Cys Leu Gln Phe Gln Pro Asn Ser Pro Ala Ser Asp Leu
210                 215                 220

Glu Ala Ala Leu Glu Ala Ala Gly Glu Gly Leu Asn Val Ile Gln Gln
225                 230                 235                 240

Thr Thr Arg Tyr Phe Ser Thr Tyr Ser Thr Asn Val Gln Pro Glu Asp
                245                 250                 255

Met Pro Gln Thr Met Asp Leu Phe Leu Asn
            260                 265

<210> SEQ ID NO 9
<211> LENGTH: 11
<212> TYPE: PRT
<213> ORGANISM: Mus musculus
<220> FEATURE:
<221> NAME/KEY: Xaa
<222> LOCATION: (2)..(2)
<223> OTHER INFORMATION: Xaa is G,S,N
<220> FEATURE:
<221> NAME/KEY: Xaa
<222> LOCATION: (3)..(3)
<223> OTHER INFORMATION: Xaa is S,N

<400> SEQUENCE: 9

Trp Xaa Xaa Gln Thr Trp Thr Asn Pro Thr Trp
1               5                   10

<210> SEQ ID NO 10
<211> LENGTH: 60
<212> TYPE: PRT
<213> ORGANISM: Mus musculus

<400> SEQUENCE: 10

Lys Gln Lys Met Arg Thr Val Phe Ser Gln Ala Gln Leu Cys Ala Leu
1               5                   10                  15
Lys Asp Arg Phe Gln Lys Gln Lys Tyr Leu Ser Leu Gln Met Gln
            20                  25                  30
Glu Leu Ser Ser Ile Leu Asn Leu Ser Tyr Lys Gln Val Lys Thr Trp
        35                  40                  45
Phe Gln Asn Gln Arg Met Lys Cys Lys Arg Trp Gln
    50                  55                  60

<210> SEQ ID NO 11
<211> LENGTH: 60
<212> TYPE: PRT
<213> ORGANISM: Mus musculus

<400> SEQUENCE: 11

Arg Arg Lys Pro Arg Val Leu Phe Ser Gln Ala Gln Val Tyr Glu Leu
1               5                   10                  15
Glu Arg Arg Phe Lys Gln Gln Arg Tyr Leu Ser Ala Pro Glu Arg Asp
            20                  25                  30
Gln Leu Ala Ser Val Leu Lys Leu Thr Ser Thr Gln Val Lys Ile Trp
        35                  40                  45
Phe Gln Asn Arg Arg Tyr Lys Cys Lys Arg Gln Arg
    50                  55                  60

<210> SEQ ID NO 12
<211> LENGTH: 60
<212> TYPE: PRT
<213> ORGANISM: Mus musculus

<400> SEQUENCE: 12

Gly Arg Arg Ser Arg Thr Val Phe Thr Glu Leu Gln Leu Met Gly Leu
1               5                   10                  15
Glu Lys Arg Phe Glu Lys Gln Lys Tyr Leu Ser Thr Pro Asp Arg Ile
            20                  25                  30
Asp Leu Ala Glu Ser Leu Gly Leu Ser Gln Leu Gln Val Lys Thr Trp
        35                  40                  45
Tyr Gln Asn Arg Arg Met Lys Trp Lys Lys Ile Val
    50                  55                  60

<210> SEQ ID NO 13
<211> LENGTH: 60
<212> TYPE: PRT
<213> ORGANISM: Mus musculus

<400> SEQUENCE: 13

Asn Arg Lys Pro Arg Thr Pro Phe Thr Thr Ala Gln Leu Leu Ala Leu
1               5                   10                  15
Glu Arg Lys Phe Arg Gln Lys Gln Tyr Leu Ser Ile Ala Glu Arg Ala
            20                  25                  30
Glu Phe Ser Ser Ser Leu Ser Leu Thr Glu Thr Gln Val Lys Ile Trp
        35                  40                  45
Phe Gln Asn Arg Arg Ala Lys Ala Lys Arg Leu Gln
    50                  55                  60

<210> SEQ ID NO 14
<211> LENGTH: 60
<212> TYPE: PRT

<213> ORGANISM: Mus musculus

<400> SEQUENCE: 14

Arg Arg Lys Arg Arg Val Leu Phe Ser Gln Ala Gln Val Tyr Glu Leu
1               5                   10                  15

Glu Arg Arg Phe Lys Gln Gln Lys Tyr Leu Ser Ala Pro Glu Arg Glu
            20                  25                  30

His Leu Ala Ser Met Ile His Leu Thr Pro Thr Gln Val Lys Ile Trp
        35                  40                  45

Phe Gln Asn His Arg Tyr Lys Met Lys Arg Gln Ala
    50                  55                  60

<210> SEQ ID NO 15
<211> LENGTH: 60
<212> TYPE: PRT
<213> ORGANISM: Mus musculus

<400> SEQUENCE: 15

Lys Lys Lys Thr Arg Thr Val Phe Ser Arg Ser Gln Val Tyr Gln Leu
1               5                   10                  15

Glu Ser Thr Phe Asp Met Lys Arg Tyr Leu Ser Ser Ser Glu Arg Ala
            20                  25                  30

Cys Leu Ala Ser Ser Leu Gln Leu Thr Glu Thr Gln Val Lys Thr Trp
        35                  40                  45

Phe Gln Asn Arg Arg Asn Lys Trp Lys Arg Gln Leu
    50                  55                  60

<210> SEQ ID NO 16
<211> LENGTH: 60
<212> TYPE: PRT
<213> ORGANISM: Mus musculus

<400> SEQUENCE: 16

Lys Lys Arg Ser Arg Ala Ala Phe Ser His Ala Gln Val Phe Glu Leu
1               5                   10                  15

Glu Arg Arg Phe Asn His Gln Arg Tyr Leu Ser Gly Pro Glu Arg Ala
            20                  25                  30

Asp Leu Ala Ala Ser Leu Lys Leu Thr Glu Thr Gln Val Lys Ile Trp
        35                  40                  45

Phe Gln Asn Arg Arg Tyr Lys Thr Lys Arg Arg Gln
    50                  55                  60

<210> SEQ ID NO 17
<211> LENGTH: 60
<212> TYPE: PRT
<213> ORGANISM: Mus musculus

<400> SEQUENCE: 17

Ile Arg Lys Pro Arg Thr Ile Tyr Ser Ser Leu Gln Leu Gln Ala Leu
1               5                   10                  15

Asn Arg Arg Phe Gln Gln Thr Gln Tyr Leu Ala Leu Pro Glu Arg Ala
            20                  25                  30

Glu Leu Ala Ala Ser Leu Gly Leu Thr Gln Thr Gln Val Lys Ile Trp
        35                  40                  45

Phe Gln Asn Lys Arg Ser Lys Phe Lys Lys Leu Met
    50                  55                  60

<210> SEQ ID NO 18
<211> LENGTH: 60

```
<212> TYPE: PRT
<213> ORGANISM: Mus musculus

<400> SEQUENCE: 18

Lys Lys Lys Pro Arg Thr Ser Phe Thr Arg Leu Gln Ile Cys Glu Leu
1               5                   10                  15

Glu Lys Arg Phe His Arg Gln Lys Tyr Leu Ala Ser Ala Glu Arg Ala
            20                  25                  30

Ala Leu Ala Lys Ala Leu Lys Met Thr Asp Ala Gln Val Lys Thr Trp
        35                  40                  45

Phe Gln Asn Arg Arg Thr Lys Trp Arg Arg Gln Thr
    50                  55                  60

<210> SEQ ID NO 19
<211> LENGTH: 60
<212> TYPE: PRT
<213> ORGANISM: Mus musculus

<400> SEQUENCE: 19

Arg Arg Lys Ser Arg Thr Ala Phe Thr Asn His Gln Ile Tyr Glu Leu
1               5                   10                  15

Glu Lys Arg Phe Leu Tyr Gln Lys Tyr Leu Ser Pro Ala Asp Arg Asp
            20                  25                  30

Gln Ile Ala Gln Gln Leu Gly Leu Thr Asn Ala Gln Val Ile Thr Trp
        35                  40                  45

Phe Gln Asn Arg Arg Ala Lys Leu Lys Arg Asp Leu
    50                  55                  60

<210> SEQ ID NO 20
<211> LENGTH: 60
<212> TYPE: PRT
<213> ORGANISM: Mus musculus

<400> SEQUENCE: 20

Pro Lys Arg Thr Arg Thr Ser Phe Thr Ala Glu Gln Leu Tyr Arg Leu
1               5                   10                  15

Glu Met Glu Phe Gln Arg Cys Gln Tyr Val Val Gly Arg Glu Arg Thr
            20                  25                  30

Glu Leu Ala Arg Gln Leu Asn Leu Ser Glu Thr Gln Val Lys Val Trp
        35                  40                  45

Phe Gln Asn Arg Arg Thr Lys Gln Lys Lys Asp Gln
    50                  55                  60

<210> SEQ ID NO 21
<211> LENGTH: 60
<212> TYPE: PRT
<213> ORGANISM: Mus musculus

<400> SEQUENCE: 21

Pro Lys Arg Ile Arg Thr Ala Phe Ser Pro Ser Gln Leu Leu Arg Leu
1               5                   10                  15

Glu Arg Ala Phe Glu Lys Asn His Tyr Val Val Gly Ala Glu Arg Lys
            20                  25                  30

Gln Leu Ala Gly Ser Leu Ser Leu Ser Glu Thr Gln Val Lys Val Trp
        35                  40                  45

Phe Gln Asn Arg Arg Thr Lys Tyr Lys Arg Gln Lys
    50                  55                  60

<210> SEQ ID NO 22
```

```
<211> LENGTH: 60
<212> TYPE: PRT
<213> ORGANISM: Mus musculus

<400> SEQUENCE: 22

Pro Arg Arg Ala Arg Thr Ala Phe Thr Tyr Glu Gln Leu Val Ala Leu
1               5                   10                  15

Glu Asn Lys Phe Arg Ala Thr Arg Tyr Leu Ser Val Cys Glu Arg Leu
            20                  25                  30

Asn Leu Ala Leu Ser Leu Ser Leu Thr Glu Thr Gln Val Lys Ile Trp
        35                  40                  45

Phe Gln Asn Arg Arg Thr Lys Trp Lys Lys Gln Asn
    50                  55                  60

<210> SEQ ID NO 23
<211> LENGTH: 60
<212> TYPE: PRT
<213> ORGANISM: Mus musculus

<400> SEQUENCE: 23

Arg Lys His Thr Arg Pro Thr Phe Ser Gly Gln Gln Ile Phe Ala Leu
1               5                   10                  15

Glu Lys Thr Phe Glu Gln Thr Lys Tyr Leu Ala Gly Pro Glu Arg Ala
            20                  25                  30

Arg Leu Ala Tyr Ser Leu Gly Met Thr Glu Ser Gln Val Lys Val Trp
        35                  40                  45

Phe Gln Asn Arg Arg Thr Lys Trp Arg Lys Lys His
    50                  55                  60

<210> SEQ ID NO 24
<211> LENGTH: 194
<212> TYPE: DNA
<213> ORGANISM: Mus musculus

<400> SEQUENCE: 24
ggggctggtg agatggctca gtggacaaga gcacccgact gctcttccga aggtcaggag    60
ctcaaatccc agcaaccaca cggcggctca caaccatacg caacaagatc tgacgccctc   120
ctctggagtg tccgaagaca gccacagtgt actcacacat aatgaacaaa taatctttta   180
aaaaaaatat gaaa                                                     194

<210> SEQ ID NO 25
<211> LENGTH: 196
<212> TYPE: DNA
<213> ORGANISM: Mus musculus

<400> SEQUENCE: 25
ggggctggag agatggctca gcggttaaga gcactgactg ctcttccgaa ggtcctgagt    60
tcaattcccg caaccacat ggtggctcac aaccatccgt aatgagatct ggtgccctct   120
tctggagtgt ctgaggacag ctacagtgta cttacatata taaataaat aaaaatctt   180 ttaaaaaaaa aaaaaa                                                   196
```

PLURIPOTENCY DETERMINING FACTORS AND USES THEREOF

This application is a 371 of International Application No. PCT/GB03/00366, filed Jan. 30, 2003, which claims priority to foreign application GB 0202149.1, filed Jan. 30, 2002, the contents of which are incorporated herein by reference.

The present invention relates to pluripotency determining factors and their uses. In particular the invention relates to maintaining and deriving cultures of pluripotent cells of mouse, human and other species.

From certain strains of mouse, embryonic stem (ES) cells may be derived and maintained in a pluripotent state in culture by provision of a cytokine that activates signal transduction through the LIF-receptor/gp130 complex. This approach is, however, limited to mice and is not sufficient for propagation of human pluripotent cells.

The discovery of the extracellular activity ESRF (Dani et al, 1998) has provided evidence for a LIF-receptor/gp130-independent pathway for maintaining ES cell identity. However, ESRF is incompletely characterised and the molecular nature of extracellular regulators other than gp130 cytokines is unknown.

In addition, the transcriptional determination of pluripotency is not fully understood. Important roles have been assigned to the gp130 target STAT3 and the POU factor Oct-4, but neither of these alone is sufficient to specify ES cell identity.

WO 02/097090 describes the identification of ECAT (ES cell associated transcript) genes by interrogating nucleotide sequence databases, and subsequent analysis of the expression pattern of murine and human ECAT genes. WO 02/097090 also describes the use of probes to identify ES cells and selective isolation of ES cells using ECAT genes. Oct-4 is an ECAT gene and a specific marker of pluripotent cells, though is expressed also in oocytes, cleavage embryos and egg cylinder stages. WO 01/66697 describes culture of ES cells in medium free of animal serum and in the presence of fibroblast growth factor. Preferably the ES cells are grown in the presence of a fibroblast feeder layer.

WO 97/30151, in the name of the present applicants, describes ESRF, a cytokine capable of inhibiting differentiation of ES cells.

WO 96/22693 relates to the maintenance of self-renewing haematopoietic stem cells. In particular, WO 96/22693 describes an "F factor" capable of maintaining haematopoietic stem cells in an undifferentiated state and supporting proliferation of undifferentiated haematopoietic stem cells.

Berger C. N. and Sturm K. S., Growth Factors 1997, Volume 14, pages 145-159, describes self-renewal of ES cells in the absence of exogenous LIF and feeder cells. Berger and Sturm do not, however, describe the isolation of any factor able to promote self-renewal of ES cells under these conditions.

Genbank Accession Numbers AK010332, 2001, and AK022643, 2000, provide sequences of mouse and human cDNAs for homeobox domain containing proteins. No function is ascribed to these molecules.

It is known that pluripotency of human embryonic stem cells and embryonic germ cells is sustained by co-culture with a feeder layer of heterologous cells (Amit et al, Dev. Biol. 2000) or extracts therefrom (Xu et al. Nat. Biotech 2001). However, dependency on feeder cells gives rise to a number of problems. Co-culture of feeder cells and pluripotent cells may mask compromised culture conditions. Co-culture risks contamination of the pluripotent culture/differentiated product derived therefrom. To produce feeder cell extract, which is an alternative to using the cells, a separate feeder cell population must be maintained and processed, and the extract stored. As the extract is uncharacterised, it represents another source of contamination of the product. Analysis and manipulation of differentiation of pluripotent cells is compromised by the presence of feeder cells or undefined extracts.

In relation to many other species, in particular porcine, bovine and rat, it is still not possible to derive and stably maintain pluripotent ES cells in culture.

An object of the present invention is to provide improved culture of mouse and human pluripotent cells, and an object of specific embodiments of the invention is to remove the dependency on feeder cells in pluripotent cell culture. A further object is to provide for derivation and maintenance of pluripotent cells from other species.

Accordingly, the present invention provides mammalian pluripotency determining factors, exemplified in a first embodiment by a factor that maintains pluripotency in a mammalian cell.

In a culture of ES cells, the factor has been found to be sufficient to confer pluripotency of those cells. According to the invention, the factor may be maintained in a pluripotent cell at a level that results in maintenance of a self-renewing pluripotent phenotype. The factor may be endogenous—a cellular level of the factor being maintained by activation of an endogenous gene—or introduced into the cell so as to enable stable maintenance of the pluripotent phenotype of the cells.

A particular factor of the invention acts intracellularly, maintains a cell in a pluripotent state and, in cell culture, is constitutively active. In this context, reference to intracellular action indicates that the site of activity lies within the cell. The factor is thus not, for example, a ligand for a cell surface receptor, as is the case with LIF and other cytokines, and it can act independently of signalling from gp130 receptors.

Further pluripotency determining factors of the invention maintain pluripotent cells, cultured in ES cell medium lacking gp130 activators, in a pluripotent state. Thus, the factor is able to maintain a mammalian cell in a pluripotent state in the absence of gp130 activation and can promote maintenance of pluripotency in culture medium lacking cytokines that activate gp130-receptor complexes. In examples below we have demonstrated that cells expressing preferred factors of the invention are liberated from the requirement for gp130 stimulation and show reduced or absent differentiation in response to retinoic acid, 3-methoxybenzamide and aggregation—hence their differentiation is suppressed in response to these stimuli. The factor of specific examples is, further, not a downstream transcriptional target of gp130. The factors of the invention have been isolated and are suitable for maintenance of animal pluripotent cells, animal cells including those of mouse, human, primate, sheep, rat, pig, cow and other animals. One factor of the invention maintains pluripotency of a human ES, EC or EG cell or other human pluripotent cell. Another factor of the invention maintains pluripotency of a mouse ES, EC or EG cell and acts intracellularly and is constitutively active. A further factor of the invention allows the continuous propagation in culture of pluripotent cells from non-permissive strains of mice.

An advantage of the invention lies in the ability to stably proliferate pluripotent cells in culture. Factors of the invention can be used in cultures to maintain human and/or mouse cells in a proliferative, pluripotent state. The invention further offers the possibility to isolate and maintain ES cells from species other than human and mouse—not possible hitherto.

A factor of a specific embodiment is a transcription factor. It acts inside the nucleus, resulting in self-renewal of the ES cell. A preferred factor, described and used in an example below, contains a homeodomain In use of one factor of the invention, the factor maintains cells in a pluripotent state in the absence of a feeder layer or a feeder cell extract and in the absence of a gp130 cytokine. Thus, supply of the factor is sufficient to maintain pluripotency of cells in culture. The factor can be added to standard ES cell culture medium or introduced directly into cells, for example by electroporation or microinjection, or produced in the cell by a variety of methods disclosed herein. In specific examples of the invention, described in more detail below, vectors that express the factor support cytokine independent ES cell propagation both via episomal transfection of cells and upon chromosomal integration into cells; a further option, not specifically exemplified, is for expression of an endogenous sequence encoding the factor to be induced or increased so as to enable ES cell self renewal.

In a further embodiment of the invention, the factor is identifiable by its property of maintaining LIF non-responsive cells in a pluripotent state.

The factor suitably is a polypeptide having from 200 to 400 amino acids. Specifically, a mouse pluripotency determining factor of the invention is represented by SEQ ID NO 2, a human pluripotency determining factor by SEQ ID NO 4, a rat pluripotency determining factor by SEQ ID NO 6, and a macaque pluripotency determining factor by SEQ ID NO 8.

A second aspect of the invention lies in a factor which maintains a cell in a pluripotent state, acts intracellularly and comprises a homeodomain, in particular a homeodomain that has at least 50% sequence identity with the homeodomain from SEQ ID NO: 2, 4, 6 or 8 or, in relation to a factor for cells of a given species, one that has at least 50% sequence identity with the homeodomain of pluripotency determining factor of the same species. Generally, a homeodomain is around 60 amino acids in length and the factor of the invention comprises a homeodomain in which any 20 amino acid fragment has at least 35% sequence identity with the homeodomain of SEQ ID NO: 2, 4, 6 or 8. Preferably, the factor maintains LIF non-responsive cells in a pluripotent state.

A factor of a further embodiment is one which maintains cultured epiblast cells from non-permissive strains of mice in a pluripotent state in the absence of feeder cells and in the absence of feeder cell extract. A second such factor is one that maintains human embryo-derived cells (including ES and EG cells) in a pluripotent state in the absence of feeder cells and in the absence of feeder cell extract.

The avoidance of feeder cells or feeder cell extracts has the benefit of reducing contamination of the culture by unwanted cells. Mouse cells have been used as feeder cells for human pluripotent cell cultures, and so the invention significantly reduces and may eliminate the risk of contamination of the human pluripotent cell population by non-human cells. If ES cell derived products are to be used in transplantation therapies, a guarantee of absence of non-human cells is likely to be essential, both for initial isolation of cells and also for subsequent propagation.

Also provided by the invention are conjugates of the factor with another functional domain. A first such conjugate comprises first and second domains, wherein the first domain comprises a factor of the invention and the second domain promotes uptake of the first domain into a cell e.g. protein transduction domains of antennapedia, HIV-1 TAT protein or HSV-1 VP22 (Schwarze et al., 2000). Hence, the conjugate can be used as a culture medium component. It is further optional for the second domain to include a nuclear localization sequence to assist in trafficking the factor to the nucleus after uptake into a cell.

To enable release of the first domain from the second in use, the first domain of a preferred conjugate may be cleaved from the second domain inside the cell. The first domain may be linked to the second domain by a di-sulphide bridge—which allows release of the first domain in the reducing environment of the cell. The first domain may be linked to the second domain covalently, allowing the link to be cleaved by a protease present in the cell. It is further optional for the second domain to comprise sequence permitting regulation of the activity of the factor, for example a steroid hormone receptor (Picard, 2000).

Further isolated polypeptides of the invention include (a) polypeptide molecules comprising an amino acid sequence as set out in SEQ ID NO: 2, 4, 6 or 8; (b) naturally occurring variants of (a); (c) orthologues of (a) or (b), and (d) biologically active and diagnostically or therapeutically useful fragments, analogues and derivatives thereof.

The polypeptide of the present invention may be a recombinant polypeptide, a natural polypeptide or a synthetic polypeptide, preferably a recombinant polypeptide.

The terms "fragment", "derivative" and "analogue" when referring to the polypeptide of the invention mean a polypeptide which retains essentially the same biological function or activity as such polypeptide. The fragment, derivative or analogue of the polypeptide of the invention may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, for example to facilitate purification of the mature polypeptide. Such fragments, derivatives and analogues are deemed to be within the scope of those skilled in the art from the teachings herein.

The polypeptides of the invention can also be used to prepare antibodies that specifically bind to pluripotency determining factor epitopes, peptides or polypeptides. Methods for preparing polyclonal and monoclonal antibodies are well known in the art (see, for example, Harlow and Lane, Using Antibodies: A Laboratory Manual, Cold Spring Harbor, N.Y., 1999; and Hurrell, J. G. R., Ed., Monoclonal Hybridoma Antibodies: Techniques and Applications, CRC Press, Inc., Boca Raton, Fla., 1982, which are incorporated herein by reference). Polyclonal antibodies can be generated from a variety of animals, such as horses, cows, goats, sheep, dogs, chickens, rabbits, mice, and rats.

The immunogenicity of a pluripotency determining factor polypeptide may be increased through the use of an adjuvant, such as alum (aluminium hydroxide) or Freund's complete or incomplete adjuvant. Polypeptides useful for immunization also include fusion polypeptides, such as fusions of pluripotency determining factor or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

As used herein, the term "antibodies" includes polyclonal antibodies, affinity-purified polyclonal antibodies, monoclonal antibodies, and antigen-binding fragments, such as F(ab')$_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting only non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced. Alternative techniques for generating or selecting antibodies useful herein include in vitro exposure of lymphocytes to pluripotency determining factor protein or peptide, and selection of antibody display libraries in phage or similar vectors (for instance, through use of immobilized or labelled pluripotency determining factor protein or peptide).

Antibodies are defined to be specifically binding if they bind to a pluripotency determining factor polypeptide with a binding affinity ($K_a$) of $10^6$ $M^{-1}$ or greater, preferably $10^7$ $M^{-1}$ or greater, more preferably $10^8$ $M^{-1}$ or greater, and most preferably $10^9$ $M^{-1}$ or greater. The binding affinity of an antibody can be readily determined by known techniques (for example, by Scatchard analysis).

A variety of assays known to those skilled in the art can be utilized to detect antibodies which specifically bind to pluripotency determining factor proteins or peptides. Exemplary assays are described in detail in Using Antibodies: A Laboratory Manual, Harlow and Lane (Eds.), Cold Spring Harbor Laboratory Press, 1999. Representative examples of such assays include: concurrent immunoelectrophoresis, radioimmunoassay, radioimmuno-precipitation, enzyme-linked immunosorbent assay (ELISA), dot blot or Western blot assay, inhibition or competition assay, and sandwich assay. In addition, antibodies can be screened for binding to wild-type versus mutant pluripotency determining factor protein or peptide.

The polypeptides of the present invention additionally include the polypeptides of SEQ ID NO: 2, 4, 6 and 8 (in particular the mature polypeptide) as well as polypeptides which have at least 50% similarity (preferably at least 50% identity) to the polypeptide of SEQ ID NO: 2, 4, 6 or 8 and more preferably at least 90% similarity (more preferably at least 90% identity) to the polypeptide of SEQ ID NO: 2, 4, 6 or 8 and still more preferably at least 95% similarity (still more preferably at least 95% identity) to the polypeptide of SEQ ID NO: 2, 4, 6 or 8 and also include portions of such polypeptides with such portion of the polypeptide generally containing at least 30 amino acids and more preferably at least 50 amino acids. "Similarity" between two polypeptides is determined by comparing the amino acid sequence and its conserved amino acid substitutes of one polypeptide to the sequence of a second polypeptide. Various different approaches are known for the calculation of sequence similarity and identity. Generally, a suitable way to perform these calculations is to run database searches using a program such as Smith-Waterman, BLAST or FASTA, and use one or preferably two or even three similarity tables. The Blosum and PAM (Point Accepted Mutation) matrices are suitable amino acids similarity matrices for database searching and sequence alignment. If Smith-Waterman or FASTA is used then it is relevant to ensure the open gap penalty is large enough, and if the initial runs do not uncover any homologous sequences it can be appropriate to try a different algorithm—this is particularly true if you started with one of the heuristic algorithms, BLAST or FASTA.

A yet further aspect of the invention lies in compositions containing the factor or the conjugate, and include a pharmaceutical composition comprising the factor or conjugate as described together with a pharmaceutically acceptable carrier; and a cell culture medium comprising the factor or conjugate as described.

Cell culture medium, containing a factor and/or a conjugate of the invention may additionally contain one or more components selected from the groups consisting of GMEM, serum, serum replacement, essential amino acids, β-mercaptoethanol, pyruvate and glutamine.

The culture medium optionally further contains an activator of gp130, and suitable activators include cytokines that act at the LIF receptor, e.g. LIF, and IL-6 in combination with soluble IL-6 receptor. The culture medium can be used for maintenance of pluripotent ES cells, especially ES, EC and EG cells and for self-renewal of pluripotent cells, especially ES, EC and EG cells. The medium can further be used for maintenance of somatic cells, especially somatic stem cells, and in a particular embodiment of the invention there is provided a method of self-renewal of somatic cells comprising culturing the cells in the presence of the medium and preferably propagating the cells in the medium. A still further use of the culture medium is for maintenance and/or propagation of cells derived from pluripotent cells.

Another application of the invention lies in expansion of cell populations, for example in expansion of somatic cells. An ex vivo therapy that can be carried out exploiting the invention comprises removing a population of cells from a patient, culturing the cells in culture medium of the invention so as to expand the cell population and thereafter transplanting or reintroducing the cells into the patient.

Further culture methods of the invention comprise maintaining and/or propagating cells using a combination of a factor of the invention and expression of Oct-4 and/or activation of Oct-4. The factor can be introduced as the factor per se or via a conjugate or using vectors as herein described. Oct-4 expression can be achieved by upregulating expression of an endogenous Oct-4 gene or by introducing an expression vector comprising Oct-4 into the cells. A combination of the factor of the invention and Oct-4 can be used to maintain and/or self-renew and/or propagate cells. In particular this combination can be used to provide enhanced pluripotent cell self-renewal and/or enhanced maintenance of pluripotency. The combination may further be used for derivation of pluripotent cell populations. In a specific embodiment of the invention it has been found that a combination of the factor and Oct-4 leads to improved pluripotent cell self-renewal, and this improvement is exploited in the derivation of new pluripotent cell lines, especially of human cells but also of other animals, including murine such as rat and mouse; primate such as monkey, especially macaque; porcine; sheep; and bovine pluripotent cells, Pluripotent cells, especially ES cells, are suitably derived by transfecting blastocyst cells prior to plating or at plating, for example at the time that feeder cells are conventionally used, or at the time that the inner cell mass is spread onto a plate. The transfection can be carried out with cells on feeder layers or not on feeder layers, though there is an advantage in avoiding any contact between the cells to be transfected and feeder cells. It is known that transgenesis of pluripotent cells is achievable at this stage, including for pre-implantation embryos, and hence transfection so that a factor of the invention is expressed is used to derive stable, pluripotent cell populations.

Another use of the technology described lies in cellular and nuclear reprogramming, and accordingly the invention also provides a method of reprogramming the nucleus of a somatic cell, comprising contacting the cell with a factor of the invention and activating gp130 signalling in the cell, or comprising contacting the cell with a factor of the invention and expressing Oct-4 in the cell. For example, the reprogramming is carried out by transfecting the cell with a first vector that contains a nucleotide sequence encoding a factor of the invention, and with a second vector that contains a nucleotide sequence encoding a LIF receptor ligand or contains a nucleotide sequence encoding Oct-4.

The invention additionally provides polynucleotides encoding the factors of the invention. In use of the factor, there may be a number of different methods proposed for control or direction of expression of the factor so as to promote pluripotency of cells in culture or elsewhere. It is thus optional to include in the polynucleotide a sequence which regulates expression of the factor. This sequence may be a promoter, and can also be a promoter whose activity is regulated. Further polynucleotides of the invention encode the conjugates described above.

To control the level of factor in a given cell, a gene encoding the factor and present in the cell may be activated. Both endogenous and heterologous promoters and other regulatory elements may be used, as well as factors that act on these regulatory elements. One approach is to use a polynucleotide for inserting a regulatory sequence into the genome of a cell, wherein the regulatory sequence when inserted regulates expression of a gene encoding the factor. In this way, an endogenous gene can be turned on or its expression maintained. The regulatory sequence can be inserted by homologous recombination into the resident gene encoding the factor. The regulatory sequence may be a regulated promoter—for example an inducible promoter can be used so that the factor is expressed when culture medium contains an inducer; removing the inducer results in reduced expression of the factor and loss of pluripotent phenotype. Sequences which enable removal or inactivation of the promoter may also be included, to allow further control of expression of the factor.

Another method of controlling the level of a factor in a cell is to design or select sequence specific DNA binding polypeptide domains which recognize sequences in the promoter of the endogenous PDF gene, for example by using phage display (Isalan and Choo, 2001 Methods in Enzymology 340 p 593-609). Such sequence specific DNA binding domains may be used to activate or maintain transcription of the endogenous PDF gene by fusion to transcriptional activation domains. Alternatively, fusion of such sequence specific DNA binding polypeptide domains to silencer domains may be used to reduce PDF expression. Additionally, these fusions may be linked to other domains that promote uptake of the fusion protein into the cell. In this way molecules which act on the endogenous PDF gene itself may be administered to cells or expressed in cells.

The polynucleotides of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in SEQ ID NO: 1, 3, 5 or 7 may be a different coding sequence which coding sequence, as a result of the redundancy or degeneracy of the genetic code, encodes the same mature polypeptide as the DNA.

The isolated polynucleotides of the invention may encode (a) polypeptide molecules comprising an amino acid sequence as set out in SEQ ID NO: 2, 4, 6 or 8; (b) naturally occurring variants of (a); (c) orthologues of (a) or (b), and (d) biologically active and diagnostically or therapeutically useful fragments, analogues and derivatives thereof.

The polynucleotide which encodes for these polypeptides may also include additional coding sequence and/or non-coding sequence such as introns or non-coding sequence 5' and/or 3' of the coding sequence for the mature polypeptide. Thus, references to "polynucleotide" include reference to a polynucleotide which includes only coding sequence for the polypeptide as well as a polynucleotide which includes additional coding and/or non-coding sequence.

The present invention further relates to variants of the herein above described polynucleotides which encode fragments, analogues and derivatives of the polypeptide having the specified amino acid sequence. The variants of the polynucleotide may be naturally occurring variants of the polynucleotide or non-naturally occurring variants of the polynucleotide.

Thus, the present invention includes polynucleotides as shown in SEQ ID NO: 1, 3, 5 or 7 encoding the same mature polypeptide as well as variants of such polynucleotides which variants encode for a fragment, derivative or analogue of the factor. Such nucleotide variants include deletion variants, substitution variants and addition or insertion variants.

As herein above indicated, the polynucleotide may have a coding sequence which is a naturally occurring variant of the coding sequence shown in SEQ ID NO 1, 3, 5 or 7. As known in the art, an alternate form of a polynucleotide sequence may have a substitution, deletion or addition of one or more nucleotides, which does not substantially alter the function of the encoded polypeptide.

The present invention further relates to polynucleotides which hybridise to one or more of the herein above-described sequences if there is at least 70%, preferably at least 90%, and more preferably at least 95% identity between the sequences. The present invention particularly relates to polynucleotides which hybridise under stringent conditions to the herein above-described polynucleotides. As herein used, the term "stringent conditions" means hybridisation will occur only if there is at least 95% and preferably at least 97% identity between the sequences. The polynucleotides which hybridise to the herein above described polynucleotides in a preferred embodiment encode polypeptides which either retain substantially the same biological function or activity as the mature polypeptide encoded by the cDNAs of SEQ ID NO: 1, 3, 5 or 7.

Alternatively, the polynucleotide may have at least 20 bases, preferably at least 30 bases, and more preferably at least 50 bases which hybridise to a polynucleotide of the present invention and which has an identity thereto, as herein above described, and which may or may not retain activity. For example, such polynucleotides may be employed as probes for the polynucleotide of SEQ ID NO: 1, 3, 5 or 7, for example, for recovery of the polynucleotide or as a diagnostic probe or as a PCR primer.

Still further provided by the present invention are vectors for use in expressing the factor of the invention. A first vector comprises a polynucleotide of the invention as described above. A vector described and used in an example of the invention, set out in more detail below, is designed for transfection of a cell such that the factor is expressed in the cell and the transfected cell may be maintained in a pluripotent state. Generally, such vectors comprise the following operatively linked elements: a transcription promoter; a DNA segment comprising a polynucleotide of the invention; and a polyadenylation signal. A further option is for the vector additionally to encode for a selectable marker, with selection used to identify cells that have taken up and are expressing the vector. As an example, the vector can encode antibiotic resistance, with addition of antibiotic to the culture used to identify successful transfectants. Following transfection of the cell, the vector may be chromosomally integrated or maintained extra-chromosomally and the coding sequence on the vector expressed so that a level of the factor is maintained in the cell sufficient to keep the cell in a pluripotent state. A particular vector is designed for transfection of a cell expressing or containing polyoma large T antigen. Such a vector may have a polyoma origin of replication, such that the vector is stably maintained in the cell when polyoma large T antigen is present.

Further control and flexibility may be conferred on the system by using a promoter in the vector whose activity can be controlled. Thus, following transfection, the promoter may be in a non-active state, allowing the user to choose when to activate the promoter, for example using an inducible promoter the inducer can be added to culture medium. As an alternative, the promoter may be initially active but such that its activity can be reduced or turned off by addition of a suppressor substance to culture medium—this enables the user to determine, after a period of maintaining cells in a pluripotent state, to halt expression of the pluripotency determining factor from the vector, allowing the cells to differentiate and substantially clearing the culture of any remaining pluripotent cells. In preparation of differentiated progeny there is a need to remove undifferentiated cells, and thus this element of the invention provides this capability. A suitable system is the tet regulatory system (Baron & Bujard, 2000). The vector may additionally be constructed such as to enable its subsequent removal, or removal of the sequence encoding the factor, by site specific recombination.

A vector of a further embodiment of the invention comprises a nucleotide sequence which encodes a regulatory factor, wherein the regulatory factor regulates a gene encoding the factor of the invention. The regulatory factor can be used to activate or turn on or otherwise increase expression from the gene, which may be an endogenous gene or may be located extra-chromosomally. This particular vector has a number of uses. A transgenic line of animals may be prepared in which a gene encoding the pluripotency determining factor is substantially turned off. The transgenic animals can then be used to generate embryos and pluripotent cells explanted therefrom and transfected with this vector such that the regulatory factor of the vector turns on expression of the pluripotency determining factor, allowing maintenance of a culture of pluripotent cells. Alternatively, a binary transgenic animal can be generated containing both the vector for the regulatory factor and also the regulatable gene for a pluripotency determining factor. The latter can then be induced in vivo to mobilize stem cells.

A principal use of the factor, whether directly or by expression of a nucleotide sequence encoding the factor, is in maintenance of cells in a pluripotent state. The polynucleotide may be a sequence endogenous to the cell, for example the native sequence may be activated, to achieve the maintenance of pluripotency, or a nucleotide sequence introduced into the cell may be used. The introduced sequence may also be on a plasmid. A nucleotide encoding the factor may also be on a stably integrated transgene.

The invention hence provides a method of maintaining a pluripotent cell population, comprising administering to that population a factor of the invention. A further culture method is to maintain a cell in a pluripotent state by activating a gene in the cell that encodes a factor of the invention. A yet further culture method for maintaining a cell in a pluripotent state comprises maintaining or increasing expression of a gene in the cell that encodes a factor according to the invention.

The pluripotency determining factors of the invention can also be used to increase the potency of a somatic or non-pluripotent cell. Hence, a method of the invention comprises increasing the potency of a cell by exposing the cell to a pluripotency determining factor, this exposure optionally being carried out by introducing the factor into the cell or expressing in the cell a nucleotide sequence encoding the factor. The increase in potency of the cell may be such as to re-programme the nucleus of the cell, leading to the somatic or non-pluripotent cell being converted into a pluripotent stem cell. Alternatively, the effect of the factor of the invention upon the cell may be to increase its potency but not to increase its potency so far as to render the cell pluripotent. Once a cell has had its potency increased, the cell may then be subjected to differentiation down a different lineage, and hence the factor of the invention can be useful in respecifying the lineage of a given cell.

The factor enables a number of different strategies for obtaining pluripotent cells to be pursued. In one such strategy, a pluripotent non-human cell is isolated by creating a transgenic animal, the animal containing a construct in which a nucleotide sequence encoding the factor of the invention is under the control of a regulated promoter. A transgenic embryo is then obtained from the transgenic animal and a cell, such as an epiblast cell or a primordial germ cell, obtained from the embryo. By activation of the promoter the factor is expressed in the cell and, subsequently, pluripotent cells can be isolated. In this approach, therefore, the transgenic animal is made as an initial step and this approach is particularly suitable where procedures exist for creation of transgenic animals. In another approach, which can for example be adopted in species in which it is not possible or in which it is technically more demanding to make transgenic animals, a nucleotide encoding the factor of the invention is introduced into a cell in a freshly isolated cell population and a pluripotent cell isolated thereafter. In this latter approach, cells from the freshly isolated cell population are transfected quickly, that is to say without allowing the cells to remain in culture for sufficient time for them to have differentiated before at least one cell is transfected such that the factor is expressed in that cell. As mentioned, this approach can have particular utility in deriving and maintaining pluripotent cells from mammals or other animals in which it is not possible to make transgenic animals. Hence, also included within the invention are transgenic animals obtainable by these methods and transgenic animals containing a nucleotide sequence encoding a factor according to the invention under control of a regulatable promoter.

Methods are described herein in which the factor and functional analogues, variants, fragments and derivatives are used to promote maintenance of pluripotency. Another benefit of the invention and the identification of pluripotency determining factors is that we now have the opportunity to devise antagonists to these pluripotency determining factors, which antagonists can be used to inhibit the activity of pluripotency determining factors or otherwise act as antagonists to such factors. Antagonists to the factors can be used to promote differentiation of a pluripotent cell, and this has utility for example in situations in which it is desired to eliminate pluripotent cells either from a culture or in vivo. The present invention also enables production of animals that are dominant negative for the factor, such as animals containing dominant negative variants or other dominant negative mutants of the gene encoding the factor.

Thus, also provided by the invention is a composition comprising a pharmaceutically acceptable carrier plus an antagonist of a factor of the invention. Antagonists can be used to effectively remove pluripotent cells prior to introduction of pluripotent cell-derived progeny into a patient, such as in cell therapy, avoiding for example teratomas and/or other tumours due to contamination of transplanted material by pluripotent cells. This can be applied in vivo or in vitro. Another use for the antagonist is as a contraceptive. A further use of the antagonist of the invention is generally for treatment of tumours, in particular tumours associated with inappropriate expression of a factor of the invention.

Cells are provided by the invention in which the expression or activity of a factor of the invention has been manipulated. These cells can be maintained in a pluripotent state. A first cell of the present invention expresses a factor of the invention for a period of time in excess of 2 weeks. Further cells of the invention are (1) a cell comprising a vector of the invention, (2) a pluripotent, human cell, maintained in a pluripotent state in the absence of feeder cells and in the absence of feeder cell extract, and (3) a cell comprising a gene encoding a factor according to the invention wherein the gene has been activated.

Cells of the invention can also be used in a screen for molecules that interfere with the function of the factor of the invention. One such screen comprises culturing a pluripotent cell in the presence of a factor of the invention, the factor being present for example by being provided in cell culture medium or by being expressed in the cell, culturing the cell in the presence of a test substance and observing whether there is any alteration in the pluripotent phenotype of the cell. This assay can be used to select for antagonists of the factor or for other molecules that interfere with its activity. The screen can also be used to identify test substances with functions of inducing differentiation of the cell.

Cells of the invention can additionally be used in assays for drug discovery. Cells of the invention may also be used for cell therapy, and thus a method of the invention comprises using the factor of the invention to derive and/or maintain pluripotent cells, deriving cells for cell therapy therefrom and using those cells in cell therapy.

A screening method of the invention, for screening a cDNA library, comprises performing the screen in pluripotent cells, and selecting for a self-renewing phenotype. The screen can use pluripotent cells that are cytokine non-responsive, and has advantage in that both extrinsic and intrinsic factors can be thereby identified.

The invention further provides a method of screening a cDNA library comprising carrying out a complementation assay in pluripotent cells. The method can be employed to identify a cDNA which confers a self-renewing phenotype.

The invention yet further provides a method of screening for a factor that maintains a pluripotent cell in a pluripotent state, comprising:— providing a pluripotent cell which expresses a pluripotency determining factor of the invention, which cell is stably maintained in a pluripotent state and in which expression of the factor can be controlled;

carrying out a manipulation of the cell;

reducing expression of the pluripotency determining factor; and selecting for a cell that is maintained in a pluripotent state.

Manipulations can be designed so as to result in a screen for extrinsic factors, cell surface receptors, cDNAs or other factors, and suitable manipulations include a genetic manipulation of the cell and a manipulation of culture medium or culture conditions in which the cell is cultured. The screen can thereby be made suitable for identifying a factor which controls expression of an endogenous gene coding for a pluripotency determining factor of the invention or for a further factor that maintains the cell in a pluripotent state. Preferably, expression of the factor is controlled by regulating a regulatable promoter in operative combination with a nucleotide sequence encoding the factor, enabling expression of the factor to be reduced, so as to remove the activity of the pluripotency determining factor, by adding a repressor to medium in which the cell is cultured. Cells that remain pluripotent can then be isolated and characterized to determine the identity of the factor that has substituted for pluripotency determining factor.

A further screen of the invention is one for identifying regulation of the endogenous gene, and the invention further provides a method of screening for a factor that regulates expression of an endogenous gene which codes for a pluripotency determining factor of the invention, comprising:—

(1) analysing regions of the genome that flank the endogenous gene for presence of transcription factor binding sites, and (2) screening fragments of those regions with an extract from ES cells to identify a component of the extract that bind to the fragments.

Regions of the genome that flank the endogenous gene and direct pluripotent cell restricted expression of the factor are preferably identified, suitably by transfection of reporter constructs, so that the screen can identify one or more components in the ES cell extract that are putative transcription factors for pluripotency determining factor. Further analysis of the results of the screen can include research into whether control of the putative transcription factor, such as via an extracellular substance, has already been identified. The thus identified controlling factors can be used to derive and/or maintain pluripotent mammalian cells.

The term "orthologue" denotes a polypeptide or protein obtained from one species that is the functional counterpart of a polypeptide or protein from a different species. Sequence differences among orthologues are the result of speciation.

The term "allelic variant" denotes any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence.

The term "expression vector" denotes a DNA molecule, linear or circular, that comprises a segment encoding a polypeptide of interest operably linked to additional segments that provide for its transcription. Such additional segments may include promoter and terminator sequences, and may optionally include one or more origins of replication, one or more selectable markers, an enhancer, a polyadenylation signal, and the like. Expression vectors are generally derived from plasmid or viral DNA, or may contain elements of both.

The term "isolated", when applied to a polynucleotide molecule, denotes that the polynucleotide has been removed from its natural genetic environment and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are generally free of other genes with which they are ordinarily associated, but may include naturally occurring 5' and 3' flanking regions containing regulatory elements such as promoters, enhancers and terminators. The identification of associated regions will be evident to one of ordinary skill in the art (see for example, Dynan and Tijan, Nature 316:774-78, 1985). When applied to a protein, the term "isolated" indicates that the protein is found in a condition other than its native environment, such as apart from blood and animal tissue. In a preferred form, the isolated protein is substantially free of other proteins, particularly other proteins of animal origin. It is preferred to provide the protein in a highly purified form, i.e., greater than 95% pure, more preferably greater than 99% pure.

The term "operatively linked", when referring to DNA segments, denotes that the segments are arranged so that they function in combination for their intended purposes, e.g. transcripts initiate in the promoter and proceed through the coding segment to the polyadenylation site.

The term "polynucleotide" denotes a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules.

The term "complement" with respect to polynucleotide molecules denotes polynucleotide molecules having a complementary base sequence and reverse orientation as compared to a reference sequence. For example, the sequence 5' ATGCACGGG 3' is complementary to 5' CCCGTGCAT 3'.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "promoter" denotes a portion of a gene containing DNA sequences that provide for the binding of RNA polymerase and initiation of transcription. Promoter sequences are commonly, but not always, found in the 5' non-coding regions of genes.

The invention is now described in the following specific embodiments, illustrated by the accompanying drawings in which:—

FIG. 3 shows sequence analysis of PDF cDNA in which:

(A) shows alignment of the PDF homeodomain with the most closely related representatives of several different classes of homeodomain protein (SEQ ID NOS:10-23). The alignment was generated with Clustal W and shaded, using MacBoxshade, with respect to PDF: dark grey, identical in all sequences; mid grey, identical to PDF; light grey, similar to PDF. Percentage identities to the PDF homeodomain are shown on the right.

(B) shows pairwise comparison of mouse (Mm) PDF and the human (Hs) orthologue (hypothetical protein FLJ12581) (SEQ ID NOS:2 and 4). Identical residues are boxed.

(C) shows that the 3' UTR of the mouse PDF cDNA contains a B2 repeat (SEQ ID NOS:24 and 25). Numbering is according to PDF cDNA and B2 sequence accession number K00132. The split RNA polymerase III promoter of B2 is boxed. Asterisks indicate bases that differ between the PDF cDNA descried here and the RIKEN cDNA AK010332.

(D) demonstrates the activity of the human orthologue of PDF in mouse ES cells. LRK1 cells were transfected with pPyCAGIP (no insert) or a derivative carrying a hPDF ORF insert. The number of alkaline phosphatase positive colonies with no surrounding differentiated cells were counted and expressed as the percentage formed in the absence of cytokine relative to the number formed in the presence of IL6/sIL6R.

FIG. 4 shows that expression in vitro is restricted to pluripotent cells, in which:—

(A) shows comparative hybridisation of RNA from MEFs and from MEF/ES cell co-cultures used for library construction. 1 µg pA$^+$ RNA was loaded per lane and hybridised with probes for PDF cDNA (left), GAPDH (right) and PDF ORF (middle). Positions of migration of RNA markers of the indicated sizes (kb) are shown to the left.

(B) shows PDF transcripts detected by in situ hybridisation of a MEF/ES cell co-culture (left) and an undifferentiated colony of cells surrounded by differentiated cells in an E14Tg2a culture (right); bars are 50 µm.

(C) shows expression in cell lines is restricted to ES, EC and EG cells. RNAs used were PSMB, PC13.5, F9, PSA4, P19, EC cells; CGR8, ES cells; PE, Parietal endoderm; PYS, parietal yolk sac; NIH3T3, fibroblasts; BAFB03, pro-B cells; MEL, erythroleukaemia; B9, plasmacytoma.

(D) shows PDF expression is repressed upon ES cell differentiation. RNAs were from E14Tg2a cells induced to differentiate by application of RA or MBA for the number of days shown.

(E) shows a lack of detectable expression of PDF in adult tissues. RNAs used were 1, epidydimis; 2, testes; 3, CGR8; 4, adipose; 5, kidney; 6, liver; 7, heart; 8, spleen; 9, brain; 10, bone marrow; 11, tongue; 12, eye; 13, oviduct; 14, thymus; 15, skeletal muscle; 16, skin; 17, ovary; 18, seminiferous vesicle; 19, lung.

(F) shows human PDF RNA is expressed in EC cells. RNAs used were from embryonal carcinoma (GCT27C4) and lymphoid (Jurkat) cells. Northern blot analysis was performed by sequential hybridisation using probes for PDF, GAPDH and Oct4 (C, D), PDF and GAPDH (E) and hPDF and GAPDH (F).

Figure 5A:
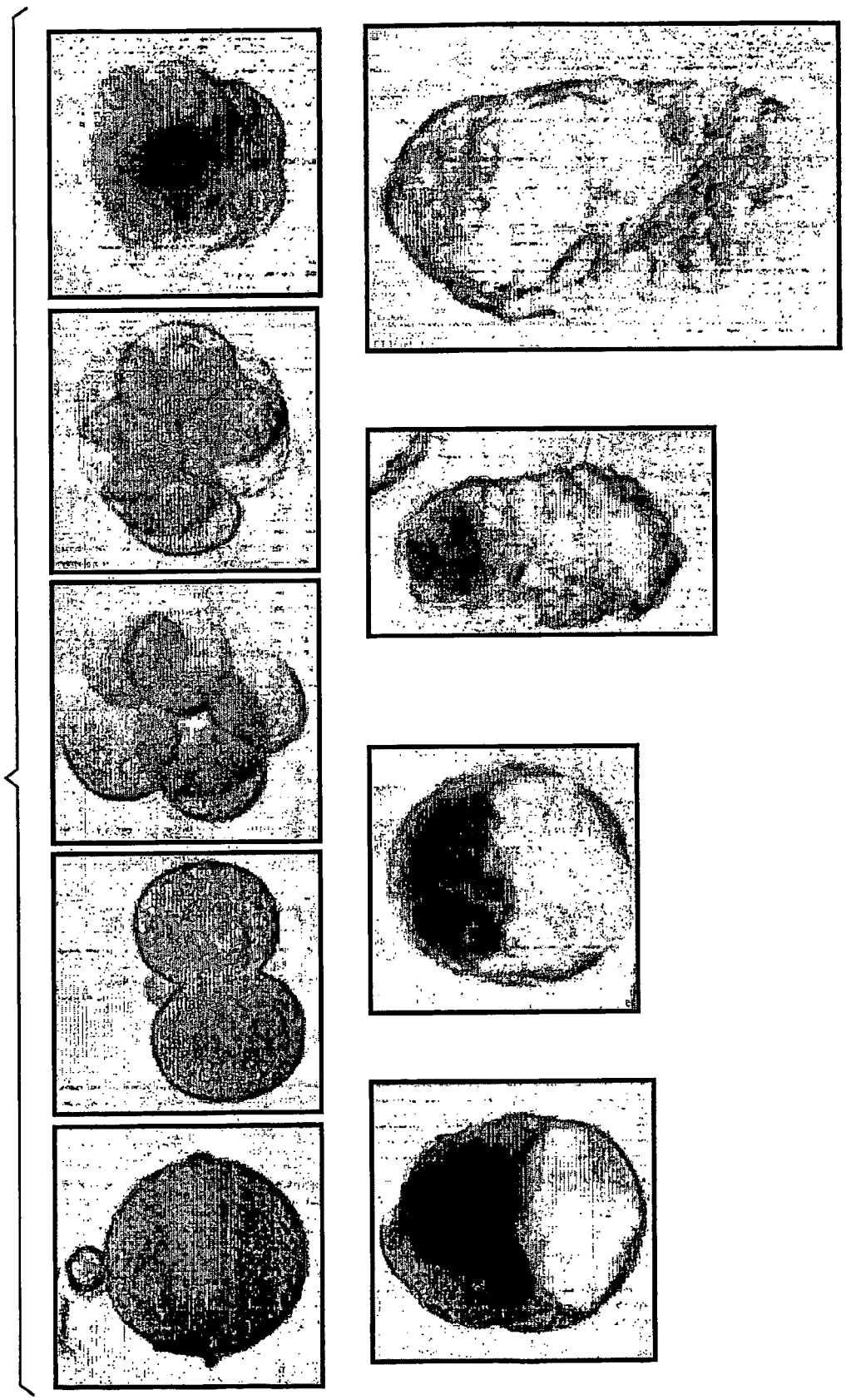

FIG. 5 shows expression of PDF in vivo in which PDF mRNA was visualised by in situ hybridisation using an ORF probe and:—

(A) shows pre-implantation embryos. The top series shows embryos of 1, 2, 6 and 8 cells and a late morula. The bottom series shows blastocysts at early, expanded, hatched and implanting stages. All panels are shown at the same magnification.

(B) shows E11.5 genital ridges from female (top) and male (bottom) embryos.

FIG. 6 illustrates the reversibility of gp130 independent self-renewal, in which:—

(A) provides a diagram of construct. The CAG cassette directs expression of a PDF-IRES-pacpA transcript.

This is followed by a transcription terminator sequence (STOP; SPA C2 MAZ) and an egfppA cassette. The loxP sites are positioned in the second exon of the CAG cassette and between the terminator sequence and egfp such that following Cre mediated recombination CAG directs expression of egfp.

(B) shows Northern blot analysis of transgene transcripts before (PDF-IRES-pac, pac probe) and after (gfp) Cre excision. The blot was hybridised sequentially with the indicated probes. E, E14Tg2a; EF1, E14Tg2a subclone carrying the Floxed transgene; EF1C1, EF1 subclone following Cre-mediated excision.

(C) shows that reversal of PDF expression restores LIF dependent self-renewal. ES cells (ZIN40), ES cells expressing the Floxed PDF transgene and their Cre-excised derivative lines were analysed following plating at clonal density in the indicated culture conditions; 0, no addition; LIF, 100 u/ml LIF, hLIF-05, LIF antagonist sufficient to block 10 units/ml LIF. After 6 days culture the percentage of alkaline phosphatase positive colonies lacking discernible differentiated cells was quantitated.

(D) shows the morphology of PDF expressing cells and their Cre-excised derivative in the absence of cytokine (0), in 100 u/ml LIF (LIF) or in the presence of LIF antagonist sufficient to block 10 units/ml LIF (hLIF-05). Cells were plated at clonal density and examined after 4 days culture.

(E) shows Northern blot analysis of RNA from cultures of E14Tg2a derivatives expressing the floxed transgene (EF4) or a Cre excised subclone (EF4C3) prepared at 0,1,2,3 or 4 days following exposure to RA or MBA and hybridised to Oct4.

FIG. 7 shows the reversibility of gp130 independent ES cell identity, in which:—

(A) shows differentiation by aggregation. E14Tg2a derivatives expressing the floxed transgene (EF4) or Cre excised subclone (EF4C3) were assessed for cardiac differentiation by placing individual embryoid bodies in a well of a 48 well dish and scoring each well daily for the presence of beating cells.

(B) shows differentiation by aggregation in the presence of retinoic acid. E14Tg2a and derivatives expressing the floxed transgene (EF4) or Cre excised subclone (EF4C3) were assessed for neurogenesis by TuJ immunohistochemistry.

(C) shows the contribution of Cre deleted cells to mid gestation embryo. EF1C1 cells were injected into an MF1 blastocyst and after transfer to a foster mother examined at E9.5 for green fluorescence.

FIG. 8 shows the relationship of PDF to other known mediators of self-renewal, in which:—

(A) shows that the proportion of cytokine independent colonies correlates with the level of episomal PDF expression. LRK1 cells were transfected with episomal vectors directing increasing levels of expression of PDF (pPyPPGK<pPyPCAG<pPyCAGIP). Following 12 days of selection, the proportion of self-renewing colonies in the absence of cytokine is expressed relative to the number in the presence of IL6/sIL6R. Data are the average of two independent experiments.

(B) shows that PDF is not a STAT3 target. ES cells expressing chimaeric GCSFR-gp130 variant molecules in which all four STAT3 binding sites were abolished by mutation of tyrosine codons to phenylalanine (Y126-275F) or in which the negative regulatory tyrosine was similarly mutated (Y118F) were stimulated with LIF (L) or GCSF (G) for the indicated time (mins) before RNA preparation. Northern blot analysis was performed by sequential hybridisation with probes against PDF, GAPDH or the STAT3 target gene SOCS3.

(C) shows that PDF cannot substitute for Oct4 in self-renewal. ES cells in which doxycycline responsive Oct4 transgene sustains self-renewal (ZHBTc4.1) were transfected with linearised pPyCAGIP derivatives carrying no insert (MT), Oct4 (Oct) or PDF (PDF) and cultured in the presence of LIF under conditions in which the transgene remains expressed (0) or is switched off (Dox). Following puromycin selection, plates were stained and the percentage of undifferentiated colonies determined.

Figure 9A:
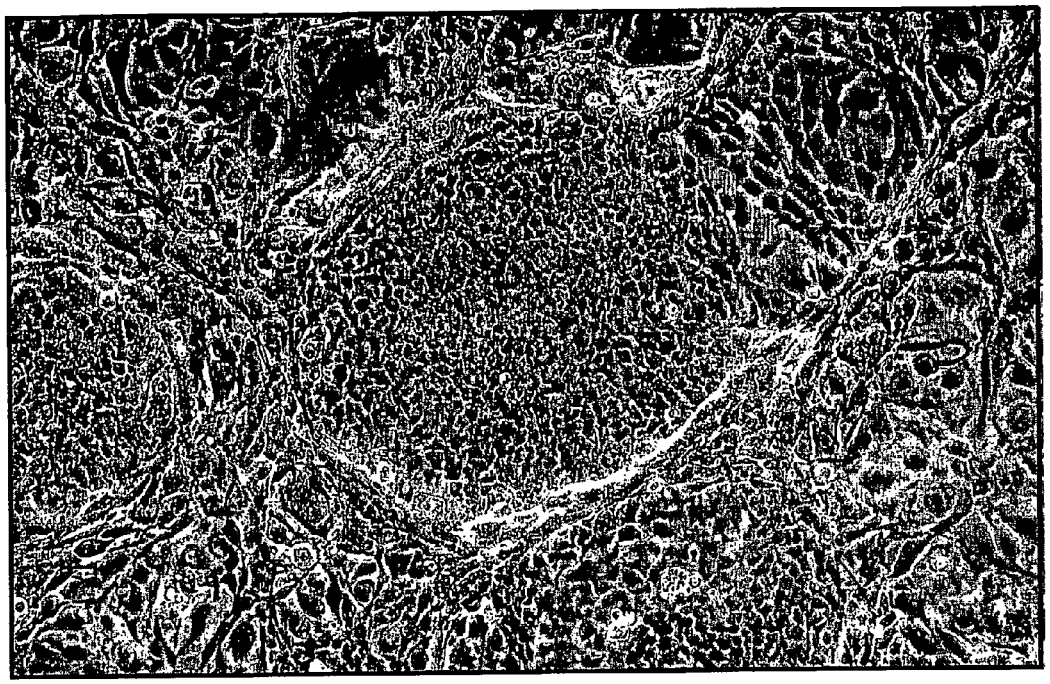

FIG. 9 illustrates the maintenance of pluripotent GCT 27X-1 hEC cells in conditioned medium in which:—

(A) shows the GCT 27X-1 pluripotent hEC cell line, which is routinely maintained on a feeder layer of mitotically inactivated STO cells.

(B) depicts pluripotent cultures, shown at a routine density, and which can also be maintained in the absence of feeder cells but with the addition of conditioned medium derived from the yolk sac carcinoma cell line hEC 44 to 25% v/v in the routine culture medium.

(C) shows that withdrawal of this conditioned medium from feeder-free GCT 27X-1 cell cultures, shown at a clonal density, results in the initiation of cell differentiation and loss of pluripotent phenotype. Photographed under phase-contrast optics, 10×(A, B), 4×(C).

Figure 10:
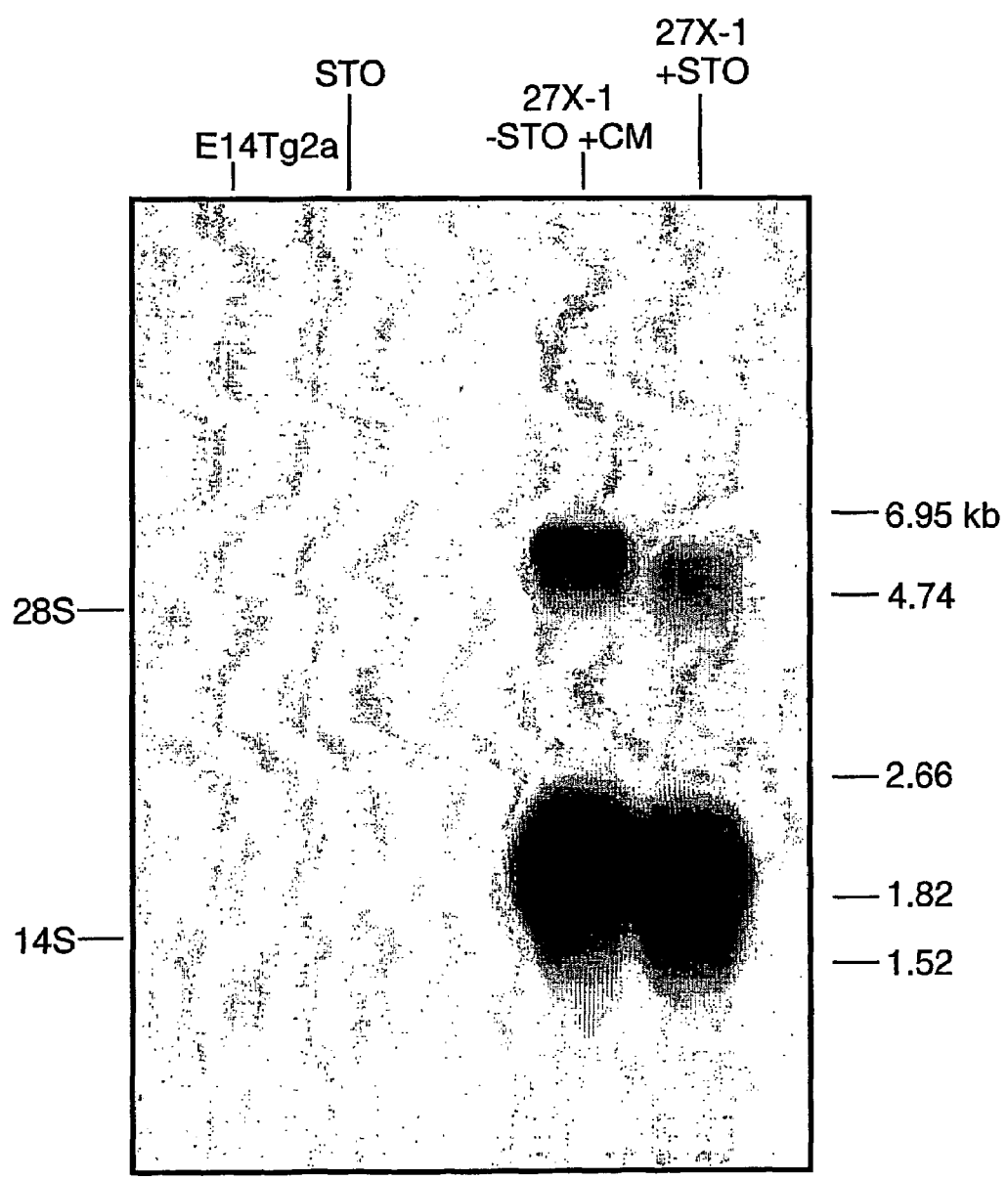

FIG. 10 shows the Northern blot analysis of endogenous hPDF expression in GCT 27X-1 hEC cells, in which poly A+ mRNA (3-3.5 µg) prepared from GCT 27X-1 cells cultured on STO feeder cells (27X-1+STO), and without feeder cells but with the addition of conditioned medium (27X-1–STO+CM), was separated on a denaturing gel and analysed by Northern blot hybridisation with a cDNA probe (~900 bp) specific to the candidate human PDF sequence. Poly A+ mRNAs prepared from a STO cell culture (STO) and from an E14Tg2a mouse ES cell culture (E14Tg2a) were included as controls for hybridisation. A major transcript of ~2.4 kb and a lesser hybridising transcript of ~5.6 kb were detected in both GCT 27X-1 cultures, confirming endogenous expression of the hPDF gene in pluripotent hEC cell cultures. A very weak hybridisation band of ~2.2 kb detected in the mouse ES cell line is indicative of a homologous transcript in mouse pluripotent cells. As expected no hybridisation signal was detected for STO cell mRNA. Autoradiographic exposure is shown for 8 hrs at −70° C. with intensifying screens.

Figure 11:
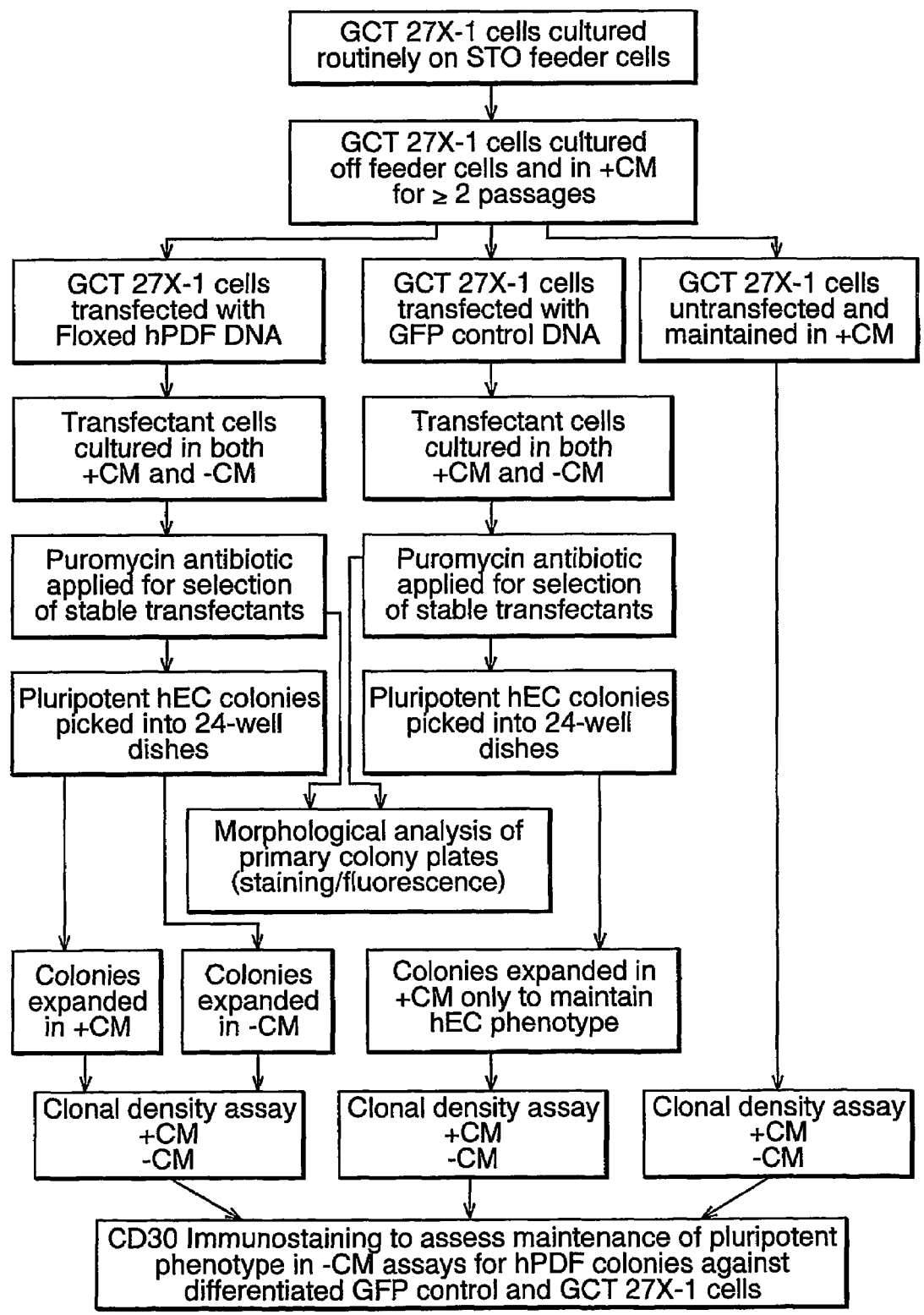

FIG. 11 provides a flow chart describing experimental strategy to demonstrate the maintenance of self-renewal in a human pluripotent cell line expressing the hPDF cDNA. (CM=conditioned medium)

Figure 12A:
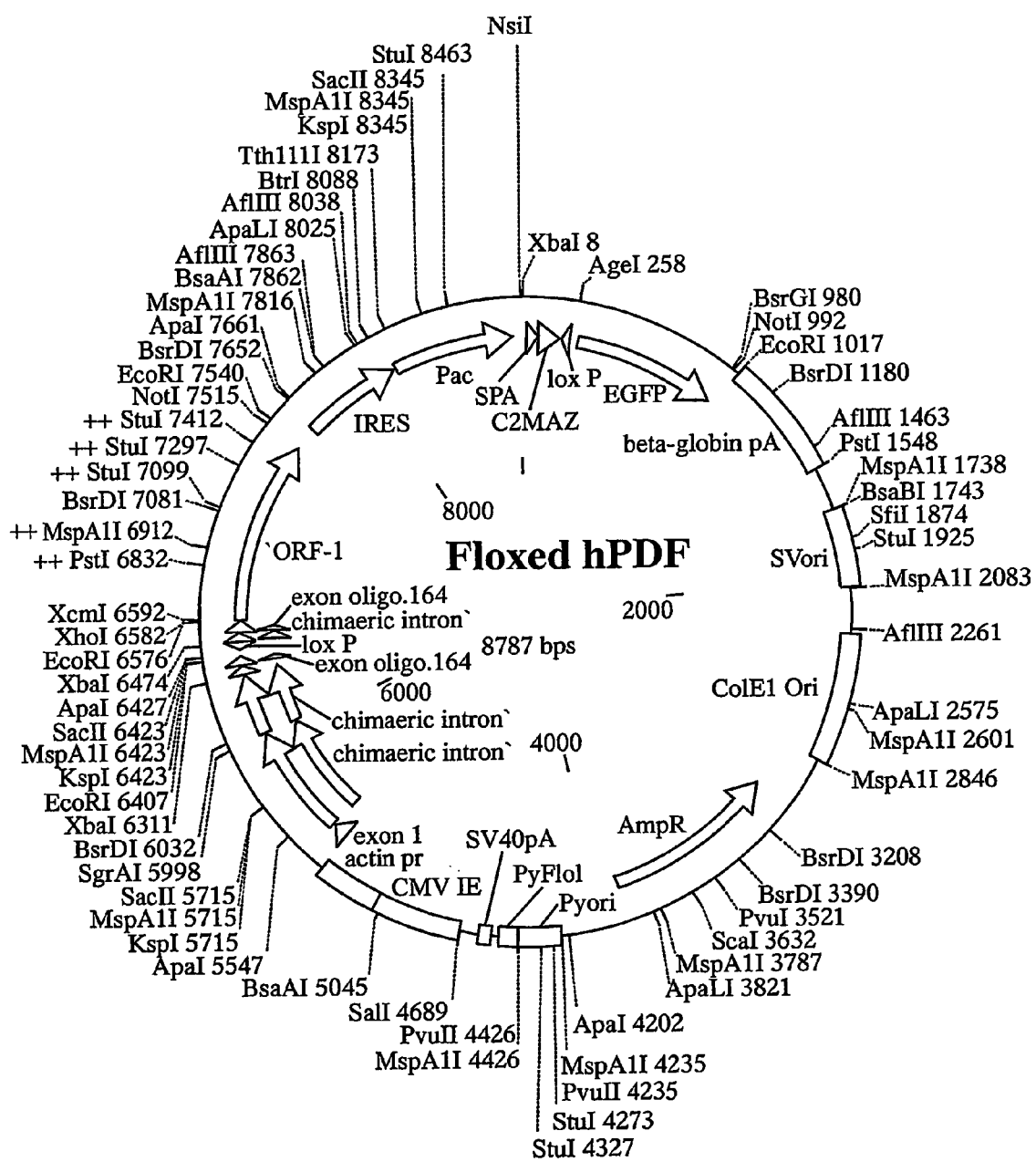
Figure 12B:
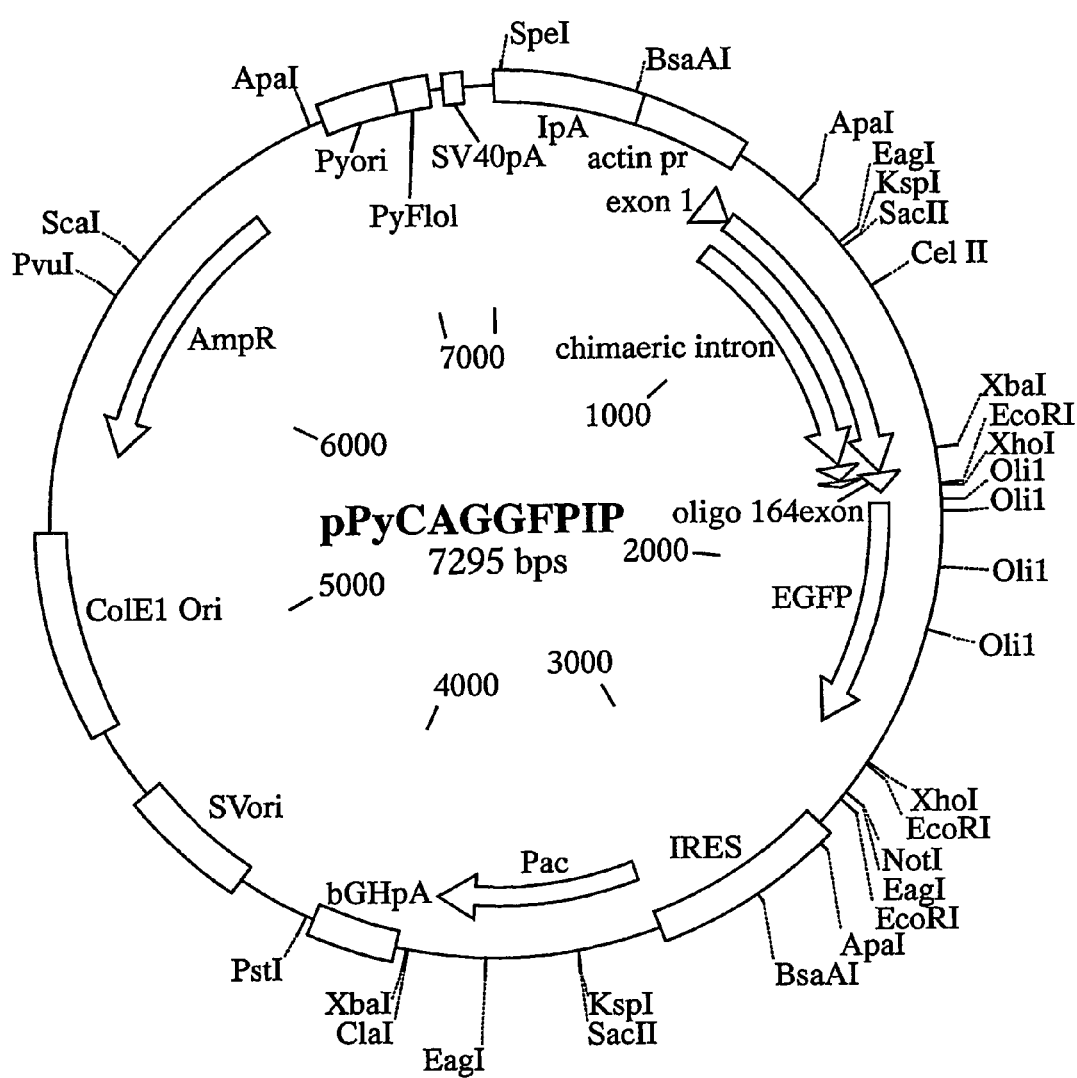

FIG. 12 illustrates the floxed hPDF and GFP control vector constructs, in which:—

(A) shows the 8.8 kb Floxed hPDF construct, which contains the open reading frame for the hPDF cDNA (~900 bp) operating under a human cytomegalovirus immediate early enhancer (CMV IE) and the human actin promoter, upstream of a bicistronic reporter cassette providing for IRES-mediated expression of the puromycin resistance gene. The enhanced GFP (eGFP) reporter gene lies downstream of loxP sites, providing for visualisation by fluorescence where Cre-mediated recombination occurs.

(B) shows the pPyCAGegfpIP ("GFP control") vector, which is a similar construct in which the hPDF sequence in (A) is replaced by the eGFP sequence upstream of the IRES-puromycin reporter cassette and was used to provide control "non hPDF"-expressing transfectants.

FIG. 13 illustrates the morphological evaluation of transfectant GCT 27X-1 colonies. Stable transfectant Floxed hPDF and GFP control colonies were established following 10-15 days in puromycin selection culture without STO feeder cells, in the presence and absence of conditioned medium. Following Leishman's staining colony morphology was scored as (A) "Tight": those colonies maintaining a tight pluripotent hEC phenotype, (B) "Medium": those colonies starting to differentiate while maintaining some hEC phenotype and (C) "Loose": those colonies that were completely loose and differentiated. Photographed under phase-contrast optics, 4×.

FIG. 14 illustrates the morphology of hPDF-expressing hEC cells in a clonal assay, in which a-d show hPDF-expressing hEC clonal lines expanded continuously in the presence (hPDF D7) and absence (hPDF E7) of conditioned medium from transfection, which were cultured at a clonal density for 12-14 days with (+CM) and without (−CM) conditioned medium.; and e-h show a transfected GFP control clone (GFP C15) and wild type hEC cells (27X-1), which were also cultured under the same conditions. In the absence of conditioned medium, only hPDF-expressing hEC cells are able to maintain a pluripotent hEC phenotype, while GFP control and wild type hEC cells are induced to differentiate. Photographed under phase-contrast optics, 10×.

FIG. 15 shows the self-renewal of hPDF-expressing hEC cells in a clonal assay. hPDF-expressing hEC clonal lines (hPDF D7 and E7), a transfected GFP control clone (GFP C15) and wild type hEC cells (27X-1), were cultured at a clonal density for 12-14 days in the presence (+CM, a-h) and absence (−CM, i-p) of conditioned medium. Pluripotent hEC cells within colonies were identified by indirect immunofluorescent staining for the CD30 marker (b, d, f, h, j, l, n, p), shown here with comparative Hoechst UV fluorescence for all cells within the same colony (a, c, e, g, i, k, m, o). In the absence of conditioned medium, only hPDF-expressing hEC colonies are able to maintain a pluripotent phenotype, while control transfected and wild type hEC cells are induced to differentiate unless maintained in conditioned medium. The hPDF E7 colonies displayed a generally tighter morphology and stronger detection of the CD30 marker when compared with hPDF D7 cells, in the absence of conditioned medium. Colonies were visualised using 535/50 nm (CD30) and UV 330-380 nm (Hoechst) filters, at 20× magnification.

Figure 16:
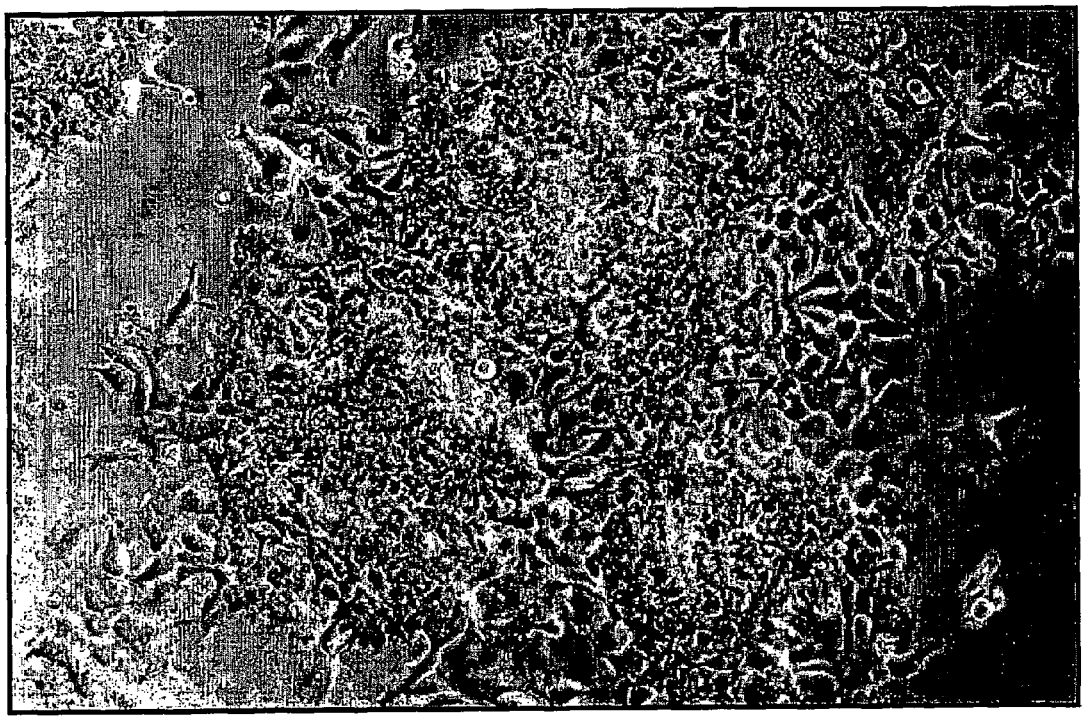

FIG. 16 illustrates the self-renewal of hPDF-expressing hEC cells in routine culture. The hPDF-expressing hEC cell line E7 has been expanded in the continuous absence of both STO feeder cells and conditioned medium since the time of transfection. This clonal cell line, shown here following routine passaging, continues to display self-renewal of hEC cells after more than 8 weeks of culture under these conditions. Photographed under phase-contrast optics, 10×.

EXAMPLE 1

Pluripotency Determining Factor

Design of Screen

Figure 1:
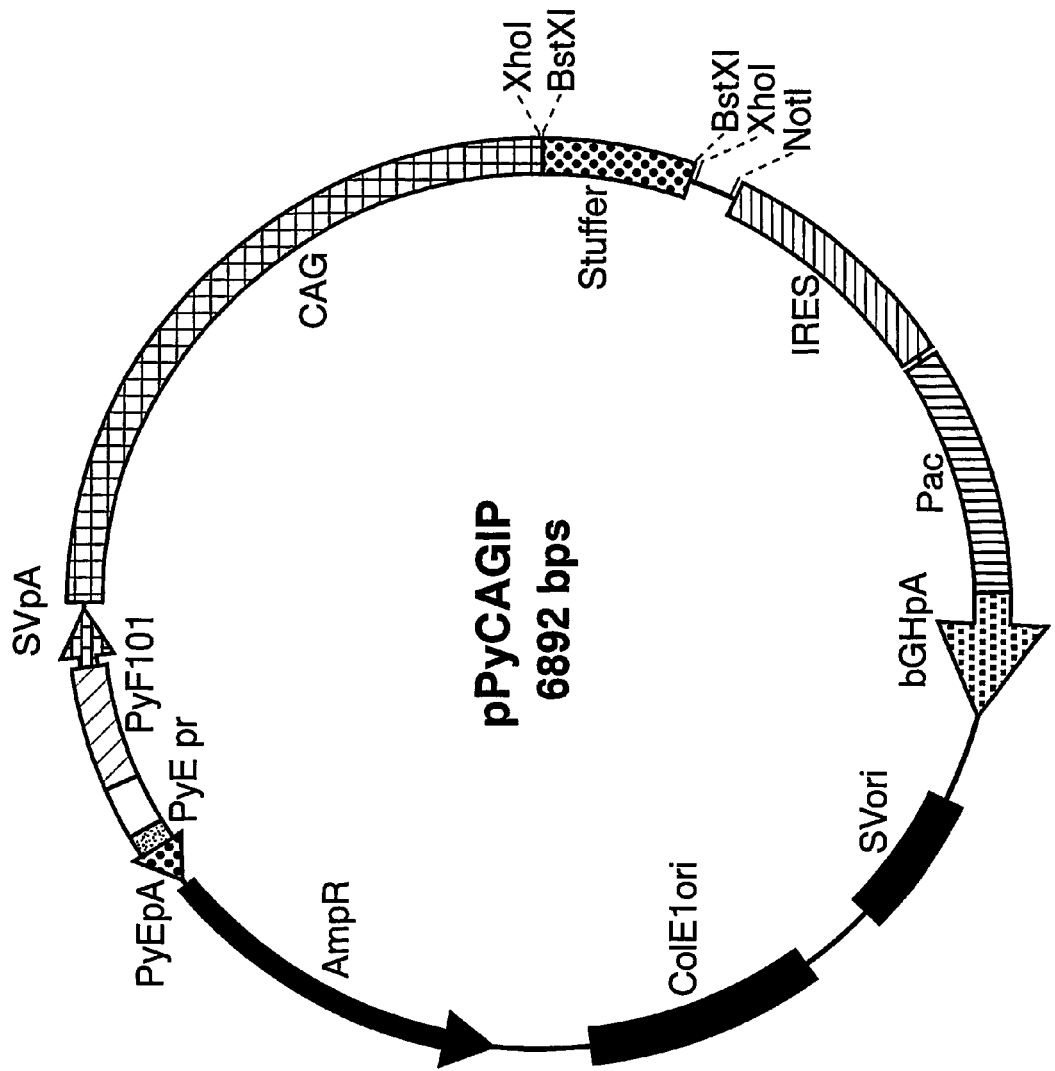
FIG. 1 shows the plasmid pPyCAGIP.

A functional screen of a cDNA library was designed to meet two criteria. Firstly, the frequency with which cDNA can be introduced into cells and maintained for the duration of the screen was to be high enough so that screening a complex library of $10^5$-$10^6$ independent cDNAs is practical. This is fulfilled by the combined use of LRK1 cells (described below) which express polyoma large T antigen and the polyoma origin containing vector pPyCAGIP (FIG. 1). Of the episomal vectors we have tested, this plasmid gives the highest levels of cDNA expression (data not shown). Furthermore, compared to selections with Blasticidin S, Hygromycin B and Zeocin, Puromycin selection allows the most rapid elimination of untransfected ES cells with 95% untransfected cells killed within 1 day (data not shown). Thus, a potential source of confounding biological activities is quickly removed from the cultures. Secondly, the property for which one is screening was to be present in the cell line being transfected at a sufficiently low level to enable the screen to proceed without a prohibitively high background. Ideally this property is absent from but expressible in the host cell line. LRK1 cells fulfil this critical criteria. During differentiation in vitro, expression from the LIF locus increases (Rathjen et al. 1990) and a number of ES colonies can be seen to emerge from the differentiated cell monolayer (Dani et al. 1998). Much of these re-emergent colonies appear due to the action of LIF (Dani et al. 1998). E14/T cells which retain responsiveness to LIF exhibit this background self-renewal following differentiation. In contrast, LRK1 cells which have lost responsiveness to cytokines acting via LIFR produce a far smaller number of colonies following the withdrawal of IL6 and sIL6R. This reduction in background self-renewal is sufficient to allow a library screen to be performed using these cells.

Preparation of LRK1 Cells

A cell line which could be supertransfected at high frequency with polyoma origin containing vectors was required in order to enable cDNA library screening to proceed at high efficiency. The cell line E14/T, a derivative of E14Tg2a cells which had been transfected with the plasmid pMGD20neo (Gassmann et al. 1995) and which supported replication of a supertransfecting plasmid was chosen as this line retained the ability to differentiate efficiently upon withdrawal of LIF. This line was subjected to two rounds of gene targeting aimed at the LIFR locus. The targeting vectors employed used the same homology arms as previously described (Li, Sendtner & Smith, 1995) but the selectable marker cassette was replaced with an IRESBSDrpA and an IREShphpA cassette for the first and second rounds of gene targeting, respectively. The resultant cell line (LRK1) retained a high supertransfection efficiency and was no longer responsive to LIF or other cytokines which can direct ES cell self-renewal via stimulation of LIFR. LRK1 cells were routinely maintained in the presence of IL6 and sIL6R, which allowed stimulation of ES cell self-renewal via gp130 (Yoshida et al., 1994).

Library Construction

Co-cultures of γ-irradiated primary mouse embryonic fibroblasts and ES cells (ZHTc6 cells; Niwa et al 2000) were initiated and maintained in standard ES cell medium lacking cytokines. The number of cells in the co-cultures was such that the MEFs formed a confluent monolayer and the ES cells were seeded such that they would be in excess of the MEFs after 3 days of growth. Staining of a representative plate for Alkaline phosphatase (a marker of ES cells) allowed estimation of the numbers of ES cells present at the time of cell lysis. This gave a ratio of ES RNA/MEF RNA of 12:1. RNA was prepared from 20 F180 flasks of cells and polyadenylated RNA was prepared. RNA quality was monitored by examining a Northern blot for LIFR transcripts; only RNA producing a sharp 11 kb band with no detectable degradation was used further. cDNA was synthesized from polyadenylated RNA by oligo d(T) priming using reagents supplied in the Superscript plasmid system for cDNA synthesis and plasmid cloning (Life Technologies). cDNA was fractionated on a polyacrylamide gel and after recovery of cDNA>1 kb by electroelution, cDNA was ligated into XhoI/NotI digested pPyCAGIP. A library of $7.4 \times 10^5$ primary recombinants was produced after electroporation of E.coli strain DH10B. DNA was prepared from bacteria after overnight growth on 15 cm diameter petri dishes seeded with 5×10⁴-10⁵ colonies each.

Library Screen

DNA (25 µg) from either library or empty vector was introduced into LRK1 cells (6×10⁶) by electroporation and cells were seeded at 10⁶/9 cm dish or 5×10⁴/9 cm dish and cultured in IL6/sIL6R. After 2 days, medium was changed to include puromycin and the cytokine was withdrawn from the high density plates. Cytokine was maintained on the low density plates to monitor transfection efficiency. Medium was changed every 2 days until 9 days post transfection. At this time there were no cells alive on the mock transfected plates and the plates transfected with empty vector alone contained only differentiated cells. In contrast, some of the plates transfected with library DNA contained colonies which appeared morphologically to resemble undifferentiated cells. Extrachromosomal DNA was therefore prepared from the cells on these plates and transferred to *E.coli* DH10B. DNA was prepared from pools of 10⁴ bacterial colonies and this was re-introduced into LRK1 cells and the selection process described above repeated. Of 10 pools screened 2 appeared positive and extrachromosomal DNA was prepared from these 14 days post-transfection. DNA from one of these pools was further examined as detailed below. After transfer to *E.coli* DH10B, DNA from a pool of approximately 250 colonies was prepared, re-introduced into LRK1 cells and the selection process repeated. DNA was prepared from cells 14 or 19 days after transfection. These were transferred to *E.coli* DH10B and 12 miniprep DNAs prepared from the DNA harvested at 14 days post transfection and 9 minipreps prepared from the DNA harvested at 19 days post-transfection. These DNAs were sequenced using an oligonucleotide located upstream of the 5'cloning site.

Confirmation of Results

Sequence analysis of the 9 DNAs prepared 19 days post transfection indicated that one of these plasmids contained a partial cDNA, one gave an uninterpretable sequence and 2 gave the same sequence which matched a full length sequence in the Genbank database. Four of the remaining 5 plasmids lacked a cDNA insert and contained deletions to within 2 base pairs of each other within the IRES. The final plasmid lacked a cDNA insert and had a deletion which removed a further 275 base pairs from the IRES. To confirm that some of these plasmids conferred the self-renewal activity a pool containing equal weights of all 9 plasmids was prepared and transfected into LRK1 cells and subjected to the selection process described above. In contrast to cells transfected in parallel with an empty vector control, which all differentiated, cells transfected with the pool of 9 plasmid DNAs exhibited an undifferentiated morphology. To determine which of the 9 plasmids conferred the self-renewal activity individual plasmids was transfected into LRK1 cells and the selection process described above repeated. Plasmids carrying the partial cDNA, the uninterpretable sequence as well as representatives of either of the 2 classes of deletion within the IRES failed to confer self-renewal activity. In contrast both of the two plasmids which matched the full length sequence in the Genbank database re-capitulated the self-renewal phenotype. This was judged both morphologically and by sustained expression of the marker alkaline phosphatase for 10 days.

Sequence analysis of the 12 DNAs prepared 14 days post-transfection, showed that 4 of these matched the same sequence as the 2 plasmids detailed above. One of these was transfected into LRK1 cells and possessed the ability to confer cytokine-independent self-renewal as judged by the maintenance of an undifferentiated colony morphology, sustained expression of alkaline phosphatase for at least 14 days and sustained Oct4 expression for at least 8 days. Furthermore, a comparison of transfections of the PDF cDNA with a similar plasmid in which the cDNA sequences were restricted to the open reading frame showed PDF activity to lie within the ORF.

EXAMPLE 2

Reversible Expression of a Pluripotency Determining Factor (PDF) Transgene

In order to demonstrate that the acquisition of a cytokine independent pluripotential phenotype caused by expression of PDF in ES cells was reversible a transgene was made in which the transcription unit encoding PDF could be excised by site-specific recombination.

Figure 2:
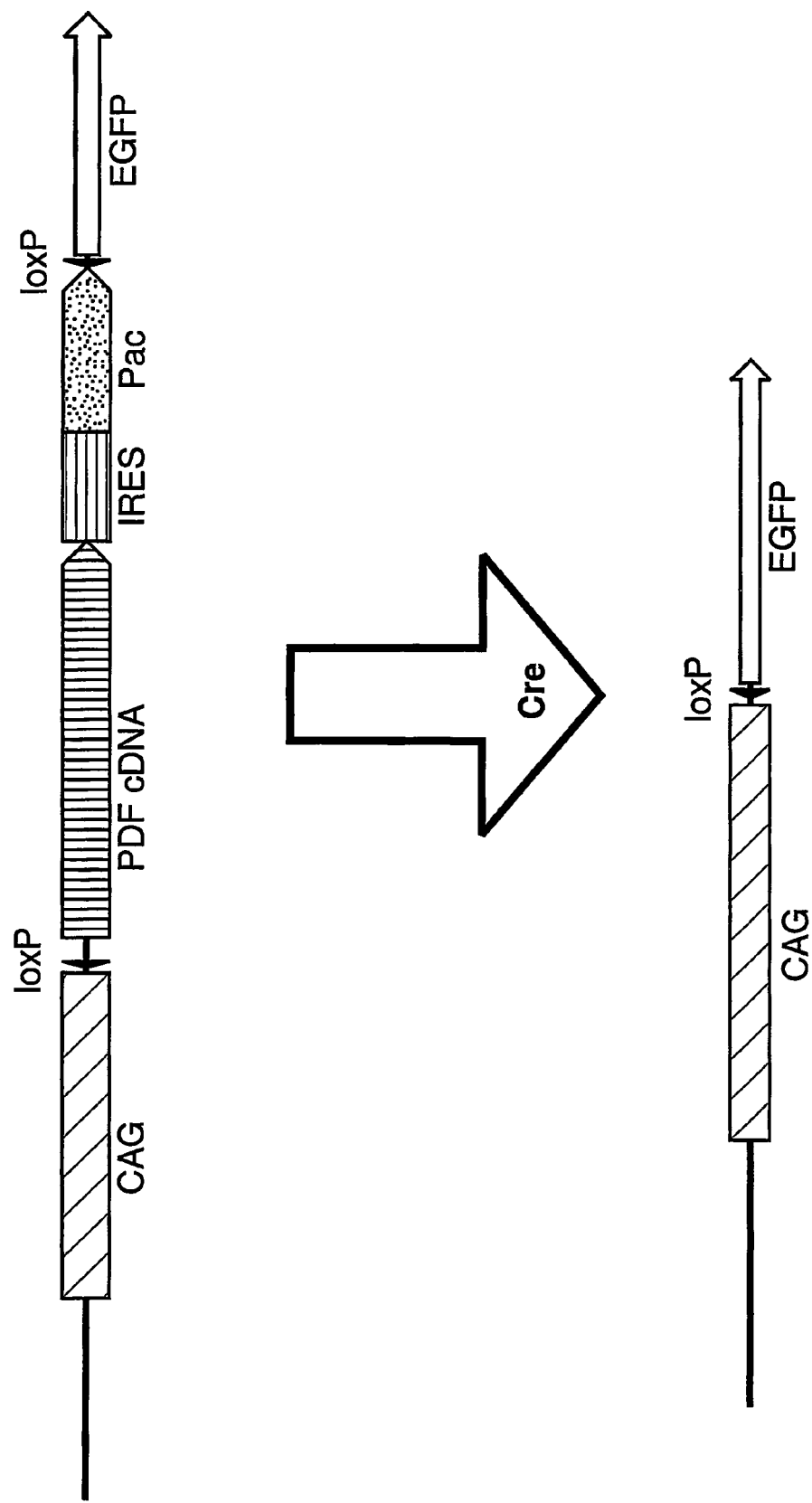
FIG. 2 shows integration and subsequent removal of a loxP flanked pluripotency determining factor transgene.

As a starting point, a plasmid encoding PDF identified in the initial library screen was modified by placing a loxP site between the promoter and the translation initiation codon of PDF and a second loxP site after the polyadenylation signal. The downstream loxP site was followed by the coding sequence of a GFP indicator gene and a polyadenylation signal. In this way, cells which had excised the loxP flanked PDF gene could be identified by their altered fluorescent colour (see FIG. 2)

The plasmid encoding PDF was linearised in the vector backbone and transfected into germ-line competent E14Tg2a cells. Cells were selected for growth in medium lacking gp130 stimulating cytokines. Individual clones were checked for green fluorescence and non-fluorescent clones were expanded in the absence of cytokine for 2 weeks. To eliminate the self-renewing effects of juxtacrine LIF family members, the LIF antagonist hLIF-05 was added to the medium during this period. Thereafter, the culture was split in two. The first of these cultures was maintained as before while the other was maintained in LIF and transfected with a plasmid encoding Cre (pCAGGCreGS). After 2 days, the cells were plated at low density and individual colonies examined microscopically. Green fluorescent colonies were expanded and their genomic DNA analysed to confirm excision of transgenic PDF sequences.

Cells carrying both the floxed PDF gene or the excised transgene were then injected into blastocysts separately and the recipient blastocysts transferred to foster mothers. At various times thereafter, embryos were dissected and analysed. Fluorescence microscopy allowed determination of the contribution of cells carrying the excised transgene to fetal tissues of all three germ layers. Some chimaeras were allowed to be born and subsequently mated to demonstrate germline transmission from the manipulated ES cells.

EXAMPLE 3

Analysis of the Expression of PDF mRNA in Pluridotent Cells

Northern blotting analysis demonstrates that PDF mRNA is expressed in EC and ES cells but not in cell lines which are not pluripotent such as NIH3T3 fibroblast cells and B9 myeloid cells. Moreover, PDF expression decreases when ES cells are induced to differentiate by addition of retinoic acid to the cultures. In situ hybridisation experiments indicate that PDF mRNA is present in the inner cell mass of embryos at day 3.5 of development but not in later blastocysts nor in egg cylinder stage embryos. Therefore, expression correlates with cells which are either themselves established pluripotent stem cell lines or are embryonic pluripotent cells from which stem cells can be established.

Figure 4A:
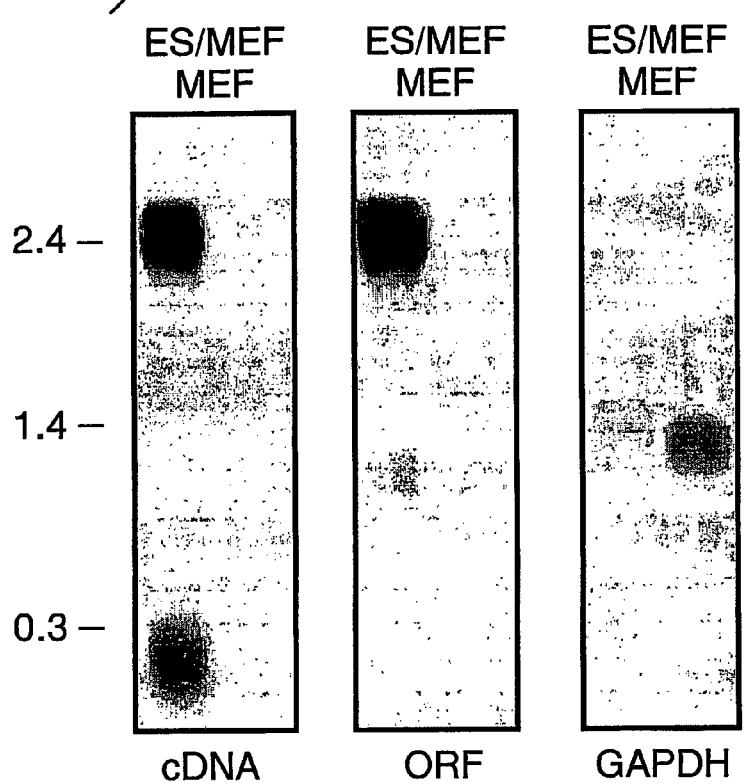
Figure 4B:
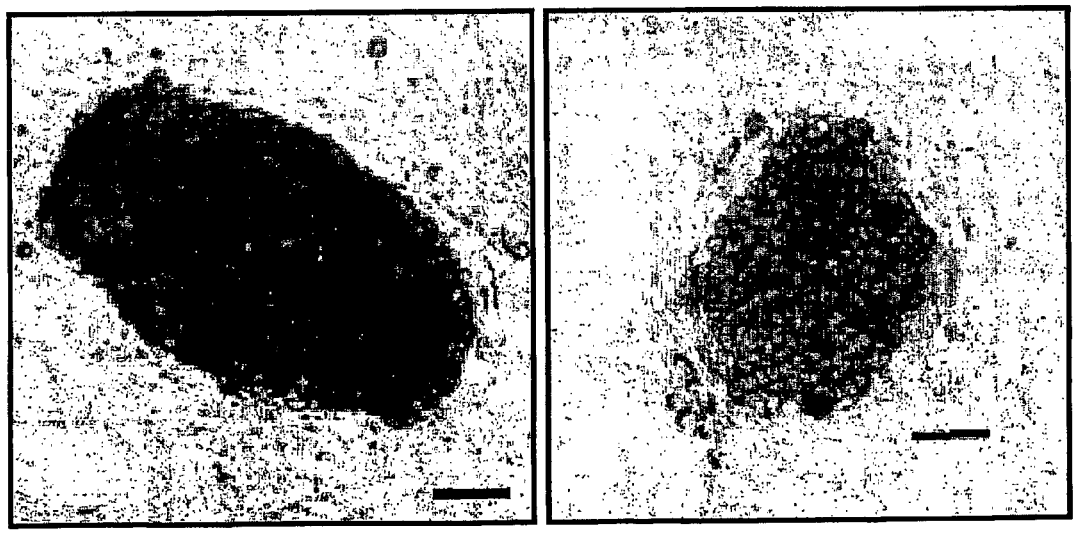

Thus, analysis by Northern blotting confirmed that PDF mRNA is expressed in ES cell/MEF co-cultures from which the cDNA library was synthesised (FIG. 4A). This analysis also confirmed hybridisation of the PDF cDNA to small B2 transcripts. The B2 hybridisation was eliminated when a probe restricted to the PDF ORF was used. Therefore, subsequent Northern and in situ analyses utilised the ORF probe. Expression was not detected in MEFs alone, nor was there any evidence of induction of PDF expression in fibroblasts co-cultured with ES cells (FIG. 4B). This indicates that the ES cells in the co-culture were the source of PDF cDNA. Analysis of several cell lines indicated that PDF expression was highly restricted, being undetectable in parietal endoderm, yolk sac, fibroblast and haematopoietic cells (FIG. 4C). Expression was detected in ES cells, EG cells and in both LIF dependent (PSA4) and LIF independent embryonal carcinoma cell lines.

Figure 4E:
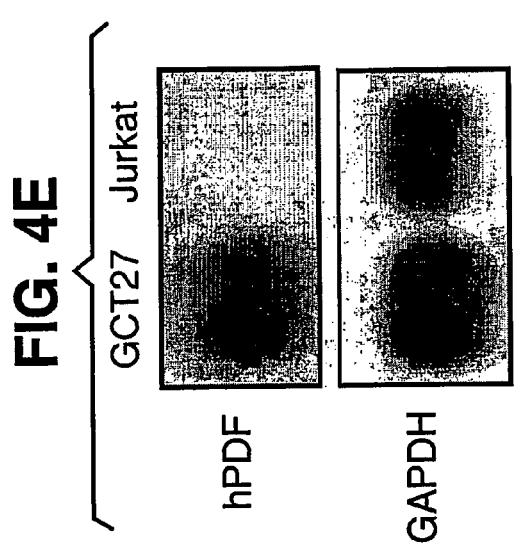
Figure 4F:
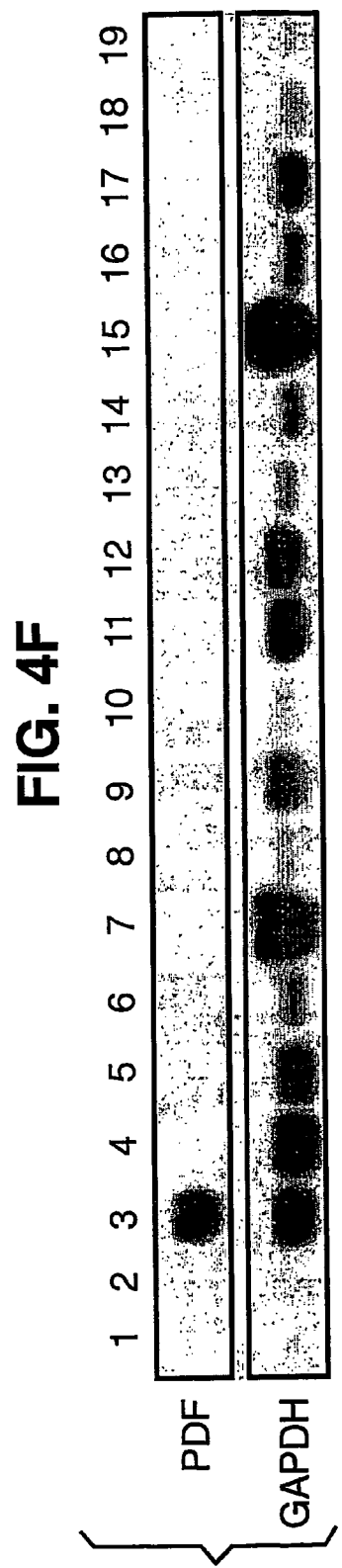

Examination of the human orthologue of PDF showed the corresponding mRNA to be expressed in an embryonal carcinoma cell line but not in a lymphoid cell line (FIG. 4E). Several adult mouse tissues were surveyed for PDF mRNA but no expression was detectable by Northern hybridisation of total RNA (FIG. 4F). The expression of PDF mRNA during ES cell differentiation was next analysed. Whether through induced differentiation by retinoic acid or 3-methoxy-benzamide treatment, the level of PDF mRNA was rapidly reduced (FIG. 4D). Examination by in situ hybridisation of ES cell cultures in which the LIF level was reduced in order to allow the formation of colonies with a mixture of differentiated and undifferentiated cells showed that PDF expression was restricted to the undifferentiated cells (FIG. 4B).

Pdf mRNA is found in pluripotent ES and EG cells and also in both mouse and human EC cells, but appears to be absent in other types of cell line (FIG. 4 and data not shown). Pdf expression is down-regulated early during ES cell differentiation consistent with an intimate association with pluripotent stem cell identity.

EXAMPLE 4

Maintenance of Pluripotent Human Embryonic Stem Cells in the Absence of Feeders/Feeder Extract Human ES cells are cultured on a feeder layer of γ-irradiated mouse embryonic fibroblast (MEF) in 80% DMEM medium, supplemented with 100 units/ml LIF, 1 mM glutamine, 0.1 mM 2mercapto-ethanol, 1% nonessential amino acids, 4 ng/ml basic fibroblast growth factor and 20% KnockOut SR (a serum-free formulation) (GIBCO-BRL).

The plasmid shown in FIG. 1 (as well as a similar plasmid in which the mouse PDF sequence is replaced by a human PDF sequence) is linearised in the vector backbone and transfected into human ES cells. The transfection utilises the ExGen 500 method described in Eiges et al. except that the protocol is scaled up to use $10^7$ human ES cells. The day after transfection, the cells are trypsinised and split in two. One half of the cells is plated onto a layer of Puromycin resistant MEFs at a density of $10^4/cm^2$; the other half is plated onto Puromycin sensitive MEFs at a density of $10^4/cm^2$. Two days after replating, the cells on the Puromycin sensitive MEFs are trypsinised and plated onto gelatinised plastic dishes at $10^4/cm^2$. Puromycin is added to both sets of cultures and medium replaced every 3-4 days. After approximately 14 days several of the Puromycin resistant human ES cell colonies growing on feeders are tested for their ability to grow in the absence of a feeder layer by trypsinisation and direct plating onto gelatin coated plates.

Puromycin resistant ES cell lines are assessed for their ability to be serially passaged and subcloned in the absence of a feeder layer over the course of 6 weeks.

The differentiation potential of these cells is then tested (Eiges et al. 2001) following excision of the floxed PDF expression cassette as described.

EXAMPLE 5

Characterisation of the PDF cDNA

Figure 3A:
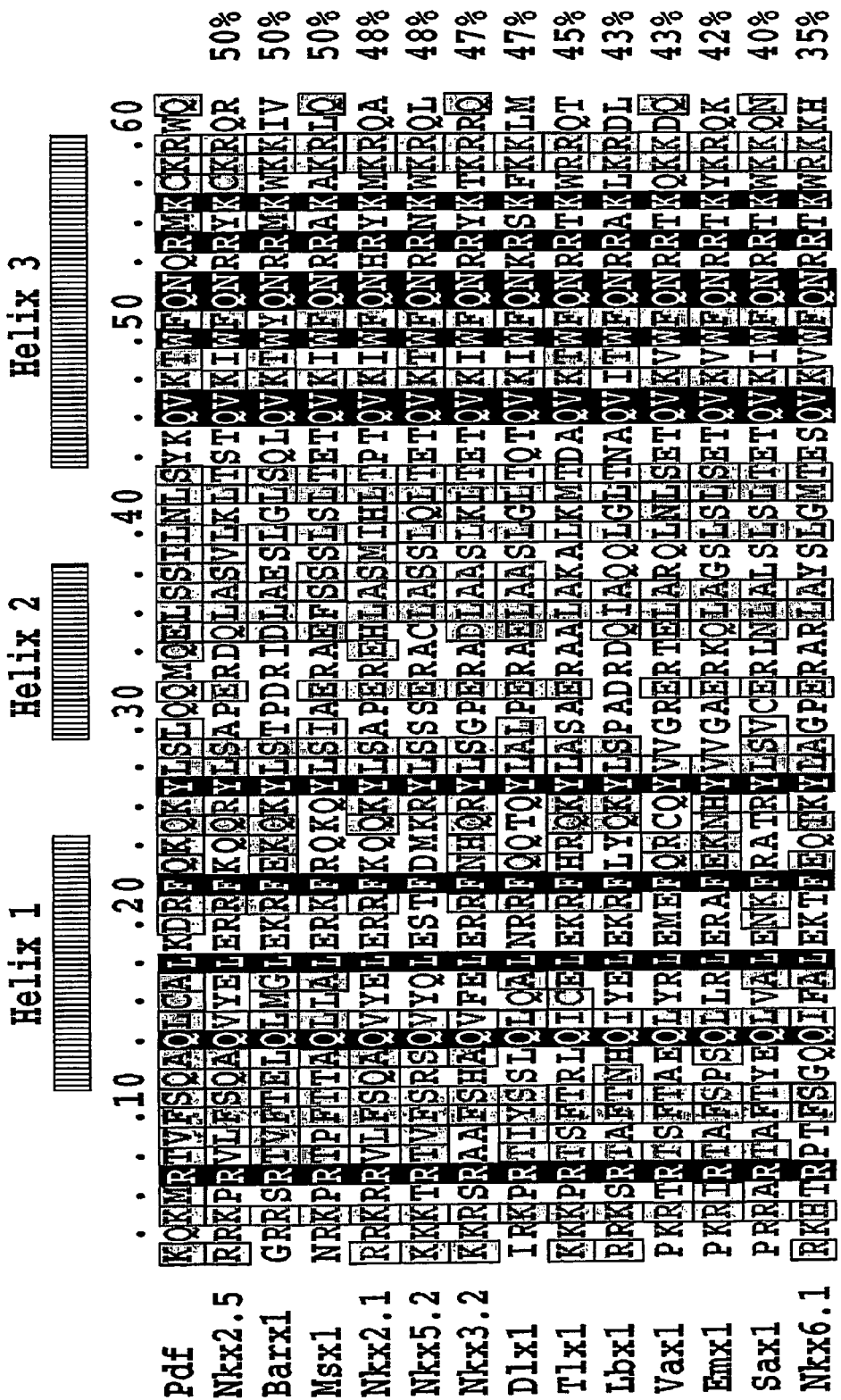

A search for recognisable domains in the PDF sequence using SMART (smart.embl-heidelberg.de (Letunic et al., 2002; Schultz et al., 1998)) revealed the presence of a homeodomain between amino acid resides 96 and 155, with no other obvious relationship to previously characterised proteins. Further analysis by BLAST revealed that PDF was most closely related to several members of the NK2 family. However, in no case was this identity greater than 50% (FIG. 3). Therefore, PDF is either the founding member of a novel homeodomain family or is a unique variant homeodomain (Shashikant et al., 1991).

A comparison of PDF with the most closely related human sequence revealed overall identity of 60%. Sequence conservation was most pronounced over the homeodomain where the two sequences were 87% identical (FIG. 3B). This far exceeds that the level of identity seen between the homeodomains of PDF and other mouse proteins, indicating that this is the human orthologue of PDF. Of the 8 non-identical amino acids 6 are located in the N-terminal arm around a-helix 1, regions of the homeodomain considered to be more loosely associated with the DNA target. Outwith the homeodomain there are 4 regions in which a contiguous stretch of more than 4 amino acid residues is conserved. Of these conserved regions only one, a serine rich motif, is N-terminal to the homeodomain, the remainder lying C-terminal to the homeodomain. The human sequence contains an insertion of seven amino acids between the first and second of these C-terminal identity motifs. In the mouse sequence, between the homeodomain and the C-terminal conserved sequences there is a 46 amino acid stretch in which every fifth residue is tryptophan. Moreover, within this sequence the first 31 amino acids represent a simple reiteration of the sequence WnsQTWTNPTW (n=G,S,N and s=S,N). The conservation of the sequence in the human is less striking and contains a short deletion relative to the mouse sequence. Yet with the exception of the $16^{th}$ residue every fifth residue remains tryptophan.

In the 3'UTR of the PDF mRNA there is a B2 repetitive element oriented in the opposite transcriptional direction to PDF (FIG. 3C). Whether this sequence is transcribed by RNA polymerase III is not clear although the sequence of the split promoter suggests that it may be (Galli et al., 1981). Since B2 elements are expressed at high levels in embryonic cells (Ryskov et al., 1983) it is possible that the presence of the B2 within the 3'UTR of PDF mRNA may contribute to the regulation of PDF gene expression either directly through transcriptional interference or by more indirect means.

EXAMPLE 6

Analysis of hPDF Function in Mouse ES Cells

The ability of the human PDF orthologue to replicate the activity of mouse PDF was tested by placing the human ORF in the pPyCAGIP vector and transfecting mouse ES cells. This shows that the human sequence was capable of directing cytokine independent self-renewal of mouse ES cells (FIG.

3). This activity was reduced compared to mouse PDF, presumably due to the considerable sequence divergence. The specificity of the effect of PDF was tested by a similar experiment in which the ORF of one of the mouse homeobox genes most closely related to PDF (Nkx2.5) was expressed in ES cells. In this case no cytokine independent self-renewal was evident; in fact the resultant cells appeared morphologically differentiated even in the presence of LIF. This indicates that cytokine independence is specifically conferred by PDF and is not a common attribute of homeodomain proteins.

EXAMPLE 7

In Vivo Expression of mPDF

Figure 5B:
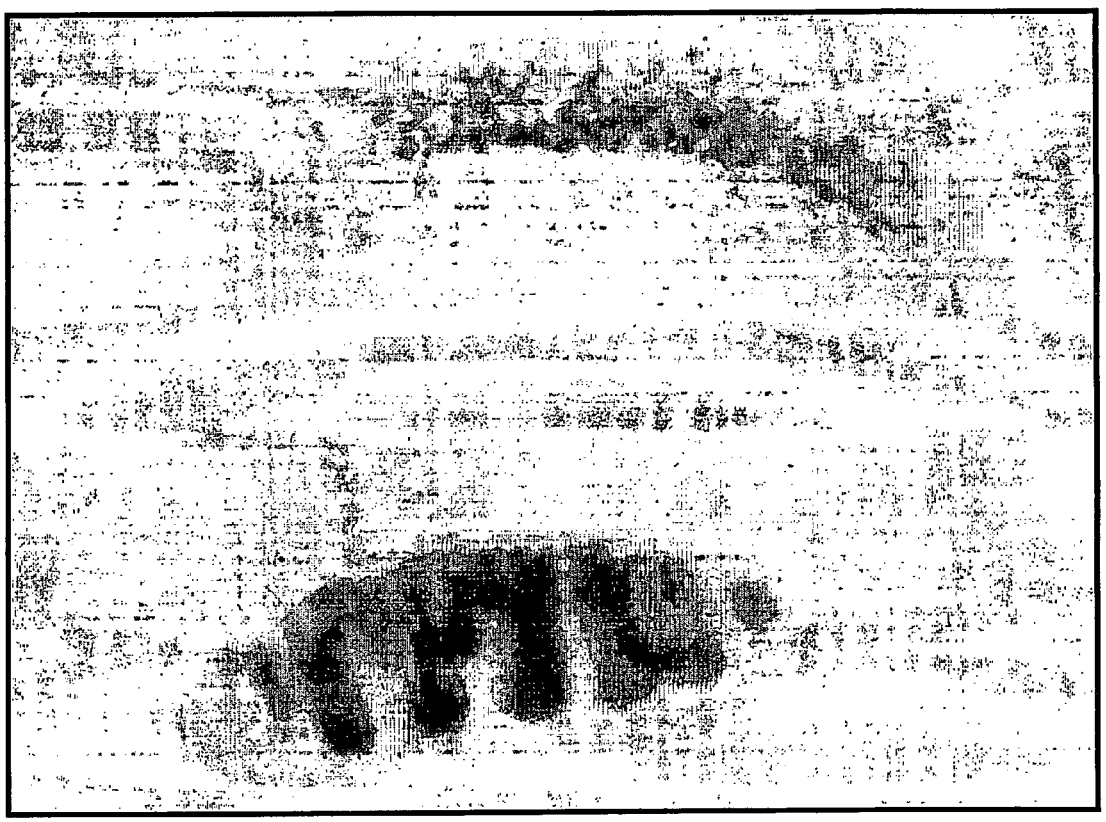

We examined distribution of PDF mRNA in vivo (FIG. 5). No expression is seen during early cleavage stages. The first sign of PDF mRNA expression is in compacted morulae. It is striking that the hybridisation signal is localised to interior cells, the future inner cell mass. In the E3.5 blastocyst expression is confined to the cells of the inner cell mass and is absent from the trophectoderm. In later blastocysts PDF mRNA is further restricted to the epiblast and is excluded from the primitive endoderm. PDF transcripts appear as a temporal wave with maximal levels between the late morulae and the mid blastocyst. In blastocysts about to implant, the PDF mRNA level has dropped below the level of visualisation. Significantly, however, transcripts remained detectable in the epiblast of blastocysts in diapause. We also examined PDF expression in primordial germ cells as these can be converted into pluripotent EG cells (Matsui et al., 1992). Expression is not evident in the migratory germ cells at E8.5 but PDF mRNA is readily detectable in the genital ridges of E11.5 embryos in a pattern indicative of localisation to the primordial germ cells (FIG. 5B).

EXAMPLE 8

Relationship of PDF with Other Known Mediators of Pluripotency.

The dose response of ES cells to increasing levels of PDF was assessed by episomal expression in LRK1 cells. This was achieved by transfection of episomal constructs directing differing levels of cDNA expression (FIG. 8A). The proportion of the resulting colonies that could self-renew in the absence of cytokine correlated with the level of expression expected from the episomes based on similar studies measuring gfp expression levels (data not shown). Furthermore, as observed for cells carrying integrated PDF transgenes, the addition of LIF to cultures of cells carrying PDF episomes augments self-renewal as assessed both in terms of the number of self-renewing colonies formed and also colony morphology. Essentially identical results were obtained by transfection of the same DNAs into the CCE derived polyoma large T expressing cell line MG1.19 (Gassmann et al., 1995).

Figure 8B:
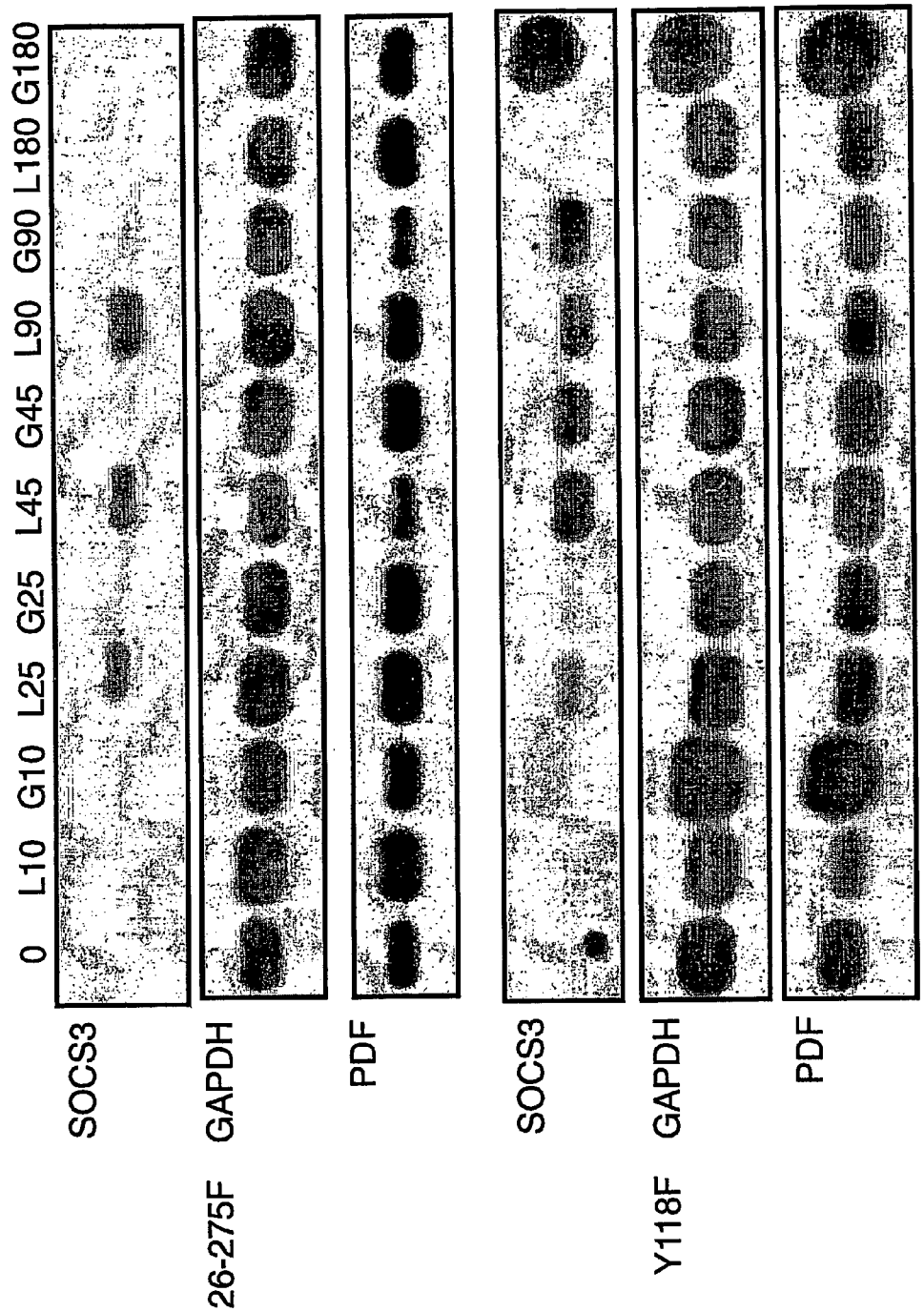

We investigated whether the co-operative effect of the gp130 signal and PDF overexpression is due to the PDF gene being a transcriptional target of STAT3. Using chimaeric receptors in which the intracellular portion of gp130 is linked to the extracellular portion of GCSF-R it is possible to investigate STAT3 targets in ES cells. An analysis of the eight known SOCS family members, which are all potential STAT targets, indicated that only SOCS3 is significantly stimulated in ES cells by LIF (FIG. 8B and data not shown). This stimulation does not occur when the four STAT binding sites in the receptor are prevented from binding STAT3 by mutation from tyrosine to phenylalanine (FIG. 8B). In contrast, SOCS3 induction is enhanced and sustained when the negative regulatory tyrosine is similarly mutagenised, a result consistent with the sustained STAT3 activation observed in these cells (Burdon et al., 1999). In contrast to the situation with SOCS3, no induction of PDF expression is evident upon LIF stimulation nor upon G-CSF stimulation of cell expressing chimaeric receptors (FIG. 8B).

EXAMPLE 9

Relationship of PDF with Oct 4

The ability of PDF to substitute for Oct4 in self-renewal of ES cells was then tested using ZHBTc4.1 cells. These cells carry two null alleles for Oct4 but their self-renewal can be sustained due to the presence of a doxycycline responsive Oct4 transgene (Niwa et al., 2000). When the expression of the Oct4 transgene is repressed by administration of doxycycline, the cells differentiate. ZHBTc4.1 cells were transfected with linearised pPyCAGIP sequences carrying no insert, Oct4 or PDF. As previously documented, this Oct4 plasmid prevents the differentiation caused by doxycycline induced repression of the Oct4 transgene (Niwa et al., 2002). However, the PDF expression vector could not (FIG. 8C). Therefore, although PDF can sustain the ES cell phenotype in the absence of gp130-mediated gp130 stimulation, it cannot do so in the absence of Oct4.

EXAMPLE 10

ES Cell Identity is Faithfully Maintained by PDF Expression

Figure 6A:
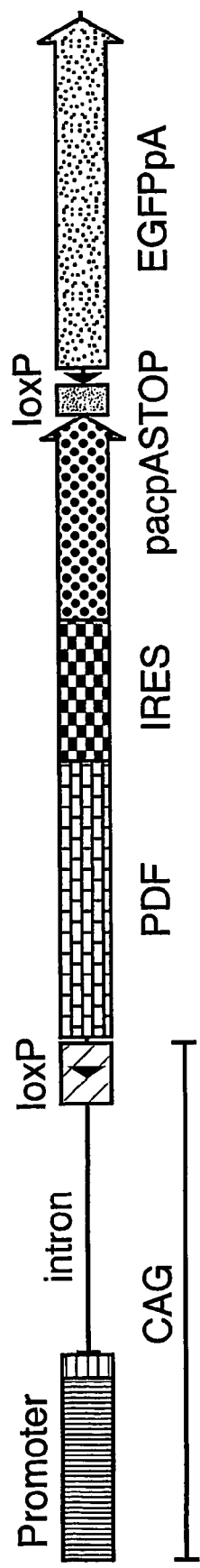

We investigated the consequences of PDF transfection in ES cells that do not contain polyoma LT. A loxP containing construct was employed such that the PDF cDNA could subsequently be excised by Cre recombinase. Following isolation of stable integrants, site specific recombination can then be used to remove the PDF ORF and simultaneously bring GFP under CAG promoter control (FIG. 6A). The excision of the PDF transgene allows assessment of any genetic or epigenetic changes to the cells caused by temporary transgene expression. In these experiments we aimed to test the ability of cells overexpressing PDF to be propagated clonally in the absence of gp130 signalling. We wished to examine two issues; firstly, whether enforced PDF expression prevented differentiation in a range of circumstances and secondly, whether pluripotency and embryo colonisation capacity could be sustained in the absence of gp130 signalling.

Figure 6B:
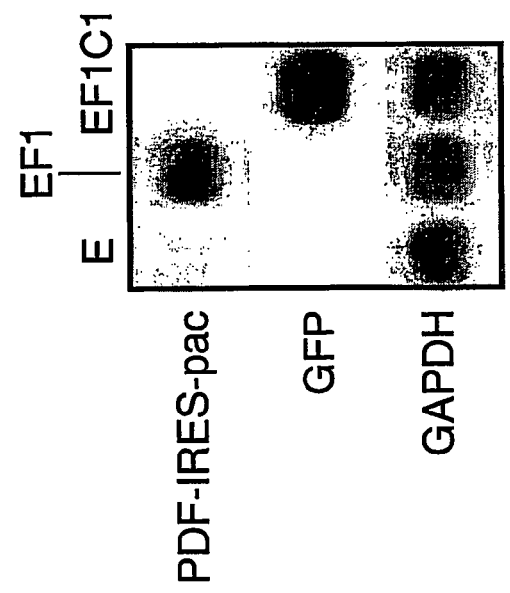

Clonal transfectants were isolated by selection in puromycin and expression of PDF transgene mRNA was confirmed by Northern analysis (FIG. 6B). Cells were seeded at low density and expanded in the presence of the LIF antagonist, hLIF-05 (Vernallis et al., 1997) for at least 7 days through two passages. hLIF-05 blocks the ability of all known LIF-R ligands to engage the LIF-R/gp130 complex. Parental cells treated in parallel produced only differentiated cells that failed to expand. In contrast, lines containing the floxed PDF-IRES-pac cassette maintained an undifferentiated morphology and continued to proliferate.

Subsequently, LIF was added and cells were transiently transfected with Cre. Colonies in which the PDF expression cassette had been eliminated were identified by expression of GFP and a restoration of puromycin sensitivity. This procedure was performed using two independent ES cell lines E14Tg2a and ZIN40. Chromosomal spreads were examined for several of the resulting clones and in all cases were found to be predominantly 40XY.

Figure 6C:
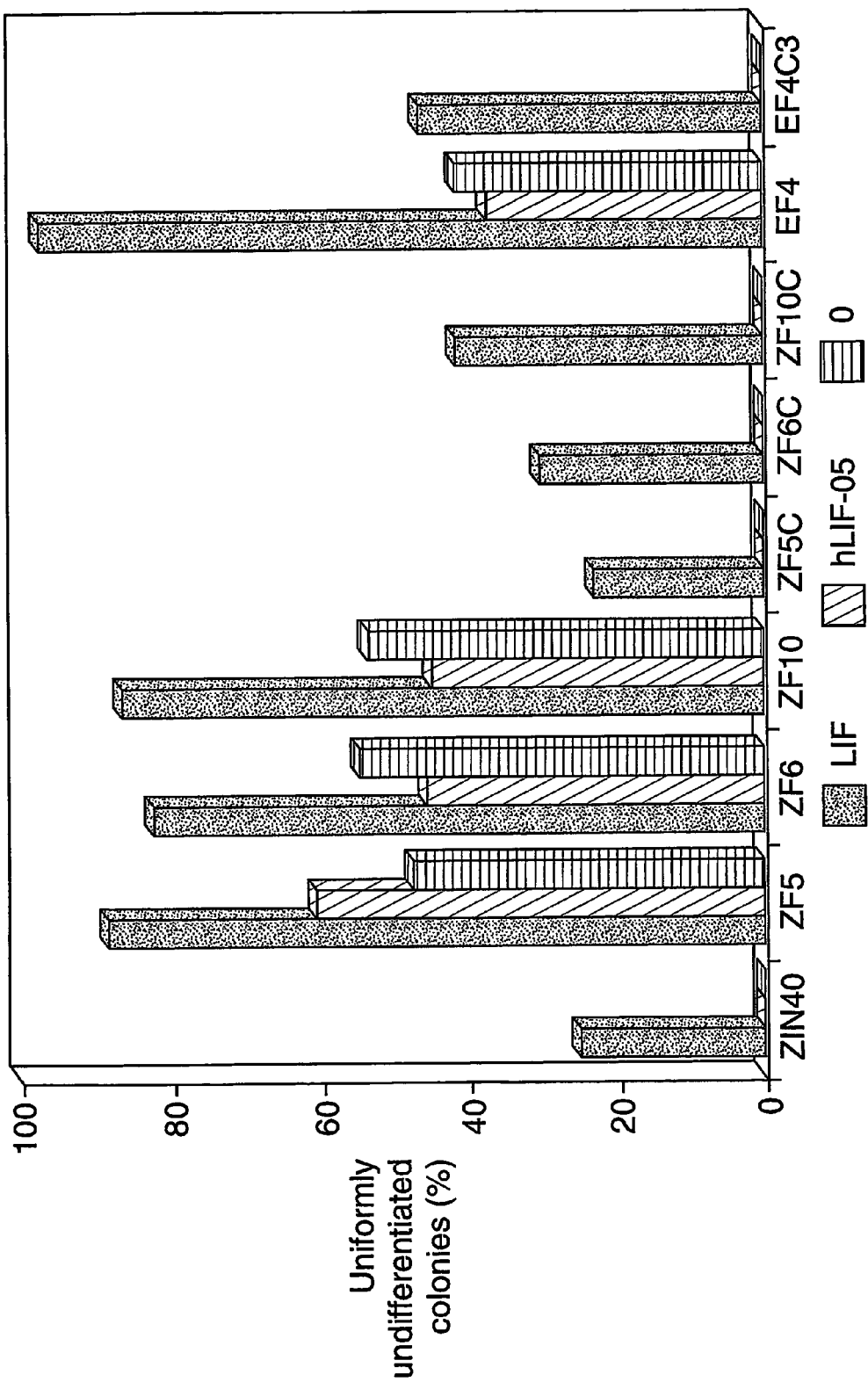

Colony forming assays were performed as a rigorous assessment of the phenotype of PDF transfectants and their Cre-treated derivatives. Cells were plated at clonal density in medium supplemented with LIF, without LIF or with the LIF antagonist hLIF-05. After culture for 6 days, plates were stained for alkaline phosphatase activity and the proportion of colonies consisting solely of undifferentiated cells quantitated (FIG. 6C). Neither the parental nor the GFP expressing cells formed any fully undifferentiated colonies in the absence of LIF or in the presence of the LIF antagonist. PDF transfectants, however, generated appreciable numbers of such pure stem cell colonies. Upon addition of LIF this proportion rose to >80% of colonies. Following Cre mediated excision of the transgene this enhanced response to LIF was also lost.

Figure 6D:
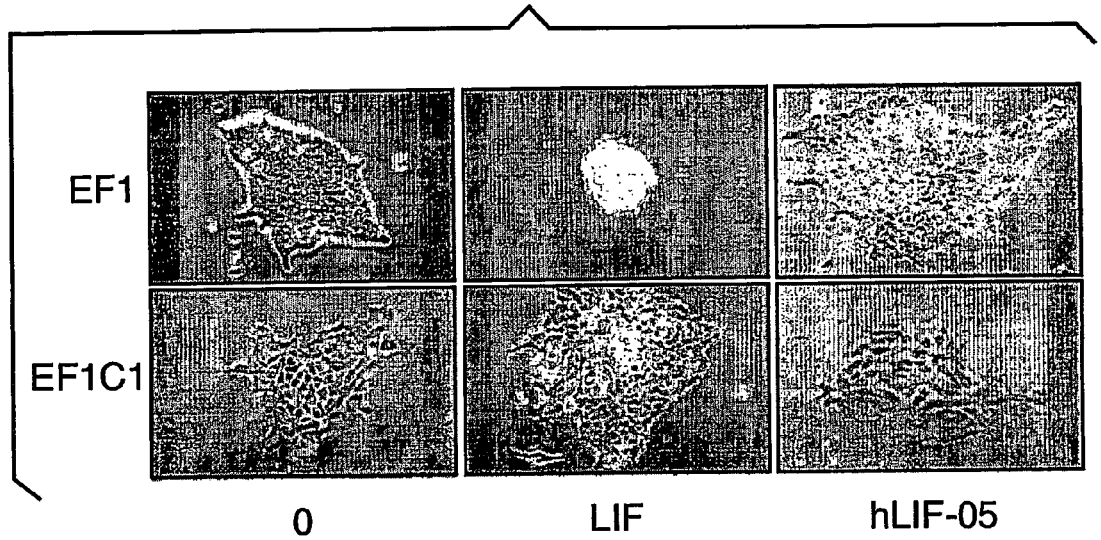

The difference in the proportion of cells expressing the PDF transgene forming fully undifferentiated colonies in the presence or absence of LIF is accompanied by a change in the morphology of the colonies (FIG. 6D). In both cases the colonies are composed of small undifferentiated cells with a scant cytoplasm and prominent nucleoli. Without LIF, the PDF expressors grow as a monolayer and are essentially indistinguishable from parental or Cre-treated derivative ES cells cultured in the presence of LIF. The combination of LIF plus PDF expression, however, causes the colonies to adopt a tightly compacted morphology in which the cells preferentially adhere to one another rather than grow out over the substratum. This resembles the "classical" appearance of ES cells cultured on feeder layers.

Figure 6E:
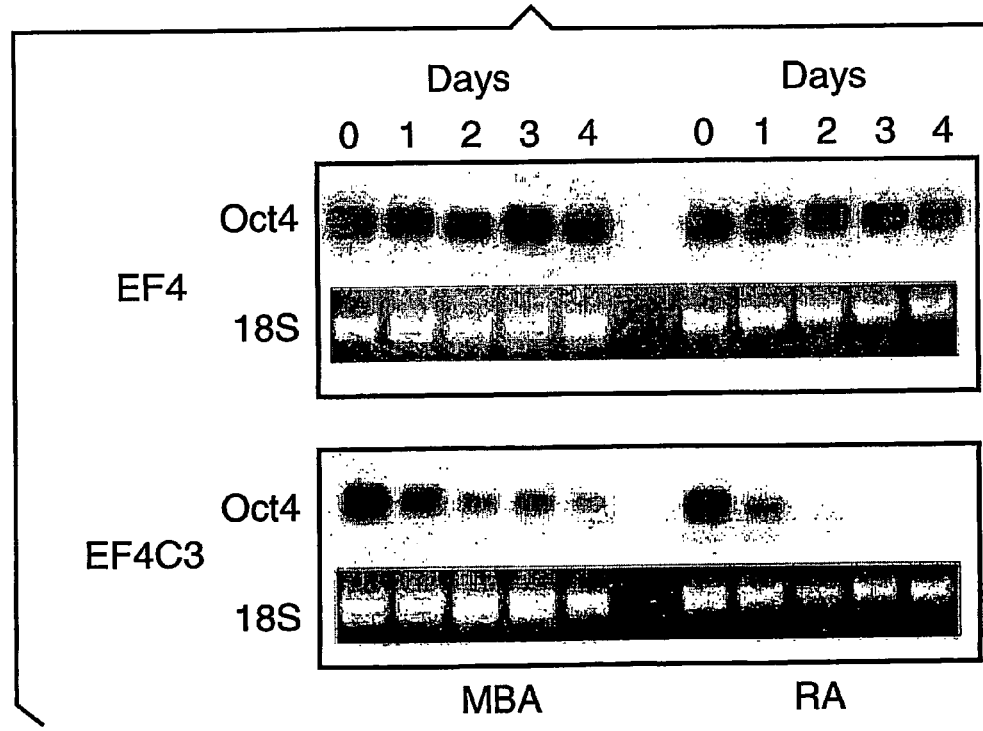

Forced expression of PDF allows ES cells to self-renew in the absence of gp130 stimulation, culture conditions in which the parental cells differentiate. We next determined whether PDF expressor cells would self-renew or differentiate when exposed to agents that normally cause differentiation. When cultured for four days following exposure to 3-methoxybenamide (MBA) or all-trans retinoic acid (RA), PDF expressing cells retained an undifferentiated appearance, whereas cultures of both the GFP derivatives and the parental cells underwent morphological differentiation (data not shown). These morphological features are reflected at the molecular level in continued expression of Oct4 by PDF expressors compared with dramatic down-regulation in Cre derivatives (FIG. 6E). These data establish that PDF transfectants are refractory to cues that normally direct differentiation in monolayer cultures but that following transgene excision differentiation capacity is restored.

Figure 7B:
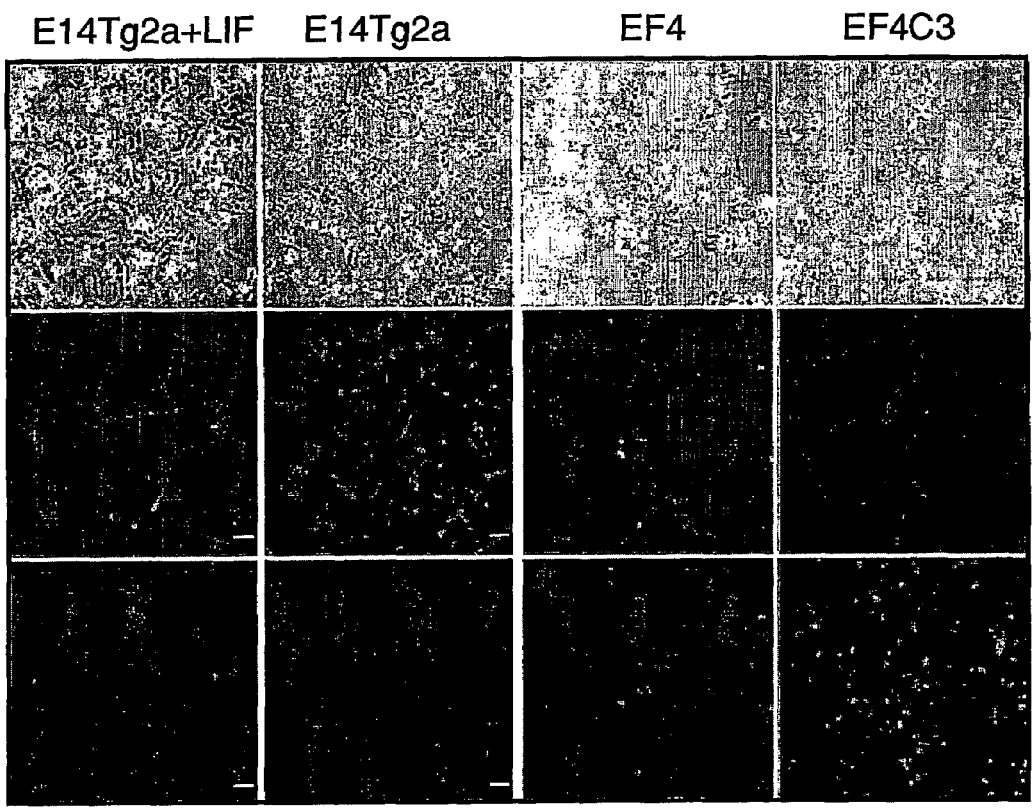

The ability of PDF expressing cells to respond to cellular interactions that induce differentiation was then investigated by aggregation in suspension culture, conditions that lead to formation of multidifferentiated embryoid bodies from parental ES cells (Doetschman et al., 1985). After eight days in aggregation culture, embryoid bodies were plated singly per well of a 48 well dish and subsequently scored daily for spontaneous contractions, an indicator of cardiomyocyte differentiation. FIG. 7A shows that the incidence of cardiogenesis is reduced by approximately 50% in PDF expressors relative to their Cre derivatives. Furthermore, the emergence of cardiac cells from PDF expressors is retarded relative to their Cre derivatives. In fact the graph in FIG. 7 underestimates the difference between the two classes since wells derived from cells expressing the floxed transgene contained only small beating areas whereas wells derived from the Cre derivative cells had extensive beating areas, in some cases covering the whole outgrowth. Embryoid bodies were also exposed to retinoic acid for the last 4 days of aggregation culture and plated out under conditions favouring neuronal differentiation (Bain et al., 1995; Li et al., 1998). E14Tg2a cells formed large numbers of cells of neuronal morphology that expressed neuron-specific type III b-tubulin (TuJ) (FIG. 7B). The continuous presence of LIF inhibited differentiation of TuJ positive cells. Emergence of TuJ positive cells was also blocked in cultures derived from ES cells expressing the floxed transgene, but was restored in their Cre derivatives. However the appearance of the cells remaining in the wells from the E14Tg2a (+LIF) and EF4 cultures was not identical. The former contained many cells with the morphology of ES cells, whereas the PDF expressors had a more dispersed appearance suggesting that they could be partly differentiated. These observations indicate that ES cells expressing PDF do not undergo differentiation efficiently in multicellular aggregates environment but that some degree of differentiation is still induced. Most significantly, the Cre derivative cell lines appear unaffected by their period of clonal expansion driven by enhanced PDF expression since they possess comparable potential to normal ES cells for differentiation under all conditions examined.

Figure 7C:

Finally, we investigated whether forced expression of PDF circumvents the requirement for LIF-R/gp130 mediated signaling in maintenance of embryo colonisation properties. PDF transfectants (isolated in the absence of LIF and then cultured in the presence of LIF antagonist for over 1 week) from which exogenous PDF sequences had been removed by Cre mediated excision, were injected into mouse blastocysts. To date we have assessed Cre derivative lines from one of the PDF transfectants. Examination of the resulting chimaeras at mid-gestation demonstrated widespread contribution of the cells to tissues of the developing embryos as revealed by GFP expression (FIG. 7C). Similarly injected embryos were brought to term and resulted in the production of live chimaeras (Table 1).

These results establish: (i) that cells expressing the PDF transgene self-renew in a cytokine independent manner; (ii) that LIF acts co-operatively with the PDF transgene to confer enhanced self-renewal capacity; and, (iii) that the effects of PDF transgene expression are fully reversible following transgene excision.

TABLE 1

Live born chimaeras obtained from Cre derivatives of PDF transfectants

| Line | Mice born | Chimaeras |
| --- | --- | --- |
| EF1C1 | 7 | 3 |
| EF1C3 | 21 | 10 |
| EF1C5 | 11 | 11 |

EXAMPLE 11

Expression of PDF cDNA in a Human Pluripotent Cell Line

Figure 9B:
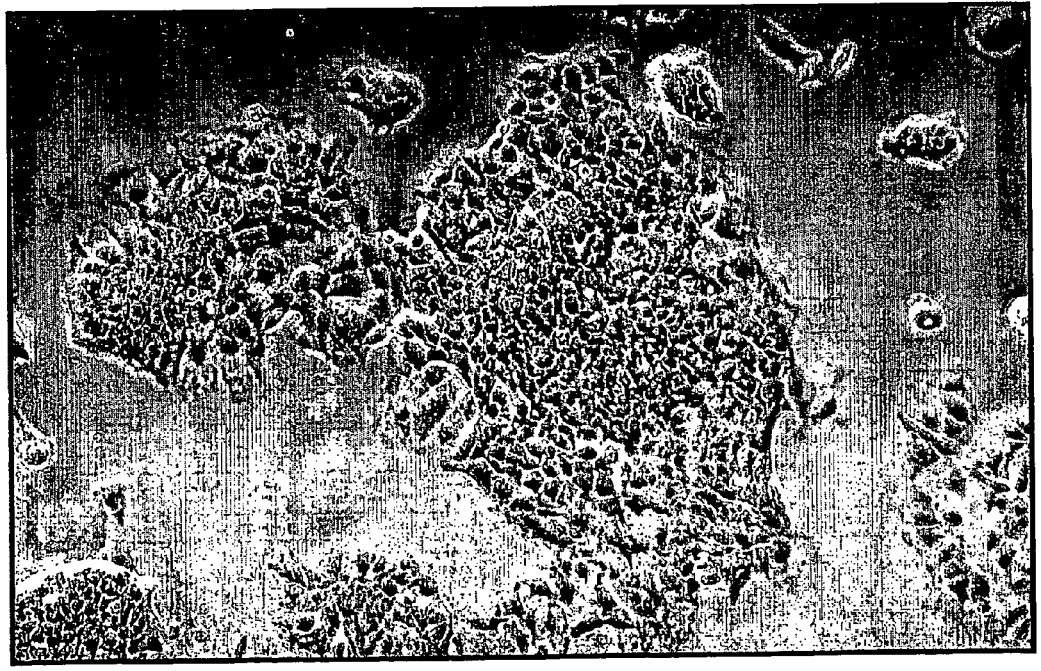
Figure 9C:

In this study, we have demonstrated the factor-dependent maintenance of pluripotentiality following expression of the human cDNA for Pluripotency Determining Factor (hPDF) in a human pluripotent EC cell line. This clonally derived cell line, Germ Cell Tumour 27X-1 (GCT27X-1), kindly provided by Assoc. Prof. Martin Pera, Monash Institute for Reproduction and Development (MIRD), Melbourne, Australia) has been previously shown to give rise to yolk sac, trophoblast, skin, cartilage, glandular epithelium, neurectoderm and other tissues representative of the three primitive germ layers in xenografts. The same cell line also shows spontaneous differentiation in vitro into somatic and extraembryonic cell types (Pera et al., 1998). The GCT 27X-1 cell line is routinely maintained either on a layer of mitotically inactivated mouse STO feeder cells (FIG. 9a) or in the absence of feeder cells with the addition of an uncharacterised factor secreted from the feeder-free culture of a human yolk sac carcinoma-derived cell line, GCT44 (kindly provided by Martin Pera, MIRD, Melbourne, Australia), (FIG. 9b). The withdrawal of this conditioned medium from low and clonal density GCT 27X-1 cell cultures results in their complete differentiation (FIG. 9c).

The hPDF transcription factor is endogenously expressed in pluripotent GCT 27X-1 hEC cells (FIG. 10) and is therefore postulated to play a role in the maintenance of self-renewal in this and other human pluripotent cell lines.

Here we demonstrate the loss of pluripotentiality in GCT 27X-1 feeder-free cell cultures in response to the withdrawal of the yolk sac carcinoma cell-derived conditioned medium and the maintenance of pluripotentiality at a clonal level where exogenous hPDF is expressed.

These findings show that the hPDF transcription factor provides a basis for robust culture systems for human ES cells.

Experimental Strategy

A construct containing a human cDNA sequence encompassing the open reading frame for the hPDF gene was transfected both by lipofection and electroporation techniques into the GCT 27X-1 cells. Stable transfectant colonies were established in the absence of feeder cells, with and without the addition of GCT 44-derived conditioned medium required for the support of hEC cell growth and maintenance. Stable colonies were selected in the presence of the puromycin antibiotic and those showing the maintenance of a tight hEC phenotype (as judged by morphology) were picked and expanded from both conditions. These clonal hPDF-expressing cell lines were subsequently tested at both routine and clonal density for their ability to maintain a pluripotent phenotype in the absence of conditioned medium, with wild type GCT 27X-1 cells and GCT 27X-1 cells transfected with a similar construct but lacking the hPDF sequence as controls.

Definitive undifferentiated hEC cell phenotype in PDF-expressing cells was confirmed by indirect immunofluorescent staining for the marker Cluster Designation 30 (CD30), a member of the Tumour Necrosis Factor receptor superfamily. CD30 is a specific marker of human EC cells and is downregulated during in vitro differentiation (Latza et al., 1995; Pera et al., 1997). There is no evidence for the presence of CD30 on mouse EC or mouse ES cells.

This experimental strategy is outlined in flow chart form (FIG. 11).

Materials and Methodology

Vector Constructs

An 8.8 kb construct, termed Floxed hPDF (FIG. 12a), contains the open reading frame for the hPDF cDNA (~900 bp) operating under a human cytomegalovirus immediate early enhancer (CMV IE) and the human actin promoter, upstream of a bicistronic reporter cassette providing for IRES-mediated expression of the puromycin resistance gene, all encompassed within loxP recombination sites. In addition, the vector contains the enhanced GFP reporter gene downstream of the loxP sites, providing for visualisation by fluorescence where Cre-mediated recombination occurs.

A similar non-floxed construct pPyCAGegfpIP ("GFP control" vector), (FIG. 12b), in which the hPDF sequence in the Floxed hPDF vector is replaced by the enhanced GFP reporter gene upstream of the IRES-puromycin reporter cassette, was used as a control to provide "non hPDF"-expressing transfected hEC cells for each experiment.

hEC Cell Culture

GCT 27X-1 cells were routinely cultured on a feeder layer of mitotically inactivated mouse STO cells in a 1:1 v/v αMEM/Ham's F-12 medium (Invitrogen, Groningen, The Netherlands) supplemented with 2 mM L-Glutamine (Invitrogen), 2.7 g/L sodium bicarbonate (Sigma Chemical Co., St. Louis, Mo., USA) and 10% FCS (Commonwealth Serum Laboratories, CSL, Melbourne, Australia), and maintained at 37° C. with 5% $CO_2$. Cells were passaged each 7 days using digestion with a 5 mg/ml dispase solution (Sigma) prepared in the above medium, and replated at a density of no less than $\frac{1}{10}^{th}$ of the harvest.

For transfection experiments and clonal assays, GCT 27X-1 cells were cultured without STO feeder cells but with the addition of conditioned media obtained from the feeder-free culture of a human yolk sac carcinoma-derived cell line CGT 44 (cells kindly provided by Martin Pera, MIRD, Melbourne, Australia) at 25% v/v in the supplemented αMEM/Ham's F-12 medium described above. Single cell suspensions were prepared by trypsin digestion with a 0.025% trypsin (Invitrogen)/1 mM EDTA (Sigma)/1% chicken serum (Invitrogen) solution prepared in PBS buffer. Clonal density cell cultures were seeded at 200-300 cells/$cm^2$ and low density cultures at 5000 cells/$cm^2$.

The GCT 44 cell line was routinely maintained on mitotically inactivated mouse STO feeder cells in high glucose DMEM medium (Invitrogen) supplemented with 2 mM L-Glutamine (Invitrogen), 3.7 g/L sodium bicarbonate (Sigma) and 10% FCS (CSL), and maintained at 37° C. with 5% $CO_2$ but passaged by digestion with a 0.25% trypsin (Invitrogen)/1 mM EDTA (Sigma) solution prepared in PBS buffer. Conditioned medium was collected on days 7, 10 and 14 from feeder-free cultures, filter sterilized and stored at 4° C. for up to 2 months. Each batch of conditioned medium was tested for the ability to maintain feeder-free clonal cultures of GCT 27X-1 hEC cells as described above (data not shown).

The mouse STO feeder cells (kindly provided by Martin Pera, MIRD, Melbourne, Australia) were routinely maintained in high glucose DMEM medium (Invitrogen) supplemented as above for GCT 44 culture. Routine STO cultures were passaged twice-weekly by digestion with a 0.25% trypsin (Invitrogen)/1 mM EDTA (Sigma) solution prepared in PBS buffer. Mitotic inactivation of STO cells was achieved by incubation of a routine culture for 2-3 hours in a 16 μg/ml Mitomycin-C solution (Sigma) prepared in supplemented DMEM medium (as above) and washed twice with PBS prior to trypsinisation.

For routine morphological examination of hEC cells, cultures were fixed and stained with Leishman's as previously described (O'Brien, 2001).

Cell cultures were routinely inspected by phase-contrast microscopy using either Leica DMIL (Leica Microscopy Systems, Wetzlar, Germany) or Nikon Diaphot 300 (Nikon Inc., Melville, N.Y., USA) microscopes. Fluorescing control GFP cell cultures were examined on a Nikon Diaphot 300 microscope using a 470/40 nm Nikon filter. Fluorescent data was captured on a Leica DFC300 F imaging system. All cell culture was performed using tissue culture grade plasticware supplied by Falcon (Becton Dickinson, Lincoln Park, N.J., USA) or Nunc (Roskilde, Denmark).

Stable Integrative Transfection of hEC Cells

The floxed hPDF and GFP control vectors were each linearised by standard Pvu/restriction enzyme digestion and transfected into GCT 27X-1 cells by both electroporation and lipofection strategies.

Electroporation: A single cell suspension of 20-30×10$^6$ hEC cells was prepared by trypsin digestion and transfected with 40 µg of linearised DNA using a BTX ECM830 square wave electroporator (BTX, San Diego, Calif., USA), set to deliver an electrical discharge of 0.8 kV and a time constant of 0.1 ms (3 µF capacitance).

Lipofection: 2×10$^6$ hEC cells were seeded to a 78.5 cm$^2$ culture dish one day prior to transfection. Lipofection was performed by incubation of the cells in serum free medium for 6 hours with Lipofectamine 2000 reagent (Invitrogen) at 60 µg (1 µg/µl solution) and 20 µg of linearised DNA, according to the manufacturer's instructions. Cells were trypsinised 48 hours post-lipofection and plated at the same densities as for electroporated cells.

Transfected cells and control untransfected cells were plated at a density of 2×10$^6$ cells in 78.5 cm$^2$ dishes (~25,500 cells/cm$^2$) and cultured for up to 15 days both with and without conditioned medium, refreshing medium each 3-4 days. Puromycin selection was applied 2-3 days following transfection, initially at 0.4 µg/ml then at 1.0 µg/ml from days 10-15 post-transfection for effective selection of stable integrants. Puromycin resistant hEC colonies were picked into 2.0 cm$^2$ wells and expanded for subsequent freezing and further analyses. To ensure maintenance of self-renewing GFP control hEC cell lines, only colonies from conditioned medium plates were picked and expanded. All procedures for achieving stable integrative transfection of hEC cells were essentially as previously described for mouse ES cells (O'Brien, 2001).

CD30 Immunostaining hEC cell cultures were prepared for indirect immunofluorescent staining with a mouse anti-human CD30 monoclonal antibody (Dako, Glostrup, Denmark) by washing twice with PBS buffer, fixing in ethanol for 10 minutes on ice and storing at –20° C. Staining was performed using a 1:20 dilution of the primary antibody in a 0.1% Triton X-100 (Sigma)/2% goat serum (Invitrogen)/13.3% v/v BSA (Invitrogen) staining diluent prepared in PBS buffer. A Cy™3-conjugated goat anti-mouse IgG secondary antibody (Jackson ImmunoResearch Laboratories Inc., Westgrove, USA) was used at a 1:200 dilution in the above diluent buffer. CD30 positive cells were viewed using a 535/50 nm Nikon filter and comparative Hoechst (Sigma) staining with a UV 330-380 nm Nikon filter. Fluorescent data was captured on a Leica DFC300 F imaging system. All procedures for immunofluorescence staining were as described in SCS Ltd laboratory protocols.

Northern Blot Analysis

Poly A+ mRNA was prepared from subconfluent cultures of GCT 27X-1 cells cultured both on STO feeder cells and without feeder cells but in the presence of conditioned medium as described above. In addition, poly A+ mRNA was prepared from routine cultures of STO cells and E14Tg2a mouse ES cells, as controls for subsequent hybridisation. RNA lysates were prepared directly from cell cultures and poly A+ mRNA isolated by affinity chromatography on oligo (dT) cellulose (New England Biolabs, Beverly, Mass., USA) as previously described (O'Brien, 2001).

Extracted mRNA samples (3-3.5 µg) were electrophoresed on a 1% w/v agarose/0.66 M formaldehyde denaturing gel run in 1×MOPS buffer. RNA was transferred to Hybond N+ charged membranes (Amersham Pharmacia Biotech, Amersham, Buckinghamshire, UK) and hybridised with a $^{32}$P-labelled (Amersham Pharmacia Biotech) 960 bp hPDF cDNA fragment isolated by Eco RI restriction enzyme digestion from the pPyCAGhPDFIP vector (vector kindly supplied by Ian Chambers, ISCR, Edinburgh, UK). An 800 bp Hind III/EcoR I fragment of Gapdh coding sequence was used to re-hybridise some membranes to provide a loading control for mRNA samples (plasmid DNA kindly provided by Kate Loveland, MIRD, Melbourne, Australia). Membranes were exposed to Biomax MS (Kodak, Cedex, France) and Hyperfilm MP (Amersham Pharmacia Biotech) X-ray films between intensifying screens at –70° C. for up to 24 hrs. Blotting, hybridisation and routine molecular procedures were performed as described by Sambrook et al., (1989).

Results

Self-Renewal and Differentiation of GCT 27X-1 Cells

Routine culture of the GCT 27X-1 hEC cells was established as described in the methodology. Maintenance of a pluripotent phenotype was demonstrated, as judged by morphology, when cultured on a layer of STO feeder cells (FIG. 9a) or in the absence of STO feeder cells but in the presence of GCT 44-derived conditioned medium, at both a routine (FIG. 9b) and a clonal density (FIG. 14g). Withdrawal of conditioned medium from feeder-free cultures of hEC cells demonstrated the initiation of cell differentiation and complete loss of pluripotency in low density and clonal density cultures (FIG. 9c). It was further demonstrated that while feeder-free hEC cultures could not maintain a pluripotent morphology in cultures containing less than 25% (v/v) conditioned medium, a replacement of the routine culture medium with more than 75% (v/v) conditioned medium could not wholly support the survival and growth of the cultures (data not shown).

Endogenous Expression of hPDF in hEC Cells

To confirm endogenous expression of the hPDF gene in pluripotent GCT 27X-1 cells, a poly A+ mRNA Northern blot was prepared and hybridised with a radiolabelled probe corresponding to ~900 bp of hPDF cDNA sequence contained in the Floxed hPDF vector. Results in FIG. 10 show that the hPDF probe strongly detects a hybridisation band of ~2.4 kb in GCT 27X-1 cells grown both on feeder cells and without feeder cells but in the presence of conditioned medium. A second lesser hybridising transcript of ~5.6 kb size was also detected for both cultures and confirmed in repeat experiments on different RNA preparations (data not shown). No hybridising band was detected from mRNA prepared from a routine STO cell-only culture. A weak hybridising band of ~2.2 kb was detected in mouse E14Tg2a ES cell mRNA and is indicative of a homologous PDF transcript expressed in mouse pluripotent cells. Relative amounts of poly A+ mRNA in different gel lanes was determined by re-hybridisation of a membrane with the housekeeping gene Gapdh. This indicated that the mouse PDF transcript was detected at much lower levels, in comparison to the transcripts detected in hEC cells (data not shown).

The ~2.4 kb transcript detected in GCT 27X-1 hEC cell mRNA corresponds with that observed previously for a nullipotent hEC cell line GCT 27C4 derived from the same parental line.

Transfection of hPDF and Control GFP Vectors

In trial transfection experiments with the GFP control vector, both electroporation and lipofection strategies gave comparable results in GCT 27X-1 cells (data not shown). Transfection of GCT 27X-1 hEC cells with the Floxed hPDF vector was performed by both electroporation and lipofection, with a comparative GFP control vector transfection done by the lipofection method only (Table 2).

Stable integrative colonies harbouring the Floxed hPDF vector were established as feeder-free cultures both in the presence and absence of conditioned medium. Stable integrative colonies harbouring the GFP control vector were established under the same conditions, for the same number of plated cells. Stable, moderate sized colonies were established in 10-15 days for both vectors, with puromycin control plates for untransfected cells essentially clear of growth after this time.

Results in Table 2 indicate a slightly higher efficiency of transfection of GCT 27X-1 cells by lipofection than electroporation for the Floxed hPDF vector, but appear to show no difference in the number of stable hPDF integrant colonies established in the presence of conditioned medium to those without conditioned medium, compared with GFP control transfectants. While the culture of transfected cells without conditioned medium does not appear to hinder the ability for colonies to become established, the morphology of these does however, differ for Floxed hPDF and GFP control transfectants, as discussed in the following section (see Table 3).

An equivalent number of primary colonies, all displaying a tight pluripotent hEC phenotype were picked and expanded from both conditions for the hPDF transfectants. While GFP control colonies were established without conditioned medium for observation of morphology in stable colonies (see Table 3), these were not picked due to the anticipated initiation of differentiation in these colonies over this time frame.

It was noted that transfected hPDF cells appeared to take the same amount of time to establish colonies either in the presence or absence of conditioned medium, however, following picking those growing without conditioned medium expanded at a slower rate than those cultured with conditioned medium. This is a similar observation to that for PDF-expressing mouse ES cells established in cultures with and without LIF (see Example 8). It is also noteworthy that GFP control colonies expanded in conditioned medium displayed a slightly faster growth rate than their hPDF counterpart.

Morphological Observations for hPDF and GFP Control Transfectants

Figure 13A:
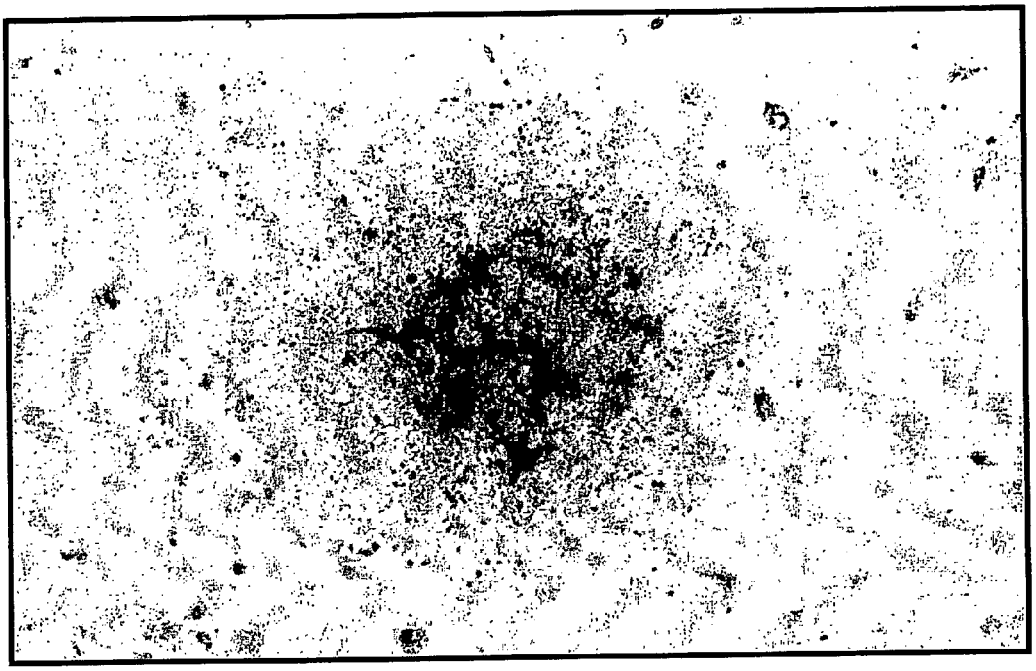
Figure 13B:
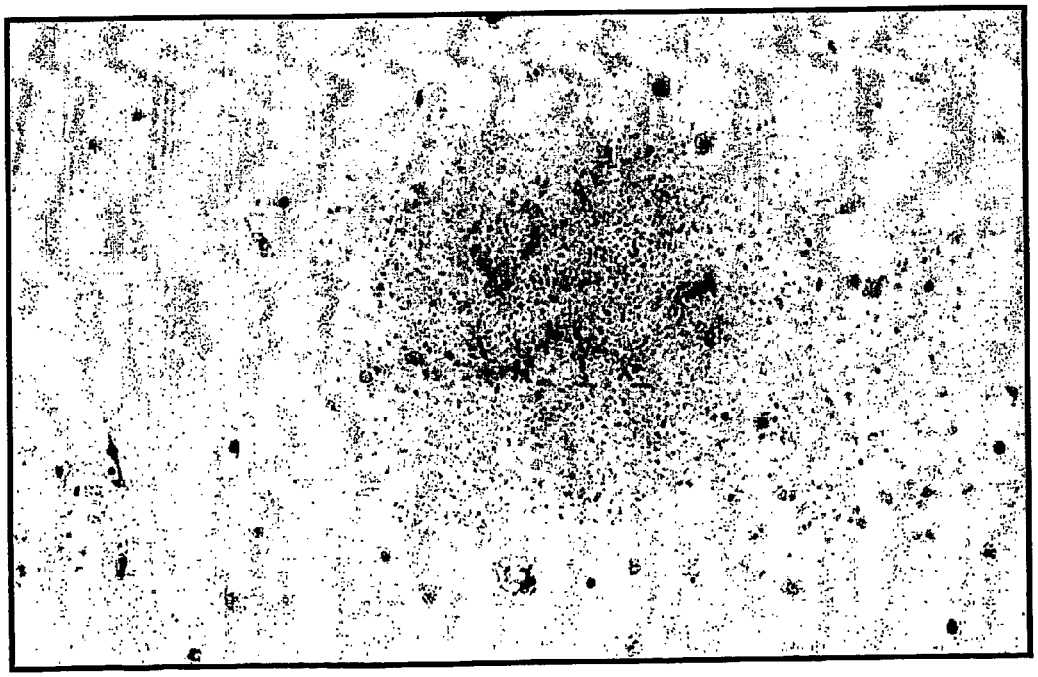
Figure 13C:
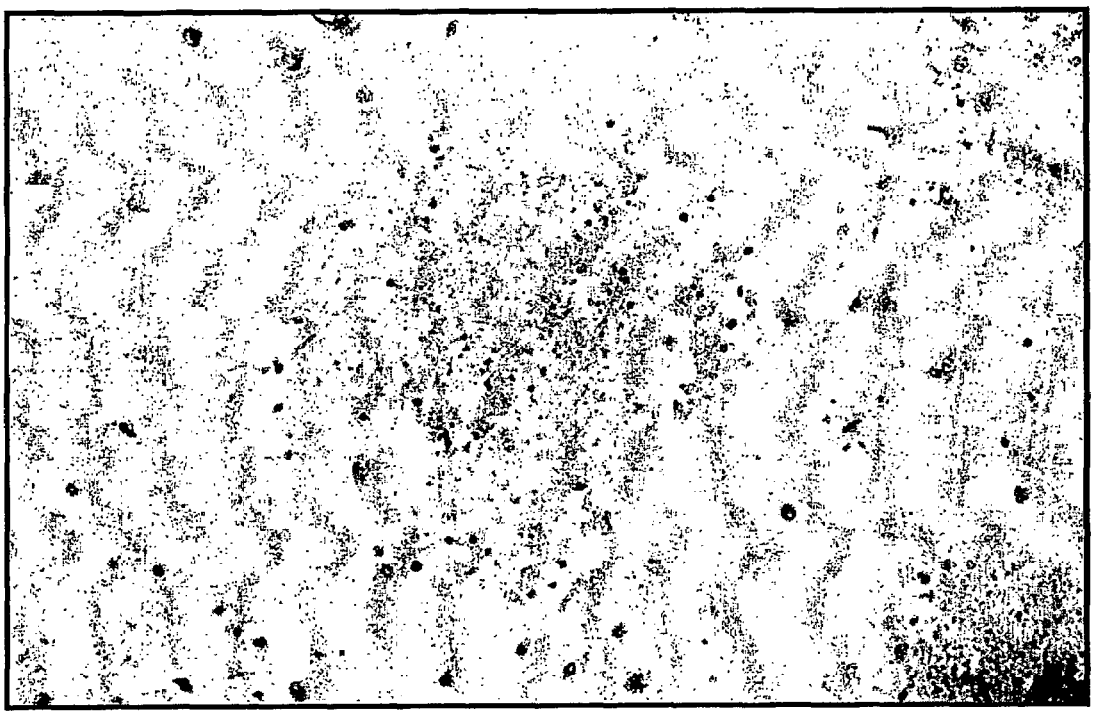

Stable transfectant colonies established following transfection with the Floxed hPDF and GFP control vectors and cultured in the presence and absence of conditioned medium were compared morphologically following Leishman's staining (Table 3). Colonies were scored as "tight", "medium" or "loose" to describe those puromycin resistant colonies maintaining a tight pluripotent phenotype, those starting to differentiate while maintaining some hEC phenotype and those that were completely loose and differentiated, respectively (FIGS. 13a-c).

Examination of colony morphology for primary transfectants, as shown in Table 3, indicates that while hPDF transfectants displayed a higher degree of tight hEC morphology in conditioned medium compared with GFP control transfectants, there was an increase in the ability for hPDF transfectants to hold a pluripotent phenotype without conditioned medium compared with GFP control colonies—for which an increase in loose, differentiating phenotype was observed.

While the variation in morphology for transfectants resulting from each vector may be influenced by the site of DNA integration into the genome, those resulting from the floxed hPDF transfection appear to display an increased ability to establish and maintain a pluripotent phenotype, even more so under conditions that would normally initiate differentiation and loss of pluripotency in colonies.

Generally, colonies observed on those hPDF transfection plates cultured without conditioned medium were smaller in size than those growing in conditioned medium, albeit with many displaying a tight pluripotent phenotype. It also remains possible that a synergistic effect occurs where hEC cells expressing exogenous hPDF are cultured in the presence of conditioned medium.

Maintenance of Pluripotency in hPDF-Expressing Transfectants

The ability of hPDF-expressing stable transfectant lines to definitively maintain a pluripotent phenotype under conditions that normally initiate GCT 27X-1 cell differentiation was confirmed by indirect immunofluorescent staining with the CD30 marker, specific to pluripotent hEC cells and not expressed in differentiating cell types.

Six hPDF-expressing cell lines, including one established and cultured without conditioned medium from the time of transfection, were cultured at a clonal density in both the presence and absence of conditioned medium. Four of the GFP control hEC transfectant cell lines (maintained in conditioned medium for self-renewal) as well as untransfected GCT 27X-1 hEC cells (also maintained in conditioned medium without feeder cells since the time of transfection experiments), were cultured in parallel at clonal density under the same conditions as for the hPDF lines. Morphological analysis and CD30 indirect immunofluorescent staining was performed when GFP control and GCT 27X-1 cells cultured without conditioned medium demonstrated complete or significant differentiation of colonies. It was noted that the untransfected GCT 27X-1 cells established expanded colonies at a faster rate than GFP control and hPDF cell lines.

Cell lines expressing the hPDF cDNA were shown to maintain a pluripotent phenotype at clonal density, with and without conditioned medium, while the GFP control cells and GCT 27X-1 cells could only maintain pluripotency where conditioned medium was present in the culture.

Results in FIG. 14 show the morphology of two hPDF clones expanded from transfection plates in the continuous presence (hPDF clone D7) or continuous absence (hPDF clone E7) of conditioned medium, and cultured at clonal density with and without conditioned medium (FIGS. 14 a-d). Both hPDF D7 and E7 clones demonstrate the ability to establish and maintain hEC colonies displaying a pluripotent cell phenotype under both conditions. Parallel clonal cultures of a GFP control clone, C15, and of untransfected GCT 27X-1 cells, confirm the ability of these cells to only establish and maintain pluripotent hEC colonies in the continued presence of conditioned medium. In the absence of conditioned medium the C15 and GCT 27X-1 cells are induced to differentiate, with few or no hEC cells remaining in the loosely formed colonies (FIGS. 14e-h).

Results in FIG. 15 confirm the above morphological observations with comparative CD30 and Hoechst immunofluorescence staining of individual colonies established from hPDF D7, hPDF E7, GFP C15 and GCT 27X-1 cell lines, cultured in the presence and absence of conditioned medium. All cell lines displayed the ability to maintain self-renewing CD30-positive colonies when cultured in the absence of feeder cells and presence of conditioned medium (FIGS. 15a-h). As the GCT 27X-1 cells established large expanded colonies more rapidly than the transfected cells, many of these had started to differentiate at their periphery as would be expected with overgrowth (FIGS. 15g-h). In the absence of both feeder cells and conditioned medium, only hPDF-expressing hEC cells were able to maintain CD30-positive colonies, while GFP control and GCT 27X-1 hEC cells could not maintain self-renewing colonies (FIGS. 15i-p). Again, any residual CD30-positive cells observed in GCT 27X-1 colonies, could be attributed to the more rapid expansion and overgrowth of these colonies (FIGS. 15o-p).

It was observed that the hPDF E7 cell line displayed a generally tighter hEC colony morphology (FIGS. 14a-d; FIGS. 15a, c, i, k) and stronger detection of the CD30 marker (FIGS. 15b, d, j, l) when compared with hPDF D7 cells, and may reflect the site of random DNA integration into the genome in each clone. The hPDF E7 cell line was initially established in the absence of both STO feeder cells and conditioned medium following transfection. After more than 8 weeks of continuous expansion under these culture condition the hPDF E7 hEC cell line continues to display a phenotype of self-renewing hEC cells (FIG. 16).

This demonstrates that exogenous expression of the human PDF cDNA in a human pluripotent cell line results in the maintenance of a pluripotent phenotype under conditions that normally drive these cells to differentiate and lose the ability to self-renew.

REFERENCES

Amit M., Carpenter M. K., Inokuma M. S., Chiu C. P., Harris C. P., Waknitz M. A., Itskovitz-Eldor J. and Thomson J. A. (2000) Dev. Biol. 227, 271-8.

Bain, G., Kitchens, D., Yao, M., Huettner, J. E., and Gottlieb, D. I. (1995). Embryonic stem cells express neuronal properties in vitro. Dev Biol 168, 342-357.

Baron, U. and Bujard (2000), Meth. Enz. 327, 401-421.

Burdon, T., Stracey, C., Chambers, I., Nichols, J., and Smith, A. (1999). Suppression of SHP-2 and ERK signalling promotes self-renewal of mouse embryonic stem cells. Dev Biol 210, 30-43.

Dani, C., Chambers, I., Johnstone, S., Robertson, M., Ebrahimi, B., Saito, M., Taga, T., Li, M., Burdon, T., Nichols, J., and Smith, A. (1998). Paracrine induction of stem cell renewal by LIF-deficient cells: a new ES cell regulatory pathway. Dev Biol 203, 149-162.

Doetschman, T. C., Eistetter, H., Katz, M., Schmidt, W., and Kemler, R. (1985). The in vitro development of blastocyst-derived embryonic stem cell lines: formation of visceral yolk sac, blood islands and myocardium. J Embryol Exp Morphol 87, 27-45.

Dynan and Tijan (1985) Nature 316, 774-78.

Eiges et al (2001) Current Biology, 11:514-518

Galli, G., Hofstetter, H., and Birnstiel, M. L. (1981). Two conserved sequence blocks within eukaryotic tRNA genes are major promoter elements. Nature 294, 626-631.

Gassmann, M., Donoho, G., and Berg, P. (1995). Maintenance of an extrachromosomal plasmid vector in mouse embryonic stem cells. Proc Natl Acad Sci U S A 92, 1292-1296.

Isalan and Choo (2001) Methods in Enzymology 340 593-609.

Latza, U., Foss, H. D., Durkop, H., et al. (1995). CD30 antigen in embryonal carcinoma and embryogenesis and release of the soluble molecule. Am. J. Pathol. 146, 463-471.

Letunic, I., Goodstadt, L., Dickens, N. J., Doerks, T., Schultz, J., Mott, R., Ciccarelli, F., Copley, R. R., Ponting, C. P., and Bork, P. (2002). Recent improvements to the SMART domain-based sequence annotation resource. Nucleic Acids Res 30, 242-244.

Li, M., Sendtner, M., and Smith, A. (1995). Essential function of LIF receptor in motor neurons. Nature 378, 724-727.

Li, M., Pevny, L., Lovell-Badge, R., and Smith, A. (1998). Generation of purified neural precursors from embryonic stem cells by lineage selection. Curr Biol 8, 971-974.

Matsui, Y., Zsebo, K., and Hogan, B. L. (1992). Derivation of pluripotential embryonic stem cells from murine primordial germ cells in culture. Cell 70, 841-847.

Niwa, H., Miyazaki, J., and Smith, A. G. (2000). Quantitative expression of Oct-3/4 defines differentiation, dedifferentiation or self-renewal of ES cells. Nat Genet 24, 372-376.

Niwa, H., Masui, S., Chambers, I., Smith, A. G., and Miyazaki, J. (2002b). Phenotypic complementation establishes requirements for specific POU domain and generic transactivation function of Oct-3/4 in embryonic stem cells. Mol Cell Biol 22, 1526-1536.

O'Brien, C. M. (2001). Identification and cloning of embryonic stem cell-specific genes. PhD thesis submission, Monash University, Australia.

Pera, M. F., Bennett, W., Cerretti, D. P. (1997). Expression of CD30 and CD30 ligand in cultured cell lines from human germ cell tumors. Lab Invest. 76, 497-504.

Pera, M. F., and Herszfeld, D., (1998) Reprod. Fertil. Develop. 10 551-555.

Pera, M. F. (1999). Biology of human testicular germ cell tumours. Repro. Med. Rev. 7, 141-154.

Picard, D. (2000), Meth. Enz. 327, 385-410.

Rathjen, P. D., Nichols, J., Toth, S., Edwards, D. R., Heath, J. K., and Smith, A. G. (1990). Developmentally programmed induction of differentiation inhibiting activity and the control of stem cell populations. Genes Dev 4, 2308-2318.

Ryskov, A. P., Ivanov, P. L., Kramerov, D. A., and Georgiev, G. P. (1983). Mouse ubiquitous B2 repeat in polysomal and cytoplasmic poly(A)+RNAs: uniderectional orientation and 3'-end localization. Nucleic Acids Res 11, 6541-6558.

Sambrook, J., Fritsch, E. F., Maniatis, T. (1989). Molecular Cloning. CSH Laboratory Press, Cold Spring Harbor, N.Y., USA.

Schultz, J., Milpetz, F., Bork, P., and Ponting, C. P. (1998). SMART, a simple modular architecture research tool: identification of signaling domains. Proc Natl Acad Sci U S A 95, 5857-5864.

Schwarze R S, Hruska K A & Dowdy S F, (2000) Trends Cell Biology, 10:290-295.

Shashikant, C. S., Utset, M. F., Violette, S. M., Wise, T. L., Einat, P., Einat, M., Pendleton, J. W., Schughart, K., and Ruddle, F. H. (1991). Homeobox genes in mouse development. Crit Rev Eukaryot Gene Expr 1, 207-245.

Vernallis, A. B., Hudson, K. R., and Heath, J. K. (1997). An antagonist for the leukemia inhibitoryfactor receptor inhibits leukemia inhibitory factor, cardiotrophih-1, ciliary neurotrophic factor, and oncostatin M. JBC 272, 26947-26952.

Xu C., Inokuma M. S. et al.(2001) Nat. Biotech.19, 971-974.

Yoshida, K., Chambers, I., Nichols, J., Smith, A., Saito, M., Yasukawa, K., Shoyab, M., Taga, T., and Kishimoto, T. (1994). Maintenance of the pluripotential phenotype of embryonic stem cells through direct activation of gp130 signalling pathways. Mech Dev 45, 163-171.

TABLE 2

Stable integrative transfection of GCT 27X-1 cells with a hPDF vector. Pluripotent GCT 27X-1 cells were transfected with the Floxed hPDF vector by both electroporation and lipofection strategies and stable transfectant colonies established without STO feeder cells in the presence and absence of conditioned medium (+/−CM), under puromycin selection. To provide control cell lines, GCT 27X-1 cells transfected by lipofection with the GFP control vector were established under the same conditions. Equivalent numbers of colonies were picked and expanded from all conditions, excepting GFP controls which were picked only from conditioned medium plates to maintain hEC colonies.

| | Floxed hPDF vector | | GFP control vector |
|---|---|---|---|
| | Electro-poration | Lipofection | Lipofection |
| # hEC cells transfected | 23 × 10$^6$ | 2 × 10$^6$ seeded 24 hrs prior | 2 × 10$^6$ seeded 24 hrs prior |
| # transfected cells seeded per 78.5 cm$^2$ plate | 2 × 10$^6$ | 2 × 10$^6$ plated 48 hrs post-t/f | 2 × 10$^6$ plated 48 hrs post-t/f |
| stable integrants established in +CM | 1:5102 (0.020%) 392 | 1:3597 (0.028%) 556 | 1:3425 (0.029%) 584 |
| stable integrants established in −CM | 1:4902 (0.020%) 408 | 1:3125 (0.032%) 640 | 1:2809 (0.036%) 712 |

TABLE 2-continued

Stable integrative transfection of GCT 27X-1 cells with a hPDF vector. Pluripotent GCT 27X-1 cells were transfected with the Floxed hPDF vector by both electroporation and lipofection strategies and stable transfectant colonies established without STO feeder cells in the presence and absence of conditioned medium (+/−CM), under puromycin selection. To provide control cell lines, GCT 27X-1 cells transfected by lipofection with the GFP control vector were established under the same conditions. Equivalent numbers of colonies were picked and expanded from all conditions, excepting GFP controls which were picked only from conditioned medium plates to maintain hEC colonies.

| | Floxed hPDF vector | | GFP control vector |
|---|---|---|---|
| | Electro-poration | Lipofection | Lipofection |
| # primary colonies picked: +CM culture | 24 | 24 | 24 |
| # primary colonies picked: −CM culture | 24 | 24 | 0 |

TABLE 3

Morphology of stable integrative hPDF and control GFP transfectant GCT 27X-1 cells in different culture conditions. Transfected cells were seeded at a density of ~25,500 cells/cm$^2$ and colonies established under puromycin selection for 10-15 days, in the presence and absence of conditioned medium (+/−CM). Colonies were scored for a tight, medium or loose phenotype with respect to pluripotency, following Leishman's staining. Floxed hPDF colony scores shown are taken from electroporation transfection plates.

| Colony Morphology | Floxed hPDF +CM | Floxed hPDF −CM | GFP control +CM | GFP control CM |
|---|---|---|---|---|
| Tight | 49 | 58 | 23 | 20 |
| Medium | 33 | 27 | 44 | 43 |
| Loose | 18 | 15 | 33 | 37 |
| Total count | 100 | 100 | 100 | 100 |

---

The invention claimed is:

1. An in vitro method of maintaining a mouse or human pluripotent cell in a pluripotent state comprising specifically increasing expression of a gene in the cell that encodes a factor which acts intracellularly and maintains pluripotency in said cell, wherein the gene has been introduced into the cell, wherein the factor is a polypeptide comprising the sequence of SEQ ID NO: 4 and wherein the cell is cultured so as to maintain the cell in a pluripotent state, thereby maintaining the mouse or human pluripotent cell in a pluripotent state.

2. The method of claim 1 wherein the gene is located on an episomal plasmid or is stably integrated.

3. The method of claim 1, wherein the factor maintains pluripotency of a human stem cell.

4. The method of claim 1, wherein the factor maintains pluripotency of a mouse embryonic stem cell.

5. The method of claim 1, wherein the factor maintains mouse embryonic stem cells and/or mouse embryonic germ cells in a pluripotent state.

6. The method of claim 1, wherein the factor maintains human embryonic stem cells in a pluripotent state.

7. The method of claim 1, wherein the factor maintains LIF non-responsive cells in a pluripotent state.

8. The method of claim 1, wherein the factor maintains human embryonic stem cells in a pluripotent state in the absence of feeder cells and in the absence of feeder cell extract.

9. The method of claim 8, wherein the factor is active in LIF non-responsive cells.

10. An in vitro method of maintaining a mouse or human pluripotent cell in a pluripotent state comprising specifically increasing expression of a gene in the cell that encodes a factor which acts intracellularly and maintains pluripotency in said cell in the absence of LIF, wherein the gene has been introduced into the cell, wherein the factor is a polypeptide comprising the sequence of SEQ ID NO: 4 and wherein the cell is cultured so as to maintain the cell in a pluripotent state, thereby maintaining the mouse or human pluripotent cell in a pluripotent state.

11. An in vitro method of maintaining a mouse or human pluripotent cell in a pluripotent state comprising specifically increasing expression of a gene in the cell that encodes a factor which acts intracellularly and maintains pluripotency in said cell in the absence of feeder cells and in the absence of feeder cell extract, wherein the gene has been introduced into the cell, wherein the factor is a polypeptide comprising the sequence of SEQ ID NO: 4 and wherein the cell is cultured so as to maintain the cell in a pluripotent state, thereby maintaining the mouse or human pluripotent cell in a pluripotent state.

* * * * *